United States Patent [19]
Guimarães et al.

[11] Patent Number: 5,858,707
[45] Date of Patent: Jan. 12, 1999

[54] PURIFIED MAMMALIAN NUCLEOBASE PERMEASES; NUCLEIC ACIDS; ANTIBODIES

[75] Inventors: M. Jorge Guimarães, Mountain View; J. Fernando Bazan, Menlo Park; Terrill K. McClanahan, Sunnyvale; Albert Zlotnik, Palo Alto, all of Calif.

[73] Assignee: Schering Corporation, Kenilworth, N.J.

[21] Appl. No.: 677,049

[22] Filed: Jul. 3, 1996

Related U.S. Application Data

[60] Provisional application No. 60/000,788, Jul. 3, 1995.
[51] Int. Cl.$^6$ .................................................. C12N 15/12
[52] U.S. Cl. .................... 435/69.1; 435/91.1; 435/320.1; 536/23.5
[58] Field of Search ................................. 435/69.1, 172.1, 435/325, 252.3, 254.11, 320.1, 925, 91.1; 530/350; 536/23.5

[56] References Cited

U.S. PATENT DOCUMENTS 5,410,031  4/1995  Wright et al. .......................... 536/23.6

OTHER PUBLICATIONS

M. Jorge Guimarães, et al., "A new approach to the study of haematopoietic development in the yolk sac and embryoid bodies," *Development*, 121: 3335–3346, Oct. 1995.

J. C. Bloch, et al., "Determination of a Specific Region of the Purine–Cytosine Permease Involved in the Recognition of Its Substrates," *Mol. Microbiol.* 6:2989–2997, 1992.

Ana Cumano, et al., "Differentiation and Characterization of B–Cell Precursors Detected in the Yolk Sac and Embryo Body of Embryos Beginning at the 10–to 12–Somite Stage," *Proc. Natl. Acad. Sci.* 90:6429–6433, Jul. 1993.

S. Danielsen, et al., "Characterization of the *Escherichia coli* codBA Operon Encoding Cytosine Permease and Cytosine Deaminase," *Mol. Microbiol.* 6:1335–1344, 1992.

George Diallinas, et al., "Genetic and Molecular Characterization of a Gene Encoding a Wide Specificty Purine Permease of *Aspergillus nidulans* Reveals a Novel Family of Transporters Conserved in Prokaryotes and Eukaryotes," *J. Biol. Chem.* 270:8610–8622, Apr. 14, 1995.

Jeffrey K. Griffith, et al., "Membrane Transport Proteins: Implications of Sequence Comparisons," *Curr. Opin. Cell Biol.* 4:684–695, 1992.

Matthias A. Hediger, "Structure, Function and Evolution of Solute Transporter in Prokaryotes and Eukaryotes," *J. Exp. Biol.* 196:15–49, 1994.

Peter J. F. Henderson, "The 12–Transmembrane Helix Transporters," *Curr. Opin. Cell Biol.* 5:708–721, 1993.

Reinhard Krämer, "Functional Principles of Solute Transport Systems: Concepts and Perspectives," *Biochim. Biophys. Acta* 1185:1–34, 1994.

Peter C. Maloney, "Bacterial Transporters," *Curr. Opin. Cell Biol.* 6:571–582, 1994.

Michael D. Marger, et al., "A Major Superfamily of Transmembrane Facilitators that Catalyse Uniport, Symport and Antiport," *TIBS* 18:13–20, Jan. 1993.

Hiroshi Nikaido, et al., "Transport Protein in Bacteria: Common Themes in Their Design," *Science* 258:936–942, Nov. 6, 1992.

Ana M. Pajor, et al., "Cloning and Expression of a Mammalian Na+/Nucleoside Cotransporter," *J. Biol. Chem.* 267:3557–3560, Feb. 25, 1992.

George R. Uhl, et al., "Transporter Explosion: Update on Uptake," *TIPS* 13:421–425, Dec. 1992.

Podbielski et al. (1996) Molec. Micro 21: 1087–1099 "Molecular Characterization of Group A Streptococcal (GAS) Oligopeptide Permease (Opp) . . . ".

*Primary Examiner*—Charles L. Patterson, Jr.
*Attorney, Agent, or Firm*—Sheela Mohan-Peterson; Edwin P. Ching

[57] ABSTRACT

Nucleobase permeases from mammals, reagents related thereto including purified proteins, specific antibodies, and nucleic acids hybridizing to or encoding such proteins. Methods of making and using said reagents and diagnostic kits are also provided.

25 Claims, 8 Drawing Sheets

```
EcUraA   114  G W L D V L F P P A A M G A I V A V I G L E L A G V A A G M
BsPyrP   117  G W L M K I L P P V V V G P V I I V G L G L A S T A V N M
BcPyrP   115  R W V M K L L P P V V V G P V I V G L G L A G T A V G M
EcORF    151  H L A R R I T P L V S G V V M I G L S L I Q V G L T S
AnUAPA   233  K V I Q K I F P P I V T G P T V M L I G I S L I G T G I F K D
AnUAPC   207  R L L K A L F P P I V T G P T V F L G A S L I G N A M K D
BsXpt    115  G K L V S F F P P V V T G S V V T I I G I T L M P V A M N N
BsORF    117  D R L A K L F T P V V T G V V Y L L L V M Q L S Q P I K G
MoYSLP1  189  P G R V F P V C P L V L A P S L V V A G L S A H K E V A Q F
```

TM9

```
EcUraA   320  G K L A A I Q M I P L P V M G G V S L L L Y G V I G A S G I R V L I
BsPyrP   330  G K I S A L I S S V P S A V M G G V S F L L F G I A S S G L R M L I
BcPyrP   325  G K I T A L I S S I P T P V M G G V S I L L F G I A S S G L R M L I
EcORF    366  R A V S G F V Q H P E R V L G G A T L V M F G T I A A S G V R I V S
AnUAPA   459  A K F A A I V A P N S V M G C M K T F L F A S V V I S G Q A V A
AnUAPC   437  A K F A A A L V A P S S V L G G M T F L F S S V A I S G V R I M C
BsXpt    323  P K I A A F T T I I P S A V L G G A M V A M F G M V A Y G I K M L S
BsORF    328  P F F M N T F A S L P S P V G F A V N F V V F S A M G G L A F A E F D
MoYSLP1  413  R R L A Q L F T S I P L P V L G G V L G V T Q A V V L S A G F S S E H
```

TM10

```
EcUraA   358  V D Y N K A Q M L I L T S V I L I G V S G A K V N I G
BsPyrP   368  I D Y E N N R M L I T S V I L V G V G G A F H Q V S
BcPyrP   363  V D F G Q T R M L V I A S V I L V G I G G A V L K I S
EcORF    401  R E P L N R R A L L I A L S L A V G L G V S Q Q R L I
AnUAPA   494  K A P F T R R N R F L L T A S M A L G Y G A T L V P T W
AnUAPC   472  S V D W T R R N R F L L T A S F A V G M A A T L V P D W
BsXpt    359  I D F A K Q E N L L V A C S V G L G L G V T V V P D I
BsORF    365  E K E E S K R V R S L G L S L L T G V G I M F V P E T
MoYSLP1  449  A D I D S G R N V F L V G F S I F M A L L L P R W L R E
```

FIG. 4

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 2085 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 48..1883

( i x ) FEATURE:
        ( A ) NAME/KEY: misc_feature
        ( B ) LOCATION: 366..1883
        ( D ) OTHER INFORMATION: /note= "Form 2"

( i x ) FEATURE:
        ( A ) NAME/KEY: misc_feature
        ( B ) LOCATION: 1515..1883
        ( D ) OTHER INFORMATION: /note= "Form 3"

( i x ) FEATURE:
        ( A ) NAME/KEY: misc_feature
        ( B ) LOCATION: 1659..1883
        ( D ) OTHER INFORMATION: /note= "Form 4"

( x i ) SEQUENCE DESCRIPTION: SEQ ID NO:1:

```
CCCACGCGTC  CGCTGGGGCA  GCCAAGACGC  AATCAAGTCA  GGGCAGC ATG AGC CGA           56
                                                         Met Ser Arg
                                                          1

TCA CCT CTC CAT CCC ATT CCA CTT CTA TCT GAG GGC TAC CAG GAT ACC              104
Ser Pro Leu His Pro Ile Pro Leu Leu Ser Glu Gly Tyr Gln Asp Thr
     5               10                  15

CCT GCT CCC CTG CCA CCA CTG CTA CCC CCT CTC CAG AAT CCC TCC TCC              152
Pro Ala Pro Leu Pro Pro Leu Leu Pro Pro Leu Gln Asn Pro Ser Ser
 20              25                  30                  35

CGT TCT TGG GCC TCT CGG GTG TTT GGG CCT TCC ACC TGG GGG CTC AGC              200
Arg Ser Trp Ala Ser Arg Val Phe Gly Pro Ser Thr Trp Gly Leu Ser
```

|  |  |  |  |  |  |  |  |  |  |  |  |  |  |  |  |  |
|---|---|---|---|---|---|---|---|---|---|---|---|---|---|---|---|---|
|  |  |  |  |  | 40 |  |  |  |  | 45 |  |  |  |  | 50 |  |
| TGT | CTT | CTG | GCT | CTA | CAG | CAT | TTC | CTG | GTC | TTG | GCA | TCT | TTG | CTC | TGG | 248 |
| Cys | Leu | Leu | Ala | Leu | Gln | His | Phe | Leu | Val | Leu | Ala | Ser | Leu | Leu | Trp |  |
|  |  |  |  | 55 |  |  |  | 60 |  |  |  |  | 65 |  |  |  |
| GCC | TCC | CAC | CTG | CTG | CTG | CTT | CAT | GGT | CTT | CCC | CCA | GGA | GGG | CTC | TCA | 296 |
| Ala | Ser | His | Leu | Leu | Leu | Leu | His | Gly | Leu | Pro | Pro | Gly | Gly | Leu | Ser |  |
|  |  | 70 |  |  |  |  | 75 |  |  |  |  | 80 |  |  |  |  |
| TAC | CCA | CCC | GCT | CAG | CTC | CTG | GCT | TCC | AGT | TTC | TTT | TCA | TGT | GGC | CTG | 344 |
| Tyr | Pro | Pro | Ala | Gln | Leu | Leu | Ala | Ser | Ser | Phe | Phe | Ser | Cys | Gly | Leu |  |
|  | 85 |  |  |  |  | 90 |  |  |  |  | 95 |  |  |  |  |  |
| TCT | ACG | GTC | CTG | CAG | ACT | TGG | ATG | GGC | AGC | AGG | CTA | CCT | CTA | ATC | CAG | 392 |
| Ser | Thr | Val | Leu | Gln | Thr | Trp | Met | Gly | Ser | Arg | Leu | Pro | Leu | Ile | Gln |  |
| 100 |  |  |  |  | 105 |  |  |  |  | 110 |  |  |  |  | 115 |  |
| GCT | CCG | TCC | CTA | GAG | TTT | CTT | ATC | CCC | GCA | CTG | GTG | CTG | ACA | AAC | CAG | 440 |
| Ala | Pro | Ser | Leu | Glu | Phe | Leu | Ile | Pro | Ala | Leu | Val | Leu | Thr | Asn | Gln |  |
|  |  |  |  | 120 |  |  |  |  | 125 |  |  |  |  | 130 |  |  |
| AAG | CTA | CCT | CTG | ACG | ACC | AAG | ACA | CCT | GGA | AAT | GCC | TCC | CTC | TCA | CTG | 488 |
| Lys | Leu | Pro | Leu | Thr | Thr | Lys | Thr | Pro | Gly | Asn | Ala | Ser | Leu | Ser | Leu |  |
|  |  |  | 135 |  |  |  |  | 140 |  |  |  |  | 145 |  |  |  |
| CCC | CTG | TGT | AGT | TTG | ACA | AGA | AGC | TGC | CAT | GGC | CTG | GAG | CTC | TGG | AAC | 536 |
| Pro | Leu | Cys | Ser | Leu | Thr | Arg | Ser | Cys | His | Gly | Leu | Glu | Leu | Trp | Asn |  |
|  |  | 150 |  |  |  |  | 155 |  |  |  |  | 160 |  |  |  |  |
| ACT | TCT | CTC | CGA | GAG | GTG | TCG | GGG | GCA | GTG | GTG | GTG | TCC | GGG | CTG | CTG | 584 |
| Thr | Ser | Leu | Arg | Glu | Val | Ser | Gly | Ala | Val | Val | Val | Ser | Gly | Leu | Leu |  |
|  | 165 |  |  |  |  | 170 |  |  |  |  | 175 |  |  |  |  |  |
| CAG | GGC | ACT | ATA | GGA | CTT | CTA | GGG | GTG | CCT | GGC | CGT | GTG | TTC | CCC | TAC | 632 |
| Gln | Gly | Thr | Ile | Gly | Leu | Leu | Gly | Val | Pro | Gly | Arg | Val | Phe | Pro | Tyr |  |
| 180 |  |  |  |  | 185 |  |  |  |  | 190 |  |  |  |  | 195 |  |
| TGT | GGG | CCA | CTG | GTG | CTG | GCT | CCC | AGC | CTG | GTT | GTG | GCA | GGG | CTT | TCT | 680 |
| Cys | Gly | Pro | Leu | Val | Leu | Ala | Pro | Ser | Leu | Val | Val | Ala | Gly | Leu | Ser |  |
|  |  |  |  | 200 |  |  |  |  | 205 |  |  |  |  | 210 |  |  |
| GCC | CAC | AAG | GAG | GTG | GCC | CAG | TTC | TGT | TCT | GCT | CAC | TGG | GGC | CTG | GCC | 728 |
| Ala | His | Lys | Glu | Val | Ala | Gln | Phe | Cys | Ser | Ala | His | Trp | Gly | Leu | Ala |  |
|  |  |  | 215 |  |  |  |  | 220 |  |  |  |  | 225 |  |  |  |
| TTG | CTG | CTC | ATC | CTG | CTC | ATG | GTG | GTA | TGC | TCT | CAG | CAC | CTG | GGT | TCA | 776 |
| Leu | Leu | Leu | Ile | Leu | Leu | Met | Val | Val | Cys | Ser | Gln | His | Leu | Gly | Ser |  |
|  |  | 230 |  |  |  |  | 235 |  |  |  |  | 240 |  |  |  |  |
| TGC | CAG | ATA | CCC | CTT | TGC | TCC | TGG | AGG | CCA | TCT | TCA | ACT | TCA | ACT | CAC | 824 |
| Cys | Gln | Ile | Pro | Leu | Cys | Ser | Trp | Arg | Pro | Ser | Ser | Thr | Ser | Thr | His |  |
| 245 |  |  |  |  | 250 |  |  |  |  | 255 |  |  |  |  |  |  |
| ATT | TGT | ATT | CCC | GTC | TTC | CGA | CTC | CTT | TCG | GTG | CTT | GCC | CCT | GTG | GCC | 872 |
| Ile | Cys | Ile | Pro | Val | Phe | Arg | Leu | Leu | Ser | Val | Leu | Ala | Pro | Val | Ala |  |
| 260 |  |  |  |  | 265 |  |  |  |  | 270 |  |  |  |  | 275 |  |
| TGT | GTG | TGG | TTC | ATC | TCT | GCC | TTT | GTG | GGT | ACG | AGT | GTT | ATC | CCT | CTG | 920 |
| Cys | Val | Trp | Phe | Ile | Ser | Ala | Phe | Val | Gly | Thr | Ser | Val | Ile | Pro | Leu |  |
|  |  |  |  | 280 |  |  |  |  | 285 |  |  |  |  | 290 |  |  |
| CAG | CTG | TCT | GAG | CCC | TCG | GAT | GCA | CCT | TGG | TTT | TGG | CTG | CCA | CAC | CCA | 968 |
| Gln | Leu | Ser | Glu | Pro | Ser | Asp | Ala | Pro | Trp | Phe | Trp | Leu | Pro | His | Pro |  |
|  |  |  | 295 |  |  |  |  | 300 |  |  |  |  | 305 |  |  |  |
| GGT | GAG | TGG | GAA | TGG | CCC | TTG | CTG | ACA | CCC | AGG | GCC | CTG | GCT | GCA | GGC | 1016 |
| Gly | Glu | Trp | Glu | Trp | Pro | Leu | Leu | Thr | Pro | Arg | Ala | Leu | Ala | Ala | Gly |  |
|  |  | 310 |  |  |  |  | 315 |  |  |  |  | 320 |  |  |  |  |
| ATC | TCC | ATG | GCT | TTG | GCA | GCC | TCC | ACC | AGC | TCC | TTG | GGT | TGC | TAT | GCT | 1064 |
| Ile | Ser | Met | Ala | Leu | Ala | Ala | Ser | Thr | Ser | Ser | Leu | Gly | Cys | Tyr | Ala |  |
|  | 325 |  |  |  |  | 330 |  |  |  |  | 335 |  |  |  |  |  |
| CTG | TGT | GGC | CAG | CTG | CTG | CGT | TTG | TCT | CCT | CCG | CCA | CCT | CAT | GCC | TGC | 1112 |
| Leu | Cys | Gly | Gln | Leu | Leu | Arg | Leu | Ser | Pro | Pro | Pro | Pro | His | Ala | Cys |  |
| 340 |  |  |  |  | 345 |  |  |  |  | 350 |  |  |  |  | 355 |  |
| AGT | CGA | GGG | CTG | AGC | CTG | GAG | GGG | CTG | GGC | AGT | GTG | CTG | GCA | GGG | CTG | 1160 |
| Ser | Arg | Gly | Leu | Ser | Leu | Glu | Gly | Leu | Gly | Ser | Val | Leu | Ala | Gly | Leu |  |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 360 |     |     |     | 365 |     |     |     |     | 370 |     |     |      |
| CTG | GGG | AGC | CCC | CTG | GGC | ACT | GCA | TCC | AGC | TTC | CCC | AAC | GTA | GGC | ACA | 1208 |
| Leu | Gly | Ser | Pro | Leu | Gly | Thr | Ala | Ser | Ser | Phe | Pro | Asn | Val | Gly | Thr |      |
|     |     |     | 375 |     |     |     | 380 |     |     |     |     | 385 |     |     |     |      |
| GTG | AGT | CTT | TTT | CAG | ACT | GGC | TCT | CGG | AGA | GTG | GCC | CAC | CTA | GTG | GGG | 1256 |
| Val | Ser | Leu | Phe | Gln | Thr | Gly | Ser | Arg | Arg | Val | Ala | His | Leu | Val | Gly |      |
|     |     |     | 390 |     |     |     | 395 |     |     |     |     | 400 |     |     |     |      |
| TTG | TTC | TGC | ATG | GGG | CTT | GGG | CTC | TCC | CCA | AGG | CTG | GCT | CAG | CTA | TTT | 1304 |
| Leu | Phe | Cys | Met | Gly | Leu | Gly | Leu | Ser | Pro | Arg | Leu | Ala | Gln | Leu | Phe |      |
|     | 405 |     |     |     |     | 410 |     |     |     |     | 415 |     |     |     |     |      |
| ACC | AGC | ATC | CCA | CTG | CCT | GTG | CTT | GGT | GGG | GTA | CTG | GGA | GTG | ACC | CAG | 1352 |
| Thr | Ser | Ile | Pro | Leu | Pro | Val | Leu | Gly | Gly | Val | Leu | Gly | Val | Thr | Gln |      |
| 420 |     |     |     |     | 425 |     |     |     |     | 430 |     |     |     |     | 435 |      |
| GCT | GTA | GTT | CTG | TCT | GCT | GGA | TTC | TCC | AGC | TTT | CAC | CTG | GCT | GAC | ATT | 1400 |
| Ala | Val | Val | Leu | Ser | Ala | Gly | Phe | Ser | Ser | Phe | His | Leu | Ala | Asp | Ile |      |
|     |     |     |     |     | 440 |     |     |     | 445 |     |     |     |     | 450 |     |      |
| GAC | TCT | GGG | CGA | AAT | GTC | TTC | ATC | GTG | GGC | TTC | TCC | ATC | TTC | ATG | GCC | 1448 |
| Asp | Ser | Gly | Arg | Asn | Val | Phe | Ile | Val | Gly | Phe | Ser | Ile | Phe | Met | Ala |      |
|     |     |     | 455 |     |     |     |     | 460 |     |     |     |     | 465 |     |     |      |
| TTG | CTT | TTG | CCA | AGG | TGG | CTC | AGG | GAA | GCC | CCA | GTC | CTG | CTC | AAC | ACA | 1496 |
| Leu | Leu | Leu | Pro | Arg | Trp | Leu | Arg | Glu | Ala | Pro | Val | Leu | Leu | Asn | Thr |      |
|     |     | 470 |     |     |     |     | 475 |     |     |     |     | 480 |     |     |     |      |
| GGC | TGG | AGC | CCC | CTG | GAT | ATG | TTT | CTT | CGT | TCT | TTG | CTG | GCA | GAA | CCC | 1544 |
| Gly | Trp | Ser | Pro | Leu | Asp | Met | Phe | Leu | Arg | Ser | Leu | Leu | Ala | Glu | Pro |      |
|     | 485 |     |     |     |     | 490 |     |     |     |     | 495 |     |     |     |     |      |
| ATT | TTC | TTA | GCT | GGT | CTA | CTG | GGC | TTT | CTC | CTA | GAA | AAC | ACT | ATA | TCT | 1592 |
| Ile | Phe | Leu | Ala | Gly | Leu | Leu | Gly | Phe | Leu | Leu | Glu | Asn | Thr | Ile | Ser |      |
| 500 |     |     |     |     | 505 |     |     |     |     | 510 |     |     |     |     | 515 |      |
| GGT | ACA | CGG | GCT | GAG | AGA | GGC | TTA | GGT | CAG | AGG | CTG | CCA | ACT | TCT | TTC | 1640 |
| Gly | Thr | Arg | Ala | Glu | Arg | Gly | Leu | Gly | Gln | Arg | Leu | Pro | Thr | Ser | Phe |      |
|     |     |     |     | 520 |     |     |     |     | 525 |     |     |     |     | 530 |     |      |
| ACT | GCC | CAA | GAA | ATT | CAA | ATG | CTT | CAG | CAA | TCC | AGG | AGG | AAA | GCT | GCT | 1688 |
| Thr | Ala | Gln | Glu | Ile | Gln | Met | Leu | Gln | Gln | Ser | Arg | Arg | Lys | Ala | Ala |      |
|     |     |     | 535 |     |     |     |     | 540 |     |     |     |     | 545 |     |     |      |
| CAA | GAG | TAT | GGG | CTT | CCT | TTA | CCC | ATC | AAA | AAC | CTG | TGT | TCC | TGC | ATC | 1736 |
| Gln | Glu | Tyr | Gly | Leu | Pro | Leu | Pro | Ile | Lys | Asn | Leu | Cys | Ser | Cys | Ile |      |
|     |     | 550 |     |     |     |     | 555 |     |     |     |     | 560 |     |     |     |      |
| CCA | CAG | CCT | CTC | CAC | TGC | CTC | TGT | CCA | ATG | CCT | GAA | GAC | TCT | GGG | GAT | 1784 |
| Pro | Gln | Pro | Leu | His | Cys | Leu | Cys | Pro | Met | Pro | Glu | Asp | Ser | Gly | Asp |      |
|     | 565 |     |     |     |     | 570 |     |     |     |     | 575 |     |     |     |     |      |
| GAA | GGA | GGA | TCC | TCT | AAA | ACA | GGA | GAG | AGA | GCC | GAC | TTG | TTG | CCT | AAC | 1832 |
| Glu | Gly | Gly | Ser | Ser | Lys | Thr | Gly | Glu | Arg | Ala | Asp | Leu | Leu | Pro | Asn |      |
| 580 |     |     |     |     | 585 |     |     |     |     | 590 |     |     |     |     | 595 |      |
| TCT | GGG | GAA | TCG | TAC | TCC | ACA | GCT | AGC | AGA | GAA | GGG | GTT | AGG | TCC | CAG | 1880 |
| Ser | Gly | Glu | Ser | Tyr | Ser | Thr | Ala | Ser | Arg | Glu | Gly | Val | Arg | Ser | Gln |      |
|     |     |     |     | 600 |     |     |     |     | 605 |     |     |     |     | 610 |     |      |

| TAA | TCATCAAGAC | CACCATTTTT | GTCTTAGTTT | AGCAGTAACT | GCCACCTTGC | 1933 |
| *   |            |            |            |            |            |      |

TGGAGTCTGT ATACTTTGTC CCAGTGGAGG TGGATGTGGC CCACTTGCAA AATGGGCTGC   1993

CTTTCCTCCT CTTAAGACTT GAGCAGAGGC CATGGTTTAG CGGGTTGGAA CTGAATAAAT   2053

GAGATTTCTG CCTGTAAAAA AAAAAAAAAA AA                                 2085

( 2 ) INFORMATION FOR SEQ ID NO:2:

( i ) SEQUENCE CHARACTERISTICS:
      ( A ) LENGTH: 611 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

| Met | Ser | Arg | Ser | Pro | Leu | His | Pro | Ile | Pro | Leu | Leu | Ser | Glu | Gly | Tyr |
| 1 | | | | 5 | | | | | 10 | | | | | | 15 |

| Gln | Asp | Thr | Pro | Ala | Pro | Leu | Pro | Pro | Leu | Leu | Pro | Pro | Leu | Gln | Asn |
| | | | 20 | | | | | 25 | | | | | | 30 | |

| Pro | Ser | Ser | Arg | Ser | Trp | Ala | Ser | Arg | Val | Phe | Gly | Pro | Ser | Thr | Trp |
| | | | 35 | | | | | 40 | | | | | 45 | | |

| Gly | Leu | Ser | Cys | Leu | Leu | Ala | Leu | Gln | His | Phe | Leu | Val | Leu | Ala | Ser |
| | | 50 | | | | | 55 | | | | | 60 | | | |

| Leu | Leu | Trp | Ala | Ser | His | Leu | Leu | Leu | Leu | His | Gly | Leu | Pro | Pro | Gly |
| 65 | | | | | 70 | | | | | 75 | | | | | 80 |

| Gly | Leu | Ser | Tyr | Pro | Pro | Ala | Gln | Leu | Leu | Ala | Ser | Ser | Phe | Phe | Ser |
| | | | | 85 | | | | | 90 | | | | | 95 | |

| Cys | Gly | Leu | Ser | Thr | Val | Leu | Gln | Thr | Trp | Met | Gly | Ser | Arg | Leu | Pro |
| | | | 100 | | | | | 105 | | | | | 110 | | |

| Leu | Ile | Gln | Ala | Pro | Ser | Leu | Glu | Phe | Leu | Ile | Pro | Ala | Leu | Val | Leu |
| | | | 115 | | | | | 120 | | | | | 125 | | |

| Thr | Asn | Gln | Lys | Leu | Pro | Leu | Thr | Thr | Lys | Thr | Pro | Gly | Asn | Ala | Ser |
| | | 130 | | | | | 135 | | | | | 140 | | | |

| Leu | Ser | Leu | Pro | Leu | Cys | Ser | Leu | Thr | Arg | Ser | Cys | His | Gly | Leu | Glu |
| 145 | | | | | 150 | | | | | 155 | | | | | 160 |

| Leu | Trp | Asn | Thr | Ser | Leu | Arg | Glu | Val | Ser | Gly | Ala | Val | Val | Val | Ser |
| | | | | 165 | | | | | 170 | | | | | 175 | |

| Gly | Leu | Leu | Gln | Gly | Thr | Ile | Gly | Leu | Leu | Gly | Val | Pro | Gly | Arg | Val |
| | | | | 180 | | | | | 185 | | | | | 190 | |

| Phe | Pro | Tyr | Cys | Gly | Pro | Leu | Val | Leu | Ala | Pro | Ser | Leu | Val | Val | Ala |
| | | | 195 | | | | | 200 | | | | | 205 | | |

| Gly | Leu | Ser | Ala | His | Lys | Glu | Val | Ala | Gln | Phe | Cys | Ser | Ala | His | Trp |
| | | 210 | | | | | 215 | | | | | 220 | | | |

| Gly | Leu | Ala | Leu | Leu | Leu | Ile | Leu | Leu | Met | Val | Val | Cys | Ser | Gln | His |
| 225 | | | | | 230 | | | | | 235 | | | | | 240 |

| Leu | Gly | Ser | Cys | Gln | Ile | Pro | Leu | Cys | Ser | Trp | Arg | Pro | Ser | Ser | Thr |
| | | | | 245 | | | | | 250 | | | | | 255 | |

| Ser | Thr | His | Ile | Cys | Ile | Pro | Val | Phe | Arg | Leu | Leu | Ser | Val | Leu | Ala |
| | | | 260 | | | | | 265 | | | | | 270 | | |

| Pro | Val | Ala | Cys | Val | Trp | Phe | Ile | Ser | Ala | Phe | Val | Gly | Thr | Ser | Val |
| | | | 275 | | | | | 280 | | | | | 285 | | |

| Ile | Pro | Leu | Gln | Leu | Ser | Glu | Pro | Ser | Asp | Ala | Pro | Trp | Phe | Trp | Leu |
| | | 290 | | | | | 295 | | | | | 300 | | | |

| Pro | His | Pro | Gly | Glu | Trp | Glu | Trp | Pro | Leu | Leu | Thr | Pro | Arg | Ala | Leu |
| 305 | | | | | 310 | | | | | 315 | | | | | 320 |

| Ala | Ala | Gly | Ile | Ser | Met | Ala | Leu | Ala | Ala | Ser | Thr | Ser | Ser | Leu | Gly |
| | | | | 325 | | | | | 330 | | | | | 335 | |

| Cys | Tyr | Ala | Leu | Cys | Gly | Gln | Leu | Leu | Arg | Leu | Ser | Pro | Pro | Pro | Pro |
| | | | 340 | | | | | 345 | | | | | 350 | | |

| His | Ala | Cys | Ser | Arg | Gly | Leu | Ser | Leu | Glu | Gly | Leu | Gly | Ser | Val | Leu |
| | | | 355 | | | | | 360 | | | | | 365 | | |

| Ala | Gly | Leu | Leu | Gly | Ser | Pro | Leu | Gly | Thr | Ala | Ser | Ser | Phe | Pro | Asn |
| | | 370 | | | | | 375 | | | | | 380 | | | |

| Val | Gly | Thr | Val | Ser | Leu | Phe | Gln | Thr | Gly | Ser | Arg | Arg | Val | Ala | His |
| 385 | | | | | 390 | | | | | 395 | | | | | 400 |

| Leu | Val | Gly | Leu | Phe | Cys | Met | Gly | Leu | Gly | Leu | Ser | Pro | Arg | Leu | Ala |
| | | | | 405 | | | | | 410 | | | | | 415 | |

```
Gln  Leu  Phe  Thr  Ser  Ile  Pro  Leu  Pro  Val  Leu  Gly  Gly  Val  Leu  Gly
               420                      425                      430

Val  Thr  Gln  Ala  Val  Val  Leu  Ser  Ala  Gly  Phe  Ser  Ser  Phe  His  Leu
          435                      440                     445

Ala  Asp  Ile  Asp  Ser  Gly  Arg  Asn  Val  Phe  Ile  Val  Gly  Phe  Ser  Ile
     450                      455                     460

Phe  Met  Ala  Leu  Leu  Leu  Pro  Arg  Trp  Leu  Arg  Glu  Ala  Pro  Val  Leu
465                      470                     475                          480

Leu  Asn  Thr  Gly  Trp  Ser  Pro  Leu  Asp  Met  Phe  Leu  Arg  Ser  Leu  Leu
                    485                     490                          495

Ala  Glu  Pro  Ile  Phe  Leu  Ala  Gly  Leu  Leu  Gly  Phe  Leu  Leu  Glu  Asn
               500                     505                     510

Thr  Ile  Ser  Gly  Thr  Arg  Ala  Glu  Arg  Gly  Leu  Gly  Gln  Arg  Leu  Pro
          515                     520                     525

Thr  Ser  Phe  Thr  Ala  Gln  Glu  Ile  Gln  Met  Leu  Gln  Gln  Ser  Arg  Arg
     530                     535                     540

Lys  Ala  Ala  Gln  Glu  Tyr  Gly  Leu  Pro  Leu  Pro  Ile  Lys  Asn  Leu  Cys
545                      550                     555                          560

Ser  Cys  Ile  Pro  Gln  Pro  Leu  His  Cys  Leu  Cys  Pro  Met  Pro  Glu  Asp
               565                     570                     575

Ser  Gly  Asp  Glu  Gly  Gly  Ser  Ser  Lys  Thr  Gly  Glu  Arg  Ala  Asp  Leu
               580                     585                     590

Leu  Pro  Asn  Ser  Gly  Glu  Ser  Tyr  Ser  Thr  Ala  Ser  Arg  Glu  Gly  Val
          595                     600                     605

Arg  Ser  Gln
     610
```

( 2 ) INFORMATION FOR SEQ ID NO:3:

( i ) SEQUENCE CHARACTERISTICS:
        ( A ) LENGTH: 108 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..77

( x i ) SEQUENCE DESCRIPTION: SEQ ID NO:3:

```
CC  ACG  CGT  CCG  CCC  ACC  TGC  TGC  TGC  TTC  ATG  GTC  TTC  CCC  CAG  GAG           47
    Thr  Arg  Pro  Pro  Thr  Cys  Cys  Cys  Phe  Met  Val  Phe  Pro  Gln  Glu
     1                    5                    10                         15

GGC  TCT  CAT  ACC  CAC  CCG  CTC  AGC  TCC  CAG  TAATCATCAA  GACCACCATT              97
Gly  Ser  His  Thr  His  Pro  Leu  Ser  Ser  Gln
                    20                     25

TTTGTCTTAG  T                                                                         108
```

( 2 ) INFORMATION FOR SEQ ID NO:4:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Thr  Arg  Pro  Pro  Thr  Cys  Cys  Cys  Phe  Met  Val  Phe  Pro  Gln  Glu  Gly
```

```
            1               5                    10                    15
Ser  His  Thr  His  Pro  Leu  Ser  Ser  Gln
                20                   25
```

(2) INFORMATION FOR SEQ ID NO:5:

(i) SEQUENCE CHARACTERISTICS:
    (A) LENGTH: 429 amino acids
    (B) TYPE: amino acid
    (C) STRANDEDNESS: single
    (D) TOPOLOGY: linear (ii) MOLECULE TYPE: protein (ix) FEATURE:
    (A) NAME/KEY: Region
    (B) LOCATION: 114..143
    (D) OTHER INFORMATION: /note= "Encompasses TM 4 of Figure 4"

(ix) FEATURE:
    (A) NAME/KEY: Region
    (B) LOCATION: 320..354
    (D) OTHER INFORMATION: /note= "Encompasses TM 9 of Figure 4"

(ix) FEATURE:
    (A) NAME/KEY: Region
    (B) LOCATION: 358..385
    (D) OTHER INFORMATION: /note= "Encompasses TM 10 of Figure 4"

(xi) SEQUENCE DESCRIPTION: SEQ ID NO:5:

```
Met  Thr  Arg  Arg  Ala  Ile  Gly  Val  Ser  Glu  Arg  Pro  Pro  Leu  Leu  Gln
 1                      5                     10                         15

Thr  Ile  Pro  Leu  Ser  Leu  Gln  His  Leu  Phe  Ala  Met  Phe  Gly  Ala  Thr
                20                       25                    30

Val  Leu  Val  Pro  Val  Leu  Phe  His  Ile  Asn  Pro  Ala  Thr  Val  Leu  Leu
               35                   40                         45

Phe  Asn  Gly  Ile  Gly  Thr  Leu  Leu  Tyr  Leu  Phe  Ile  Cys  Lys  Gly  Lys
          50                       55                    60

Ile  Pro  Ala  Tyr  Leu  Gly  Ser  Ser  Phe  Ala  Phe  Ile  Ser  Pro  Val  Leu
 65                      70                    75                         80

Leu  Leu  Leu  Pro  Leu  Gly  Tyr  Glu  Val  Ala  Leu  Gly  Gly  Phe  Ile  Met
               85                        90                         95

Cys  Gly  Val  Leu  Phe  Cys  Leu  Val  Ser  Phe  Ile  Val  Lys  Lys  Ala  Gly
              100                       105                   110

Thr  Gly  Trp  Leu  Asp  Val  Leu  Phe  Pro  Pro  Ala  Ala  Met  Gly  Ala  Ile
              115                       120                   125

Val  Ala  Val  Ile  Gly  Leu  Glu  Leu  Ala  Gly  Val  Ala  Ala  Gly  Met  Ala
         130                       135                   140

Gly  Leu  Leu  Pro  Ala  Glu  Gly  Gln  Thr  Pro  Asp  Ser  Lys  Thr  Ile  Ile
145                      150                   155                       160

Ile  Ser  Ile  Thr  Thr  Leu  Ala  Val  Thr  Val  Leu  Gly  Ser  Val  Leu  Phe
                   165                   170                        175

Arg  Gly  Phe  Leu  Ala  Ile  Ile  Pro  Ile  Leu  Ile  Gly  Val  Leu  Val  Gly
               180                   185                        190

Tyr  Ala  Leu  Ser  Phe  Ala  Met  Gly  Ile  Val  Asp  Thr  Thr  Pro  Ile  Ile
          195                  200                   205

Asn  Ala  His  Trp  Phe  Ala  Leu  Pro  Thr  Leu  Tyr  Thr  Pro  Arg  Phe  Glu
         210                       215                   220

Trp  Phe  Ala  Ile  Leu  Thr  Ile  Leu  Pro  Ala  Ala  Leu  Val  Val  Ile  Ala
225                      230                        235                  240
```

|     |     |     |     |     |     |     |     |     |     |     |     |     |     |     |
|-----|-----|-----|-----|-----|-----|-----|-----|-----|-----|-----|-----|-----|-----|-----|
| Glu | His | Val | Gly | His | Leu | Val | Val | Thr | Ala | Asn | Ile | Val | Lys | Lys | Asp |
|     |     |     |     | 245 |     |     |     |     | 250 |     |     |     |     | 255 |
| Leu | Leu | Arg | Asp | Pro | Gly | Leu | His | Arg | Ser | Met | Phe | Ala | Asn | Gly | Leu |
|     |     |     | 260 |     |     |     |     | 265 |     |     |     |     | 270 |     |
| Ser | Thr | Val | Ile | Ser | Gly | Phe | Phe | Gly | Ser | Thr | Pro | Asn | Thr | Thr | Tyr |
|     |     | 275 |     |     |     |     | 280 |     |     |     |     | 285 |     |     |
| Gly | Glu | Asn | Ile | Gly | Val | Met | Ala | Ile | Thr | Arg | Val | Tyr | Ser | Thr | Trp |
|     | 290 |     |     |     |     | 295 |     |     |     |     | 300 |     |     |     |
| Val | Ile | Gly | Gly | Ala | Ala | Ile | Phe | Ala | Ile | Leu | Leu | Ser | Cys | Val | Gly |
| 305 |     |     |     |     | 310 |     |     |     |     | 315 |     |     |     |     | 320 |
| Lys | Leu | Ala | Ala | Ala | Ile | Gln | Met | Ile | Pro | Leu | Pro | Val | Met | Gly | Gly |
|     |     |     |     | 325 |     |     |     |     | 330 |     |     |     |     | 335 |     |
| Val | Ser | Leu | Leu | Leu | Tyr | Gly | Val | Ile | Gly | Ala | Ser | Gly | Ile | Arg | Val |
|     |     |     | 340 |     |     |     |     | 345 |     |     |     |     | 350 |     |     |
| Leu | Ile | Glu | Ser | Lys | Val | Asp | Tyr | Asn | Lys | Ala | Gln | Asn | Leu | Ile | Leu |
|     |     | 355 |     |     |     |     | 360 |     |     |     |     | 365 |     |     |     |
| Thr | Ser | Val | Ile | Leu | Ile | Ile | Gly | Val | Ser | Gly | Ala | Lys | Val | Asn | Ile |
|     | 370 |     |     |     |     | 375 |     |     |     |     | 380 |     |     |     |     |
| Gly | Ala | Ala | Glu | Leu | Lys | Gly | Met | Ala | Leu | Ala | Thr | Ile | Val | Gly | Ile |
| 385 |     |     |     |     | 390 |     |     |     |     | 395 |     |     |     |     | 400 |
| Gly | Leu | Ser | Leu | Ile | Phe | Lys | Leu | Ile | Ser | Val | Leu | Arg | Pro | Glu | Glu |
|     |     |     |     | 405 |     |     |     |     | 410 |     |     |     |     | 415 |     |
| Val | Val | Leu | Asp | Ala | Glu | Asp | Ala | Asp | Ile | Thr | Asp | Lys |     |     |     |
|     |     |     | 420 |     |     |     |     | 425 |     |     |     |     |     |     |     |

( 2 ) INFORMATION FOR SEQ ID NO:6:

( i ) SEQUENCE CHARACTERISTICS:
        ( A ) LENGTH: 463 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Region
        ( B ) LOCATION: 151..180
        ( D ) OTHER INFORMATION: /note= "Encompasses TM 4 of Figure
            4"

( i x ) FEATURE:
        ( A ) NAME/KEY: Region
        ( B ) LOCATION: 366..428
        ( D ) OTHER INFORMATION: /note= "Encompasses TM 9 and TM 10
            of Figure 4"

( x i ) SEQUENCE DESCRIPTION: SEQ ID NO:6:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Ser | Val | Ser | Thr | Leu | Glu | Ser | Glu | Asn | Ala | Gln | Pro | Val | Ala | Gln |
| 1   |     |     |     | 5   |     |     |     |     | 10  |     |     |     |     | 15  |     |
| Thr | Gln | Asn | Ser | Glu | Leu | Ile | Tyr | Arg | Leu | Glu | Asp | Arg | Pro | Pro | Leu |
|     |     |     | 20  |     |     |     |     | 25  |     |     |     |     | 30  |     |     |
| Pro | Gln | Thr | Leu | Phe | Ala | Ala | Cys | Gln | His | Leu | Leu | Ala | Met | Phe | Val |
|     |     | 35  |     |     |     |     | 40  |     |     |     |     | 45  |     |     |     |
| Ala | Val | Ile | Thr | Pro | Ala | Leu | Leu | Ile | Cys | Gln | Ala | Leu | Gly | Leu | Pro |
|     | 50  |     |     |     |     | 55  |     |     |     |     | 60  |     |     |     |     |
| Ala | Gln | Asp | Thr | Gln | His | Ile | Ile | Ser | Met | Ser | Leu | Phe | Ala | Ser | Gly |
| 65  |     |     |     |     | 70  |     |     |     |     | 75  |     |     |     |     | 80  |
| Val | Ala | Ser | Ile | Ile | Gln | Ile | Lys | Ala | Trp | Gly | Pro | Val | Gly | Ser | Gly |
|     |     |     |     | 85  |     |     |     |     | 90  |     |     |     |     | 95  |     |

| | | | | | | | | | | | | | |
|---|---|---|---|---|---|---|---|---|---|---|---|---|---|
| Leu | Leu | Ser | Ile 100 | Gln | Gly | Thr | Ser | Phe 105 | Asn | Phe | Val | Ala | Pro 110 | Leu | Ile |
| Met | Gly | Gly 115 | Thr | Ala | Leu | Lys | Thr 120 | Gly | Gly | Ala | Asp | Val 125 | Pro | Thr | Met |
| Met | Ala 130 | Ala | Leu | Phe | Gly | Thr 135 | Leu | Met | Leu | Ala | Ser 140 | Cys | Thr | Glu | Met |
| Val 145 | Ile | Ser | Arg | Val | Leu 150 | His | Leu | Ala | Arg | Arg 155 | Ile | Ile | Thr | Pro | Leu 160 |
| Val | Ser | Gly | Val | Val 165 | Val | Met | Ile | Ile | Gly 170 | Leu | Ser | Leu | Ile | Gln 175 | Val |
| Gly | Leu | Thr | Ser 180 | Ile | Gly | Gly | Gly | Tyr 185 | Ala | Ala | Met | Ser | Asp 190 | Asn | Thr |
| Phe | Gly | Ala 195 | Pro | Lys | Asn | Leu | Leu 200 | Leu | Ala | Gly | Val | Val 205 | Leu | Ala | Leu |
| Ile | Ile 210 | Leu | Leu | Asn | Arg | Gln 215 | Arg | Asn | Pro | Tyr | Leu 220 | Arg | Val | Ala | Ser |
| Leu 225 | Val | Ile | Ala | Met | Ala 230 | Ala | Gly | Tyr | Ala | Leu 235 | Ala | Trp | Phe | Met | Gly 240 |
| Met | Leu | Pro | Glu | Ser 245 | Asn | Glu | Pro | Met | Thr 250 | Gln | Glu | Leu | Ile | Met 255 | Val |
| Pro | Thr | Pro | Leu 260 | Tyr | Tyr | Gly | Leu | Gly 265 | Ile | Glu | Trp | Ser | Leu 270 | Leu | Leu |
| Pro | Leu | Met 275 | Leu | Val | Phe | Met | Ile 280 | Thr | Ser | Leu | Glu | Thr 285 | Ile | Gly | Asp |
| Ile | Thr 290 | Ala | Thr | Ser | Asp | Val 295 | Ser | Glu | Gln | Pro | Val 300 | Ser | Gly | Pro | Leu |
| Tyr 305 | Met | Lys | Arg | Leu | Lys 310 | Gly | Gly | Val | Leu | Ala 315 | Asn | Gly | Leu | Asn | Ser 320 |
| Phe | Val | Ser | Ala | Val 325 | Phe | Asn | Thr | Phe | Pro 330 | Asn | Ser | Cys | Phe | Gly 335 | Gln |
| Asn | Asn | Gly | Val 340 | Ile | Gln | Leu | Thr | Gly 345 | Val | Ala | Ser | Arg | Tyr 350 | Val | Gly |
| Phe | Val | Val 355 | Ala | Leu | Met | Leu | Ile 360 | Val | Leu | Gly | Leu | Phe 365 | Pro | Ala | Val |
| Ser | Gly 370 | Phe | Val | Gln | His | Ile 375 | Pro | Glu | Pro | Val | Leu 380 | Gly | Gly | Ala | Thr |
| Leu 385 | Val | Met | Phe | Gly | Thr 390 | Ile | Ala | Ala | Ser | Gly 395 | Val | Arg | Ile | Val | Ser 400 |
| Arg | Glu | Pro | Leu | Asn 405 | Arg | Arg | Ala | Ile | Leu 410 | Ile | Ile | Ala | Leu | Ser 415 | Leu |
| Ala | Val | Gly | Leu 420 | Gly | Val | Ser | Gln | Gln 425 | Pro | Leu | Ile | Leu | Gln 430 | Phe | Ala |
| Pro | Glu | Trp 435 | Leu | Lys | Asn | Leu | Leu 440 | Ser | Ser | Gly | Ile | Ala 445 | Ala | Gly | Gly |
| Ile | Thr 450 | Ala | Ile | Val | Leu | Asn 455 | Leu | Ile | Phe | Pro | Pro 460 | Glu | Lys | Gln | |

( 2 ) INFORMATION FOR SEQ ID NO:7:

( i ) SEQUENCE CHARACTERISTICS:
        ( A ) LENGTH: 434 amino acids
        ( B ) TYPE: amino acid
        ( C ) STRANDEDNESS: single
        ( D ) TOPOLOGY: linear ( i i ) MOLECULE TYPE: protein ( i x ) FEATURE:
    ( A ) NAME/KEY: Region
    ( B ) LOCATION: 117..146
    ( D ) OTHER INFORMATION: /note= "Encompasses TM 4 of Figure 4"

( i x ) FEATURE:
    ( A ) NAME/KEY: Region
    ( B ) LOCATION: 330..364
    ( D ) OTHER INFORMATION: /note= "Encompasses TM 9 of Figure 4"

( i x ) FEATURE:
    ( A ) NAME/KEY: Region
    ( B ) LOCATION: 368..395
    ( D ) OTHER INFORMATION: /note= "Encompasses TM 10 of Figure 4"

( x i ) SEQUENCE DESCRIPTION: SEQ ID NO:7:

```
Met Ser Lys Lys Lys Val Asn Leu Gly Val Arg Asp Val Pro Thr Pro
 1               5                  10                 15
Phe Ser Trp Val Ser Phe Ser Leu Gln His Leu Phe Ala Met Phe Gly
            20                  25                  30
Ser Thr Ile Leu Val Pro Lys Leu Val Gly Met Ser Pro Ala Val Ala
        35                  40                  45
Leu Val Thr Ser Gly Ile Gly Thr Leu Ala Tyr Leu Leu Ile Thr Lys
    50                  55                  60
Gly Gln Ile Pro Ala Tyr Leu Gly Ser Ser Phe Ala Phe Ile Ser Pro
65                  70                  75                  80
Ile Ile Leu Val Lys Ala Thr Gly Gly Pro Gly Ala Ala Met Val Gly
                85                  90                  95
Ala Phe Leu Ala Gly Leu Val Tyr Gly Leu Ile Ala Leu Leu Ile Arg
            100                 105                 110
Gln Leu Gly Thr Gly Trp Leu Met Lys Ile Leu Pro Pro Val Val Val
            115                 120                 125
Gly Pro Val Ile Ile Val Ile Gly Leu Gly Leu Ala Ser Thr Ala Val
    130                 135                 140
Asn Met Ala Met Tyr Ala Asp Pro Asn Ala Ser Glu Leu Val Tyr Ser
145                 150                 155                 160
Leu Lys His Phe Ser Val Ala Gly Val Thr Leu Ala Ile Thr Ile Ile
                165                 170                 175
Cys Ala Ile Phe Leu Arg Gly Phe Leu Ser Leu Ile Pro Val Leu Ile
            180                 185                 190
Gly Ile Ile Gly Gly Tyr Leu Phe Ala Leu Thr Gln Gly Ile Val Asn
        195                 200                 205
Phe Gln Pro Val Leu Asp Ala Lys Trp Phe Ala Val Pro Glu Phe Ile
    210                 215                 220
Ile Pro Phe Lys Asp Tyr His Arg Gln Leu Arg Ser Ala Ser Gln Pro
225                 230                 235                 240
Gln Trp Phe Leu Ser His Leu Ser Gln Cys Gln Ser Ile Ser Ala Thr
                245                 250                 255
Asn Gly Ala Glu Ser Lys Val Val Gly Gln Asp Phe Ile Lys Ala Gly
            260                 265                 270
Leu His Arg Ser Ile Met Gly Asp Ser Val Ala Thr Ile Leu Ala Ser
        275                 280                 285
Leu Ile Gly Gly Pro Pro Thr Thr Thr Tyr Gly Glu Asn Ile Gly Val
    290                 295                 300
Leu Ala Ile Thr Arg Val Phe Ser Val Phe Val Ile Gly Gly Ala Ala
305                 310                 315                 320
```

-continued

| | | | | | | | | | | | | | | |
|---|---|---|---|---|---|---|---|---|---|---|---|---|---|---|
| Val | Ile | Ala | Leu | Cys<br>325 | Phe | Gly | Phe | Ile<br>330 | Gly | Lys | Ile | Ser | Ala | Leu<br>335 | Ile |
| Ser | Ser | Val | Pro<br>340 | Ser | Ala | Val | Met | Gly<br>345 | Gly | Val | Ser | Phe | Leu<br>350 | Leu | Phe |
| Gly | Ile | Ile<br>355 | Ala | Ser | Ser | Gly | Leu<br>360 | Arg | Met | Leu | Ile | Asp<br>365 | Asn | Lys | Ile |
| Asp | Tyr<br>370 | Glu | Asn | Asn | Arg | Asn<br>375 | Leu | Ile | Ile | Thr | Ser<br>380 | Val | Ile | Leu | Val |
| Ile<br>385 | Gly | Val | Gly | Gly | Ala<br>390 | Phe | Ile | Gln | Val | Ser<br>395 | Gln | Gly | Gly | Phe | Gln<br>400 |
| Val | Ser | Gly | Met | Ala<br>405 | Leu | Ala | Ala | Ile | Val<br>410 | Gly | Val | Ile | Leu | Asn<br>415 | Leu |
| Ile | Leu | Pro | Gln<br>420 | Ala | Lys | Glu | Glu | Gln<br>425 | Ala | Asp | Thr | Ser | Glu<br>430 | Gln | His |
| His | Ile | | | | | | | | | | | | | | |

( 2 ) INFORMATION FOR SEQ ID NO:8:

( i ) SEQUENCE CHARACTERISTICS:
        ( A ) LENGTH: 432 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Region
        ( B ) LOCATION: 115..144
        ( D ) OTHER INFORMATION: /note= "Encompasses TM 4 of Figure
            4"

( i x ) FEATURE:
        ( A ) NAME/KEY: Region
        ( B ) LOCATION: 325..359
        ( D ) OTHER INFORMATION: /note= "Encompasses TM 9 of Figure
            4"

( i x ) FEATURE:
        ( A ) NAME/KEY: Region
        ( B ) LOCATION: 363..390
        ( D ) OTHER INFORMATION: /note= "Encompasses TM 10 of Figure
            4"

( x i ) SEQUENCE DESCRIPTION: SEQ ID NO:8:

| | | | | | | | | | | | | | | |
|---|---|---|---|---|---|---|---|---|---|---|---|---|---|---|
| Met<br>1 | Asn | Lys | Pro | Val<br>5 | Leu | Asp | Ile | Gln | Asp<br>10 | Arg | Pro | Thr | Val | Gly<br>15 | Gln |
| Trp | Ile | Thr | Leu<br>20 | Ser | Leu | Gln | His | Leu<br>25 | Phe | Ala | Met | Phe | Gly<br>30 | Ala | Thr |
| Ile | Leu | Val<br>35 | Pro | Tyr | Leu | Val | Gly<br>40 | Leu | Asp | Pro | Ser | Ile<br>45 | Ala | Leu | Leu |
| Thr | Ser<br>50 | Gly | Leu | Gly | Thr | Leu<br>55 | Ala | Phe | Leu | Leu | Ile<br>60 | Thr | Lys | Trp | Gln |
| Val<br>65 | Pro | Ala | Tyr | Leu | Gly<br>70 | Ser | Ser | Phe | Ala | Tyr<br>75 | Ile | Ala | Pro | Ile | Ile<br>80 |
| Ala | Ala | Lys | Thr | Ala<br>85 | Gly | Gly | Pro | Gly | Ala<br>90 | Ala | Met | Ile | Gly | Ser<br>95 | Phe |
| Leu | Ala | Gly | Leu<br>100 | Val | Tyr | Gly | Val | Val<br>105 | Ala | Leu | Ile | Ile | Lys<br>110 | Lys | Ala |
| Gly | Tyr | Arg<br>115 | Trp | Val | Met | Lys | Leu<br>120 | Leu | Pro | Pro | Val | Val<br>125 | Gly | Gly | Pro |
| Val | Ile<br>130 | Ile | Val | Ile | Gly | Leu<br>135 | Gly | Leu | Ala | Gly | Thr<br>140 | Ala | Val | Gly | Met |

```
Ala  Met  Asn  Gly  Pro  Asp  Gly  Lys  Tyr  Ser  Leu  Leu  His  Phe  Ser  Val
145            150                      155                      160

Ala  Leu  Val  Thr  Leu  Ala  Ala  Thr  Ile  Val  Cys  Ser  Val  Leu  Ala  Arg
               165                 170                      175

Gly  Met  Leu  Ser  Leu  Ile  Pro  Val  Leu  Val  Gly  Ile  Val  Val  Gly  Tyr
               180                 185                      190

Leu  Tyr  Ala  Leu  Ala  Val  Gly  Leu  Val  Asp  Leu  Ser  Lys  Val  Ala  Ala
          195                 200                      205

Ala  Lys  Trp  Phe  Glu  Trp  Pro  Asp  Phe  Leu  Ile  Pro  Phe  Ala  Asp  Tyr
          210                 215                      220

Pro  Val  Arg  Val  Thr  Trp  Glu  Ile  Val  Met  Leu  Met  Val  Pro  Val  Ala
225                 230                      235                           240

Ile  Val  Thr  Leu  Ser  Glu  His  Ile  Gly  His  Gln  Leu  Val  Leu  Ser  Lys
               245                      250                           255

Val  Val  Gly  Arg  Asp  Leu  Ile  Gln  Lys  Pro  Gly  Leu  His  Arg  Ser  Ile
               260                 265                      270

Leu  Gly  Asp  Gly  Thr  Ala  Thr  Met  Ile  Ser  Ala  Leu  Leu  Gly  Gly  Pro
          275                 280                      285

Pro  Lys  Thr  Thr  Tyr  Gly  Glu  Asn  Ile  Gly  Val  Leu  Ala  Ile  Thr  Arg
     290                 295                      300

Val  Tyr  Ser  Val  Tyr  Val  Leu  Ala  Gly  Ala  Ala  Val  Ile  Ala  Ile  Ala
305                 310                      315                           320

Phe  Gly  Phe  Val  Gly  Lys  Ile  Thr  Ala  Leu  Ile  Ser  Ser  Ile  Pro  Thr
                    325                 330                      335

Pro  Val  Met  Gly  Gly  Val  Ser  Ile  Leu  Leu  Phe  Gly  Ile  Ile  Ala  Ser
               340                 345                      350

Ser  Gly  Leu  Arg  Met  Leu  Ile  Asp  Ser  Arg  Val  Asp  Phe  Gly  Gln  Thr
               355                 360                      365

Arg  Asn  Leu  Val  Ile  Ala  Ser  Val  Ile  Leu  Val  Ile  Gly  Ile  Gly  Gly
     370                 375                      380

Ala  Val  Leu  Lys  Ile  Ser  Asp  Ser  Phe  Gln  Ile  Thr  Gly  Met  Ala  Leu
385                 390                      395                           400

Ser  Ala  Ile  Val  Gly  Val  Leu  Leu  Asn  Leu  Ile  Leu  Pro  Gly  Arg  Pro
                    405                 410                      415

Gln  Ala  Ala  Glu  Asn  Leu  Phe  Glu  Glu  Asn  Gln  Ser  Asp  His  Val  Ala
               420                 425                      430
```

( 2 ) INFORMATION FOR SEQ ID NO:9:

( i ) SEQUENCE CHARACTERISTICS:
        ( A ) LENGTH: 438 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Region
        ( B ) LOCATION: 115..144
        ( D ) OTHER INFORMATION: /note= "Encompasses TM 4 of Figure 4"

( i x ) FEATURE:
        ( A ) NAME/KEY: Region
        ( B ) LOCATION: 323..357
        ( D ) OTHER INFORMATION: /note= "Encompasses TM 9 of Figure 4"

( i x ) FEATURE:
        ( A ) NAME/KEY: Region (B) LOCATION: 359..386
(D) OTHER INFORMATION: /note= "Encompasses TM 10 of Figure 4"

(xi) SEQUENCE DESCRIPTION: SEQ ID NO:9:

| Met | Arg | Asn | Gly | Phe | Gly | Lys | Thr | Leu | Ser | Leu | Gly | Ile | Gln | His | Val |
|---|---|---|---|---|---|---|---|---|---|---|---|---|---|---|---|
| 1 | | | | 5 | | | | | 10 | | | | | 15 | |
| Leu | Ala | Met | Tyr | Ala | Gly | Ala | Ile | Val | Val | Pro | Leu | Ile | Val | Gly | Lys |
| | | | 20 | | | | 25 | | | | | 30 | | | |
| Ala | Met | Gly | Leu | Thr | Val | Glu | Gln | Leu | Thr | Tyr | Leu | Val | Ser | Ile | Asp |
| | | 35 | | | | | 40 | | | | | 45 | | | |
| Ile | Phe | Met | Cys | Gly | Val | Ala | Thr | Leu | Leu | Gln | Val | Trp | Ser | Asn | Arg |
| | 50 | | | | | 55 | | | | | 60 | | | | |
| Phe | Phe | Gly | Ile | Gly | Leu | Pro | Val | Val | Leu | Gly | Cys | Thr | Phe | Thr | Ala |
| 65 | | | | | 70 | | | | | 75 | | | | | 80 |
| Val | Ser | Pro | Met | Ile | Ala | Ile | Gly | Ser | Glu | Tyr | Gly | Val | Ser | Thr | Val |
| | | | | 85 | | | | | 90 | | | | | 95 | |
| Tyr | Gly | Ser | Ile | Ile | Ala | Ser | Gly | Ile | Leu | Val | Ile | Leu | Ile | Ser | Phe |
| | | | 100 | | | | | 105 | | | | | 110 | | |
| Phe | Phe | Gly | Lys | Leu | Val | Ser | Phe | Phe | Pro | Val | Val | Thr | Gly | Ser |
| | | 115 | | | | | 120 | | | | | 125 | | | |
| Val | Val | Thr | Ile | Ile | Gly | Ile | Thr | Leu | Met | Pro | Val | Ala | Met | Asn | Asn |
| | 130 | | | | | 135 | | | | | 140 | | | | |
| Met | Ala | Gly | Gly | Glu | Gly | Ser | Ala | Asp | Phe | Gly | Asp | Leu | Ser | Asn | Leu |
| 145 | | | | | 150 | | | | | 155 | | | | | 160 |
| Ala | Leu | Ala | Phe | Thr | Val | Leu | Ser | Ile | Ile | Val | Leu | Leu | Tyr | Arg | Phe |
| | | | | 165 | | | | | 170 | | | | | 175 | |
| Thr | Lys | Gly | Phe | Ile | Lys | Ser | Val | Ser | Ile | Leu | Ile | Gly | Ile | Leu | Ile |
| | | | 180 | | | | | 185 | | | | | 190 | | |
| Gly | Thr | Phe | Ile | Ala | Tyr | Phe | Met | Gly | Lys | Val | Gln | Phe | Asp | Asn | Val |
| | | 195 | | | | | 200 | | | | | 205 | | | |
| Ser | Asp | Ala | Ala | Val | Val | Gln | Met | Ile | Gln | Pro | Phe | Tyr | Phe | Gly | Ala |
| | 210 | | | | | 215 | | | | | 220 | | | | |
| Pro | Ser | Phe | His | Ala | Ala | Pro | Ile | Ile | Thr | Met | Ser | Ile | Val | Ala | Ile |
| 225 | | | | | 230 | | | | | 235 | | | | | 240 |
| Val | Ser | Leu | Val | Glu | Ser | Thr | Gly | Val | Tyr | Phe | Ala | Leu | Gly | Asp | Leu |
| | | | | 245 | | | | | 250 | | | | | 255 | |
| Thr | Asn | Arg | Arg | Leu | Thr | Glu | Ile | Asp | Leu | Ser | Lys | Gly | Tyr | Arg | Ala |
| | | | 260 | | | | | 265 | | | | | 270 | | |
| Glu | Gly | Leu | Ala | Val | Leu | Leu | Gly | Gly | Ile | Phe | Asn | Ala | Phe | Pro | Tyr |
| | | 275 | | | | | 280 | | | | | 285 | | | |
| Thr | Ala | Phe | Ser | Gln | Asn | Val | Gly | Leu | Val | Gln | Leu | Thr | Gly | Ile | Lys |
| | 290 | | | | | 295 | | | | | 300 | | | | |
| Lys | Asn | Ala | Val | Ile | Val | Val | Thr | Gly | Val | Ile | Leu | Met | Ala | Phe | Gly |
| 305 | | | | | 310 | | | | | 315 | | | | | 320 |
| Leu | Phe | Pro | Lys | Ile | Ala | Ala | Phe | Thr | Thr | Ile | Ile | Pro | Ser | Ala | Val |
| | | | | 325 | | | | | 330 | | | | | 335 | |
| Leu | Gly | Gly | Ala | Met | Val | Ala | Met | Phe | Gly | Met | Val | Ile | Ala | Tyr | Gly |
| | | | 340 | | | | | 345 | | | | | 350 | | |
| Ile | Lys | Met | Leu | Ser | Arg | Ile | Asp | Phe | Ala | Lys | Gln | Glu | Asn | Leu | Leu |
| | | 355 | | | | | 360 | | | | | 365 | | | |
| Ile | Val | Ala | Cys | Ser | Val | Gly | Leu | Gly | Leu | Gly | Val | Thr | Val | Val | Pro |
| | 370 | | | | | 375 | | | | | 380 | | | | |
| Asp | Ile | Phe | Lys | Gln | Leu | Pro | Ser | Ala | Leu | Thr | Leu | Leu | Thr | Thr | Asn |
| 385 | | | | | 390 | | | | | 395 | | | | | 400 |

```
Gly  Ile  Val  Ala  Gly  Ser  Phe  Thr  Ala  Val  Val  Leu  Asn  Ile  Val  Tyr
               405                      410                          415

Asn  Val  Phe  Ser  Lys  Ala  Lys  Lys  Ile  Glu  Gln  Glu  Ala  Asp  Leu  Ala
               420                      425                     430

Glu  Gln  Lys  Thr  Ala  Val
               435
```

( 2 ) INFORMATION FOR SEQ ID NO:10:

( i ) SEQUENCE CHARACTERISTICS:
        ( A ) LENGTH: 460 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Region
        ( B ) LOCATION: 117..149
        ( D ) OTHER INFORMATION: /note= "Encompasses TM 4 of Figure 4"

( i x ) FEATURE:
        ( A ) NAME/KEY: Region
        ( B ) LOCATION: 328..362
        ( D ) OTHER INFORMATION: /note= "Encompasses TM 9 of Figure 4"

( i x ) FEATURE:
        ( A ) NAME/KEY: Region
        ( B ) LOCATION: 365..392
        ( D ) OTHER INFORMATION: /note= "Encompasses TM 10 of Figure 4"

( x i ) SEQUENCE DESCRIPTION: SEQ ID NO:10:

```
Met  Lys  Leu  Val  Leu  Gly  Ala  Leu  Gln  Trp  Thr  Ala  Phe  Ile  Ile  Ala
 1                  5                        10                          15

Ala  Ala  Ile  Val  Val  Pro  Val  Ala  Val  Ala  Gln  Ser  Phe  His  Leu  Asp
               20                       25                          30

His  Ser  Asp  Ser  Ala  Arg  Leu  Ile  Gln  Ser  Thr  Phe  Phe  Val  Leu  Gly
          35                        40                      45

Ile  Ala  Ala  Val  Ile  Gln  Cys  Leu  Lys  Gly  His  Arg  Leu  Pro  Ile  Asn
     50                       55                      60

Glu  Ser  Pro  Ala  Gly  Leu  Trp  Trp  Gly  Val  Tyr  Thr  Ile  Tyr  Ala  Gly
65                       70                      75                           80

Leu  Thr  Gly  Thr  Val  Phe  Ala  Thr  Tyr  Gly  Asp  Thr  Leu  Arg  Gly  Leu
               85                       90                          95

Gln  Gly  Ala  Leu  Leu  Val  Ser  Ala  Val  Cys  Phe  Phe  Leu  Leu  Ser  Val
               100                      105                         110

Phe  Lys  Val  Ile  Asp  Arg  Leu  Ala  Lys  Leu  Phe  Thr  Pro  Val  Val  Thr
          115                       120                     125

Gly  Val  Tyr  Leu  Leu  Leu  Leu  Val  Met  Gln  Leu  Ser  Gln  Pro  Ile  Ile
     130                      135                      140

Lys  Gly  Ile  Leu  Gly  Ile  Gly  Tyr  Arg  Gln  Asp  Gly  Val  Asp  Gly  Leu
145                       150                     155                          160

Val  Phe  Gly  Leu  Ala  Leu  Val  Val  Ile  Ala  Ala  Phe  Ile  Met  Thr
                    165                      170                     175

Asn  Ser  Asn  Ile  Met  Phe  Phe  Lys  Gln  Tyr  Ser  Ile  Leu  Leu  Ala  Leu
               180                      185                         190

Phe  Gly  Gly  Trp  Val  Leu  Phe  Ala  Ala  Ala  Gly  Ala  Ala  Lys  Pro  Ile
               195                      200                         205
```

| Glu | Met | Pro | Asp | Arg | Leu | Phe | Gln | Leu | Pro | Ser | Leu | Phe | Pro | Phe | Gly |
|---|---|---|---|---|---|---|---|---|---|---|---|---|---|---|---|
| | 210 | | | | | 215 | | | | 220 | | | | | |

| Thr | Pro | Leu | Phe | Asn | Ser | Gly | Leu | Ile | Ile | Thr | Ser | Ile | Phe | Ile | Thr |
|---|---|---|---|---|---|---|---|---|---|---|---|---|---|---|---|
| 225 | | | | | 230 | | | | | 235 | | | | | 240 |

| Ile | Leu | Leu | Ile | Val | Asn | Met | Leu | Ala | Ser | Met | Lys | Val | Val | Asp | Ile |
|---|---|---|---|---|---|---|---|---|---|---|---|---|---|---|---|
| | | | | 245 | | | | | 250 | | | | | 255 | |

| Ala | Met | Lys | Lys | Phe | Ser | Lys | Gln | Pro | Asp | Gly | Lys | His | His | Glu | Arg |
|---|---|---|---|---|---|---|---|---|---|---|---|---|---|---|---|
| | | | 260 | | | | | 265 | | | | | 270 | | |

| His | Ala | Gly | Phe | Ala | Ala | Ser | Phe | Ser | His | Leu | Leu | Ser | Gly | Leu | Thr |
|---|---|---|---|---|---|---|---|---|---|---|---|---|---|---|---|
| | | 275 | | | | | 280 | | | | | 285 | | | |

| Gly | Ala | Ile | Ala | Pro | Val | Pro | Ile | Ser | Gly | Ala | Ala | Gly | Phe | Ile | Glu |
|---|---|---|---|---|---|---|---|---|---|---|---|---|---|---|---|
| | 290 | | | | | 295 | | | | | 300 | | | | |

| Thr | Thr | Lys | Met | Pro | Ser | Lys | Lys | Pro | Phe | Met | Leu | Gly | Ser | Ile | Leu |
|---|---|---|---|---|---|---|---|---|---|---|---|---|---|---|---|
| 305 | | | | | 310 | | | | | 315 | | | | | 320 |

| Val | Ile | Val | Ile | Ser | Val | Ile | Pro | Phe | Phe | Met | Asn | Thr | Phe | Ala | Ser |
|---|---|---|---|---|---|---|---|---|---|---|---|---|---|---|---|
| | | | | 325 | | | | | 330 | | | | | 335 | |

| Leu | Pro | Ser | Pro | Val | Gly | Phe | Ala | Val | Asn | Phe | Val | Val | Phe | Ser | Ala |
|---|---|---|---|---|---|---|---|---|---|---|---|---|---|---|---|
| | | | 340 | | | | | 345 | | | | | 350 | | |

| Met | Gly | Gly | Leu | Ala | Phe | Ala | Glu | Phe | Asp | Ser | Tyr | Glu | Lys | Glu | Glu |
|---|---|---|---|---|---|---|---|---|---|---|---|---|---|---|---|
| | | 355 | | | | | 360 | | | | | 365 | | | |

| Ser | Lys | Arg | Val | Arg | Ser | Ile | Ile | Gly | Ile | Ser | Leu | Leu | Thr | Gly | Val |
|---|---|---|---|---|---|---|---|---|---|---|---|---|---|---|---|
| | 370 | | | | | 375 | | | | | 380 | | | | |

| Gly | Ile | Met | Phe | Val | Pro | Glu | Thr | Ala | Leu | Lys | Gly | Leu | His | Pro | Val |
|---|---|---|---|---|---|---|---|---|---|---|---|---|---|---|---|
| 385 | | | | | 390 | | | | | 395 | | | | | 400 |

| Phe | Ile | Ser | Leu | Leu | Ser | Asn | Gly | Leu | Val | Leu | Gly | Thr | Leu | Ala | Ala |
|---|---|---|---|---|---|---|---|---|---|---|---|---|---|---|---|
| | | | | 405 | | | | | 410 | | | | | 415 | |

| Ile | Ala | Ala | Asp | Gln | Phe | Gln | Leu | Trp | Arg | Arg | Arg | Asn | Pro | Thr | Ile |
|---|---|---|---|---|---|---|---|---|---|---|---|---|---|---|---|
| | | | 420 | | | | | 425 | | | | | 430 | | |

| Ser | Cys | Gln | Arg | Arg | Thr | Asn | Ile | Glu | Phe | Trp | Cys | Arg | Cys | Asp | Lys |
|---|---|---|---|---|---|---|---|---|---|---|---|---|---|---|---|
| | | 435 | | | | | 440 | | | | | 445 | | | |

| Ile | Asn | Asp | Met | Ser | Leu | Thr | Lys | Arg | Arg | Glu | Arg |
|---|---|---|---|---|---|---|---|---|---|---|---|
| | 450 | | | | | 455 | | | | 460 | |

( 2 ) INFORMATION FOR SEQ ID NO:11:

( i ) SEQUENCE CHARACTERISTICS:
        ( A ) LENGTH: 595 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Region
        ( B ) LOCATION: 233..262
        ( D ) OTHER INFORMATION: /note= "Encompasses TM 4 of Figure
            4"

( i x ) FEATURE:
        ( A ) NAME/KEY: Region
        ( B ) LOCATION: 459..521
        ( D ) OTHER INFORMATION: /note= "Encompasses TM 9 and TM 10
            of Figure 4"

( x i ) SEQUENCE DESCRIPTION: SEQ ID NO:11:

| Met | Val | Ile | Phe | Leu | Leu | Lys | Leu | Arg | Asn | Lys | Ser | Asp | Cys | Asp | Ala |
|---|---|---|---|---|---|---|---|---|---|---|---|---|---|---|---|
| 1 | | | | 5 | | | | | 10 | | | | | 15 | |

| Ser | Met | Ile | Gly | Pro | Gly | Leu | Asp | His | Ser | Pro | Ala | Pro | Ala | Val | Gly |
|---|---|---|---|---|---|---|---|---|---|---|---|---|---|---|---|
| | | | 20 | | | | | 25 | | | | | 30 | | |

| Pro | Asp | Pro | Tyr | Ser | Ser | Asp | Ser | Met | Asp | Asn | Ser | Ile | His | Ser | Thr |

|   |   |   | 35 |   |   |   | 40 |   |   |   | 45 |   |   |   |
|---|---|---|---|---|---|---|---|---|---|---|---|---|---|---|
| Asp | Gly | Pro | Asp | Ser | Val | Ile | Pro | Asn | Ser | Asn | Pro | Lys | Lys | Thr | Val |
|   |   | 50 |   |   |   |   | 55 |   |   |   | 60 |   |   |   |
| Arg | Gln | Arg | Val | Arg | Leu | Leu | Ala | Arg | His | Leu | Thr | Thr | Arg | Glu | Gly |
| 65 |   |   |   |   | 70 |   |   |   | 75 |   |   |   |   |   | 80 |
| Leu | Ile | His | Gly | Arg | Arg | Leu | Phe | Leu | Ala | Ser | Thr | Arg | Arg | Phe | Pro |
|   |   |   |   | 85 |   |   |   |   | 90 |   |   |   |   | 95 |   |
| Cys | Cys | Trp | Arg | Leu | Ser | Trp | Val | Phe | Ser | Met | Arg | Leu | Pro | Cys | Trp |
|   |   |   | 100 |   |   |   | 105 |   |   |   |   |   | 110 |   |   |
| Ala | Gly | Val | Val | Thr | Pro | Pro | Leu | Ile | Ile | Ser | Ser | Leu | Ser | Leu |
|   |   |   | 115 |   |   |   | 120 |   |   |   |   | 125 |   |   |
| Pro | Ser | Asp | Leu | Gln | Gln | Tyr | Leu | Val | Ser | Thr | Ser | Leu | Ile | Val | Cys |
|   |   | 130 |   |   |   |   | 135 |   |   |   | 140 |   |   |   |
| Gly | Leu | Leu | Ser | Met | Val | Gln | Ile | Thr | Arg | Phe | His | Ile | Tyr | Lys | Thr |
| 145 |   |   |   |   | 150 |   |   |   |   | 155 |   |   |   |   | 160 |
| Pro | Tyr | Tyr | Ile | Gly | Ser | Gly | Val | Leu | Ser | Val | Met | Gly | Val | Ser | Phe |
|   |   |   |   | 165 |   |   |   |   | 170 |   |   |   |   | 175 |   |
| Ser | Ile | Ile | Ser | Val | Ala | Ser | Gly | Pro | Phe | Asn | Gln | Met | Tyr | Ser | Asn |
|   |   |   | 180 |   |   |   | 185 |   |   |   |   |   | 190 |   |   |
| Gly | Phe | Cys | Gln | Leu | Asp | Glu | Ala | Gly | Asn | Arg | Leu | Pro | Cys | Pro | Glu |
|   |   | 195 |   |   |   |   | 200 |   |   |   | 205 |   |   |   |
| Ala | Tyr | Ala | Ala | Leu | Val | Gly | Thr | Ser | Ala | Cys | Cys | Ala | Leu | Val | Glu |
|   | 210 |   |   |   |   | 215 |   |   |   |   | 220 |   |   |   |
| Ile | Leu | Leu | Ala | Phe | Val | Pro | Pro | Lys | Val | Ile | Gln | Lys | Ile | Phe | Pro |
| 225 |   |   |   |   | 230 |   |   |   |   | 235 |   |   |   |   | 240 |
| Pro | Ile | Val | Thr | Gly | Pro | Thr | Val | Met | Leu | Ile | Gly | Ile | Ser | Leu | Ile |
|   |   |   |   | 245 |   |   |   |   | 250 |   |   |   |   | 255 |   |
| Gly | Thr | Gly | Phe | Lys | Asp | Trp | Ala | Gly | Ser | Ala | Cys | Met | Asp | Asp |
|   |   |   | 260 |   |   |   | 265 |   |   |   |   |   | 270 |   |   |
| Gly | Met | Leu | Cys | Pro | Ser | Ala | Thr | Ala | Pro | Arg | Pro | Leu | Pro | Trp | Gly |
|   |   | 275 |   |   |   |   | 280 |   |   |   | 285 |   |   |   |
| Ser | Pro | Glu | Phe | Ile | Gly | Leu | Gly | Phe | Leu | Val | Phe | Val | Ser | Ile | Ile |
|   | 290 |   |   |   |   | 295 |   |   |   |   | 300 |   |   |   |
| Leu | Cys | Glu | Arg | Phe | Gly | Ala | Pro | Val | Met | Lys | Ser | Cys | Ser | Val | Val |
| 305 |   |   |   |   | 310 |   |   |   |   | 315 |   |   |   |   | 320 |
| Ile | Gly | Leu | Leu | Val | Gly | Cys | Ile | Val | Ala | Ala | Cys | Gly | Tyr | Phe |
|   |   |   |   | 325 |   |   |   |   | 330 |   |   |   |   | 335 |   |
| Ser | His | Ala | Asp | Ile | Asp | Ala | Ala | Pro | Ala | Ala | Ser | Phe | Ile | Trp | Val |
|   |   |   | 340 |   |   |   | 345 |   |   |   |   |   | 350 |   |   |
| Lys | Thr | Phe | Pro | Leu | Ser | Val | Tyr | Gly | Pro | Met | Val | Leu | Pro | Ile | Ile |
|   |   | 355 |   |   |   |   | 360 |   |   |   | 365 |   |   |   |
| Ala | Val | Phe | Ile | Ile | Cys | Ala | Cys | Glu | Cys | Ile | Gly | Asp | Val | Thr | Ala |
|   | 370 |   |   |   |   | 375 |   |   |   |   | 380 |   |   |   |
| Thr | Cys | Asp | Val | Ser | Arg | Leu | Glu | Val | Arg | Gly | Gly | Thr | Phe | Glu | Ser |
| 385 |   |   |   |   | 390 |   |   |   |   | 395 |   |   |   |   | 400 |
| Arg | Ile | Gln | Gly | Ala | Val | Leu | Ala | Asp | Gly | Thr | Asn | Ser | Val | Val | Ala |
|   |   |   |   | 405 |   |   |   |   | 410 |   |   |   |   | 415 |   |
| Ala | Leu | Ala | Thr | Met | Thr | Pro | Met | Thr | Thr | Phe | Ala | Gln | Asn | Asn | Gly |
|   |   |   | 420 |   |   |   | 425 |   |   |   |   |   | 430 |   |   |
| Val | Ile | Ala | Leu | Thr | Pro | Cys | Ala | Asn | Arg | Trp | Ala | Gly | Tyr | Cys | Cys |
|   |   | 435 |   |   |   |   | 440 |   |   |   | 445 |   |   |   |
| Cys | Leu | Ile | Leu | Ile | Val | Ala | Gly | Ile | Phe | Ala | Lys | Phe | Ala | Ala | Ala |
|   | 450 |   |   |   |   | 455 |   |   |   |   | 460 |   |   |   |

-continued

```
Ile  Val  Ala  Ile  Pro  Asn  Ser  Val  Met  Gly  Gly  Met  Lys  Thr  Phe  Leu
465                      470                      475                      480

Phe  Ala  Ser  Val  Val  Ile  Ser  Gly  Gln  Ala  Ile  Val  Ala  Lys  Ala  Pro
                    485                      490                      495

Phe  Thr  Arg  Arg  Asn  Arg  Phe  Ile  Leu  Thr  Ala  Ser  Met  Ala  Leu  Gly
               500                      505                      510

Tyr  Gly  Ala  Thr  Leu  Val  Pro  Thr  Trp  Phe  Gly  Asn  Val  Phe  Pro  Gln
          515                      520                      525

Thr  Glu  Asn  Arg  Asp  Leu  Glu  Gly  Phe  Glu  Asn  Ala  Ile  Glu  Leu  Val
     530                      535                      540

Leu  Glu  Thr  Gly  Phe  Ala  Val  Thr  Ala  Phe  Val  Ala  Met  Leu  Leu  Asn
545                      550                      555                      560

Ala  Ile  Met  Pro  Ala  Glu  Val  Glu  Glu  Ile  Gly  Ala  Val  Thr  Pro  Met
               565                      570                      575

Pro  Val  Ser  Ala  His  Asp  Asn  Arg  Asp  Gly  Glu  Ala  Glu  Tyr  Gln  Ser
               580                      585                      590

Lys  Gln  Ala
          595
```

( 2 ) INFORMATION FOR SEQ ID NO:12:

( i ) SEQUENCE CHARACTERISTICS:
        ( A ) LENGTH: 580 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Region
        ( B ) LOCATION: 207..236
        ( D ) OTHER INFORMATION: /note= "Encompasses TM 4 of Figure
            4"

( i x ) FEATURE:
        ( A ) NAME/KEY: Region
        ( B ) LOCATION: 437..499
        ( D ) OTHER INFORMATION: /note= "Encompasses TM 9 and TM 10
            of Figure 4"

( x i ) SEQUENCE DESCRIPTION: SEQ ID NO:12:

```
Met  Asp  Gly  Pro  Asp  Gln  Ile  Gly  Pro  Asp  Val  Arg  Pro  Arg  Arg  Thr
1                   5                        10                       15

Phe  Gly  Asp  Arg  Val  Arg  Arg  Ala  Ala  Arg  Ala  Phe  Thr  Thr  Arg  Asp
               20                       25                       30

Gly  Leu  Ile  Gly  Asp  Tyr  Asp  Tyr  Gly  Phe  Leu  Phe  Thr  Pro  Arg  Leu
          35                       40                       45

Pro  Phe  Val  Lys  Gln  Lys  Arg  Arg  Ala  Ala  Pro  Phe  Phe  Gly  Leu  Glu
     50                       55                       60

Asp  Lys  Ile  Pro  Leu  Val  Leu  Ala  Leu  Leu  Leu  Gly  Leu  Gln  His  Ala
65                       70                       75                       80

Leu  Ala  Met  Leu  Ala  Gly  Val  Ile  Thr  Pro  Pro  Ile  Leu  Leu  Ala  Gly
               85                       90                       95

Ser  Ser  Gly  Ala  Asn  Phe  Gly  Ala  Asp  Glu  Ser  Gln  Tyr  Leu  Val  Ser
               100                      105                      110

Thr  Ser  Leu  Ile  Val  Ser  Gly  Leu  Leu  Ser  Ala  Val  Gln  Met  Phe  Arg
          115                      120                      125

Leu  His  Val  Tyr  Lys  Thr  Arg  Tyr  Tyr  Val  Gly  Thr  Gly  Leu  Val  Ser
     130                      135                      140

Val  Val  Gly  Thr  Ser  Phe  Gly  Thr  Ile  Thr  Val  Ala  Thr  Gly  Thr  Phe
```

-continued

```
        145                     150                     155                     160
Asn Gln Met Tyr Ser Thr Gly Tyr Cys Pro Val Asp Gly Ser Gly Asn
                165                     170                     175
Arg Leu Pro Cys Pro Lys Gly Tyr Gly Ala Leu Leu Ala Thr Ser Cys
            180                     185                     190
Leu Cys Ser Leu Leu Glu Ile Gly Leu Ser Phe Met Ser Ser Arg Leu
        195                     200                     205
Leu Lys Ala Leu Phe Pro Pro Ile Val Thr Gly Pro Thr Val Phe Leu
    210                     215                     220
Ile Gly Ala Ser Leu Ile Gly Asn Ala Met Lys Asp Trp Ala Gly Gly
225                     230                     235                     240
Ser Gly Thr Cys Ser Ser Asn Pro Gly Asn Gly Ala Leu Cys Pro Ser
                245                     250                     255
Ala Asp Ala Pro His Pro Leu Pro Trp Gly Ser Ala Glu Phe Ile Gly
            260                     265                     270
Leu Gly Phe Leu Val Phe Ala Thr Ile Ile Leu Cys Glu Arg Phe Gly
        275                     280                     285
Ser Pro Ile Met Lys Ser Cys Ala Val Ile Val Gly Leu Leu Val Gly
    290                     295                     300
Cys Ile Val Ala Ala Ala Cys Gly Tyr Phe Asp Arg Ser Gly Ile Asp
305                     310                     315                     320
Ala Ala Pro Val Ala Ser Phe Ile Trp Val Lys Thr Phe Pro Leu Thr
                325                     330                     335
Ile Tyr Ala Pro Leu Ile Leu Pro Leu Leu Ala Val Tyr Met Val Ile
            340                     345                     350
Met Met Glu Ser Ile Gly Asp Ile Thr Ala Thr Cys Asp Val Ser Arg
        355                     360                     365
Leu Gln Val Glu Gly Ala Thr Phe Asp Ser Arg Ile Gln Gly Gly Val
    370                     375                     380
Leu Gly Asn Gly Ile Thr Cys Leu Leu Ala Gly Leu Cys Thr Ile Thr
385                     390                     395                     400
Pro Met Ser Val Phe Ala Gln Asn Asn Gly Val Ile Ala Leu Thr Pro
                405                     410                     415
Cys Ala Asn Arg Lys Ala Gly Tyr Cys Cys Cys Phe Phe Leu Val Val
            420                     425                     430
Met Gly Ile Phe Ala Lys Phe Ala Ala Leu Val Ala Ile Pro Ser
        435                     440                     445
Ser Val Leu Gly Gly Met Thr Thr Phe Leu Phe Ser Ser Val Ala Ile
    450                     455                     460
Ser Gly Val Arg Ile Met Cys Ser Val Asp Trp Thr Arg Arg Asn Arg
465                     470                     475                     480
Phe Ile Leu Thr Ala Ser Phe Ala Val Gly Met Ala Ala Thr Leu Val
                485                     490                     495
Pro Asp Trp Phe Ser Tyr Phe Phe Thr Tyr Ser Gly Asp Asn His Ala
            500                     505                     510
Leu Glu Gly Leu Leu Gln Ala Val Glu Leu Val Met Ala Asn Gly Phe
        515                     520                     525
Ala Val Thr Gly Phe Leu Gly Leu Leu Leu Asn Leu Ile Leu Pro Glu
    530                     535                     540
Asp Met Glu Glu Asp Val Val Glu Ser Glu Glu Asp Tyr Glu Ala Thr
545                     550                     555                     560
```

-continued

```
Thr Val Val Gly Met Gln Gly Gly Cys Glu Pro Gly Ser Ser Gly Gln
              565                 570                 575
Asn Val Lys Ala
            580
```

PURIFIED MAMMALIAN NUCLEOBASE PERMEASES; NUCLEIC ACIDS; ANTIBODIES

This regular patent application claims the benefit of U.S. Provisional Application number 60/000,788, filed Jul. 5, 1995.

FIELD OF THE INVENTION

The present invention relates to compositions related to proteins which function in cellular physiology, development, and differentiation of mammalian cells. In particular, it provides proteins which exhibit high structural similarity to proteins which exhibit the biological capacity to serve as a permease for nucleobases, which typically can be used in nucleic acid metabolism. Nucleic acids encoding said proteins and antibodies which bind are also provided.

BACKGROUND OF THE INVENTION

Multicellular living organisms exhibit specialization of function among various tissues. For example, different cell types have evolved to handle specific functions more efficiently than unicellular organisms. See, e.g., Gilbert (1991) *Developmental Biology* (3d ed.), Sinauer Associates, Sunderland, Mass.; Browder et al. (1991) *Developmental Biology* (3d. ed.), Saunders, Philadelphia, Pa.; Russo et al. (1992) *Development: The Molecular Genetic Approach*, Springer-Verlag, New York, N.Y.; and Wilkins (1993) *Genetic Analysis of Animal Development* (2d ed.) Wiley-Liss, New York, N.Y. Each cell within a multicellular organism typically experiences peculiar environmental factors distinct from cells located elsewhere in the organism. Spatial and microenvironmental differences require different cellular functions. The evolutionary response to the different environmental effects on the cells has been for the different cells to specialize in function.

The evolutionary development of specialization in different cells is paralleled by an ontological development of cell types. The adult form is derived initially from a single or few cells. This cell divides into multiple cells and the cells differentiate into a diverse group of cells, most exhibiting some degree of specialization in location or function. The inability to modulate or steer development of cells within a developing organism prevents proper formation or development of specialized tissues and organs or prevents repair of damaged tissues, resulting, e.g., though disease or aging.

Within the early embryo, particular layers, e.g., endoderm, mesoderm, and ectoderm, are destined to differentiate to form specific organs and cell types. For example, hematopoiesis is the process by which all blood cells are formed from multipotential, undifferentiated hematopoietic stem cells (HSCs). The first active site of hematopoiesis occurs in the yolk sac, both in birds and in mammals, at approximately day 7.5 of gestation, In mammals, it has been suggested that all hematopoietic activity results from the colonization of the embryo with cells that migrate from the yolk sac to the fetal liver after the activation of circulation by day 8.5. These cells would later colonize the bone marrow and be responsible for the formation of blood cells for the entire life of the organism. HSC activity was defined in these studies as the formation of day 8 CFU-S—macroscopic colonies on the spleen of recipient mice at 8 days posttransplantation. See, McCulloch and Till (1964) *Rad. Res.* 22:383–396, which describes an assay later shown to detect only committed hematopoietic progenitors. Recent studies in the mouse showed that the splancnopleura, the para-aortic, or the aorta, gonada, and mesonephros region (AGM) contain hematopoietic activity earlier than the fetal liver. Moreover, complete multilineage, long-term repopulation of irradiated mice with cells derived from the AGM region was reported.

Embryonic stem (ES) cells are derived from the inner cell mass of blastocysts and appear to resemble the primitive ectoderm of the postimplantation embryo. Culture systems of ES cells that allow their differentiation in vitro into EBs containing hematopoietic activity have been described. Analysis of proteins important in these early developmental stages are likely to be important in the development of the functions of the resulting cells.

However, many of the proteins and biological activities crucial to early differentiation and physiology of these cells remain unknown. Moreover, lack of recognition genes regulated in the early development of these cell types is likely to delay recognition and definition of important functions of fundamental importance. Thus a need exists for better description of the factors and mechanisms involved in signals in differentiation and development of mammalian cell types. The present invention provides this and many other new teachings.

SUMMARY OF THE INVENTION

The present invention is based, in part, upon the discovery of a cDNA clone from a vertebrate, which exhibits substantial structural homology to other proteins from prokaryotes which function biologically as a nucleoside transporter.

The present invention provides a recombinant or substantially pure protein comprising a plurality of non-overlapping segments of at least about 8 amino acids from SEQ ID NO: 2; a nucleic acid encoding that protein; a nucleic acid comprising sequence exhibiting at least about 80% sequence identity to a fragment of at least about 30 nucleotides from the coding portion of SEQ ID NO: 1; and an antibody raised to the protein. In one embodiment, the plurality numbers at least three, and the segments include at least two with a length of at least about 10 amino acids. In other embodiments, the protein exhibits the sequence of a naturally occurring protein from a primate, including a human; it comprises at least one polypeptide segment of at least about 20 amino acids of SEQ ID NO: 2; it exhibits nucleobase binding affinity; it exhibits nucleobase permease activity; or it exhibits a post-translational modification pattern distinct from a natural nucleobase permease.

The present invention also provides such a protein and a pharmaceutically acceptable carrier. In another embodiment, the protein is a fusion protein further comprising a sequence useful for purification or detection, including a FLAG sequence.

In one nucleic acid embodiment, the nucleic acid encodes at least three non-overlapping segments of at least about 8 amino acids from SEQ ID NO: 2, and the fragments include at least two with a length of at least about 10 amino acids. In other embodiments, the nucleic acid encodes at least three TM segments of SEQ ID NO: 2; it comprises sequence which exhibits at least 80% sequence identity to the fragment which encodes the portion of the nucleic acid.

In other embodiments, the invention provides an antibody raised to a recombinant or substantially pure protein comprising a plurality of non-overlapping segments of at least about 8 amino acids from SEQ ID NO: 2; the nucleobase permease is a primate protein, including one from human; the antibody is raised against a peptide exhibiting a sequence of at least about seven amino acids of SEQ ID NO: 2; the antibody blocks binding of the nucleobase permease to its natural nucleobase substrate; the antibody blocks transfer by the nucleobase permease of its natural substrate; the antibody is a monoclonal antibody; or the antibody is labeled.

The present invention also provides a recombinant or isolated nucleic acid exhibiting at least about 80% sequence identity to a fragment of at least about 30 nucleotides from the coding portion of SEQ ID NO: 1. In another embodiment, the nucleic acid encodes a protein comprising a plurality of non-overlapping segments of at least about 8 amino acids from a mammalian nucleobase permease of SEQ ID NO: 2 or 4.

In another embodiment, the invention provides a method of making a nucleobase permease comprising expressing a nucleic acid above.

The invention also provides a kit with a recombinant or substantially pure protein comprising a plurality of non-overlapping segments of at least about 8 amino acids from a mammalian nucleobase permease; with a nucleic acid encoding the protein; with a nucleic acid comprising sequence with at least about 80% sequence identity to a fragment of at least about 30 nucleotides from the coding portion of SEQ ID NO: 1; or with an antibody raised to the protein. In other embodiments, the protein exhibits a natural sequence from a primate, including a human; the protein exhibits at least three non-overlapping segments of at least about 8 amino acids from a mammalian nucleobase permease of SEQ ID NO: 2 or 4 and the segments include at least two with a length of at least about 10 amino acids; the protein has at least one polypeptide segment of at least about 20 amino acids of SEQ ID NO: 2, which includes a protein comprising the full length of SEQ ID NO: 2; the protein exhibits binding affinity for a nucleobase; the protein exhibits permease activity for a nucleobase; or the protein exhibits a post-translational modification pattern distinct from a natural nucleobase permease. In other embodiments, the kit has an antibody wherein the nucleobase permease has a sequence of a natural primate protein, including one from a human;. the antibody is raised against a peptide comprising at least about 8 amino acids of SEQ ID NO: 2; the antibody blocks binding of the nucleobase permease to its natural nucleobase substrate; the antibody blocks transfer by said nucleobase permease of its natural substrate; the antibody is a monoclonal antibody; or the antibody is labeled.

The invention further provides an isolated population of cells consisting essentially of nucleobase permease positive cells.

The invention provides a method of measuring capacity of a mammalian nucleobase permease to bind a substrate comprising producing a mammalian nucleobase permease, and measuring specific binding of the substrate to the nucleobase permease. In another embodiment, the substrate contains at least one nucleobase homolog, the mammalian nucleobase permease has a plurality of non-overlapping segments of at least about 8 amino acids from SEQ ID NO: 2; and the binding leads to blocking of permease activity. In another embodiment, the nucleobase homolog is a chemotherapeutic agent which can be transported by said permease into a cell.

BRIEF DESCRIPTION OF THE DRAWINGS

FIGS. 2A and 2B show the nucleotide and deduced protein sequence of Clone 240 (Yspl1) (see SEQ ID NO: 1 also). The four protein forms derived from the Yspl1 gene are indicated by arrows. The gray boxes, labeled TM1–12, represent presumptive membrane spanning hydrophobic segments. The hydrophobic sequence labeled as box X represents an inserted domain in the canonical nucleobase permease fold of Yspl1—it may also be membrane associated but should not alter the consensus topological features of Yspl1.

FIG. 4 shows the identification of Yspl1 as a nucleobase permease. A nucleobase permease family. Portions of a ClustalW-derived (Thompson, et al. (1994) *Nucl. Acids Res.* 22:4673–4680) sequence alignment between Yspl1 and permease homologues are presented in regions that display family-specific sequence patterns. TM helices are labeled as in FIGS. 2A and 2B. Shading indicates identities (dark) or conserved (light) residues in a column. The sequences include an *E. coli* uracil permease (EcUraA; Genbank Acc. # X73586, Andersen, et al. (1995) Genbank Acc. # X73586; see SEQ ID NO: 5) and a permease-like gene (EcORF, Genbank Acc. # L10328; Burland, et al. (1993) *Genomics* 16:551–561 and Genbank Acc. # L10328, orf o463; see SEQ ID NO: 6), pyrimidine permeases from *B. subtillus* (BsPyrP, Genbank Acc. # M59757, Quinn, et al. (1991) *J. Biol. Chem.* 266:9113–9127 and Genbank Acc. # M59775; see SEQ ID NO: 7) and *B. caldolyticus* (BcPyrP, Genbank Acc. # X76083, Ghim and Neuhard (1994) *J. Bacteriol.* 176:3698–3707, and Genbank Acc. # X76083; see SEQ ID NO: 8), xanthine permease from *B. subtillus* (BsXpt, Genbank Acc. # X83878, Saxild, et al. (1995) Genbank Acc. # X83878; see SEQ ID NO: 9) and a similar hypothetical protein (BsORF, Genbank Acc. # X73124, Schneider, et al. (1993) *Molec. Microbiol.* 10:371–384 and Genbank Acc. # X73124; see SEQ ID NO: 10), and two uric acid-xanthine permeases from *A. nidulans* (AnUAPA; Genbank Acc. # X71807, Gorfinkiel, et al. (1993) *J. Biol. Chem.* 268:23376–23381 and Genbank Acc. # X73184 see SEQ ID NO: 11; AnUAPC, Genbank Acc. # X79796, Diallinas, et al. (1995) *J. Biol. Chem.* 270:8610–8622 and Genbank Acc. # X79796; see SEQ ID NO: 12). Mouse Yspl1 is abbreviated MoYSLP1.

FIG. 8A shows comparative analysis of expression in embroyoid bodies of Brachyury, βH1-globin, α-fetoprotein, and Yspl1. W=early day 8.5 embryo proper; R=late day 8.5 embryo proper; YS=day 8.5 yolk sac; ES=embryonic stem cells; d3, d6, d9 =day 3, day 6, and day 9 embryoid bodies; RT=reverse transcriptase control: early day 8.5 embryo RNA was used in the cDNA synthesis reaction to which no reverse transcriptase was added.

FIG. 8B shows PCR analysis of Yspl1 expression in embryoid bodies developed in the absence of serum; FCS=ES cells developed for 5 days in media containing 10% fetal calf serum; CDM+ES cells developed for 5 days in Chemically Defined Medium (CDM); ACT=embryoid bodies developed for 5 days in CDM and BMP-4; W and YS=as above; H2O=no cDNA added; G=mouse genomic DNA. Yspl1 (arrow) was found in the day 8.5 yolk sac and the day 8.5 embryo proper, but not in EX cells or in embryoid bodies. The arrow head identifies a PCR product that corresponds to the amplification of a genomic Yspl1 sequence.

FIG. 8C shows PCR analysis of Yspl1 expression in a variety of fetal and adult tissues: 1=11.5 day yolk sac; 2=11.5 AGM region; 3=day 11.5 fetal liver; 4=day 11.5 head primordium; 5–16 are adult tissues: 5=placenta; 6=brain; 7=liver; 8=bone marrow; 9=thymus; 10=spleen; 11=skeletal muscle; 12=abdominal fat; 13=kidney; 14=lung; 15=heart; 16=testis; 17=N2a cells (American Type Cell Culture—ATCC CCl 131); 18=STO cells (ATCC CRL 1503); 19=FDCPmix A4 cells (ATCC; see Ford, et al. (1971) *Blood* 79:1962–1971; 20=reverse transcription control: day 11.5 yolk sac RNA was used in the CDNA synthesis reaction to which no reverse transcriptase was added; 21=water, as above.

DETAILED DESCRIPTION OF THE PREFERRED EMBODIMENTS

OUTLINE

Figure 1:
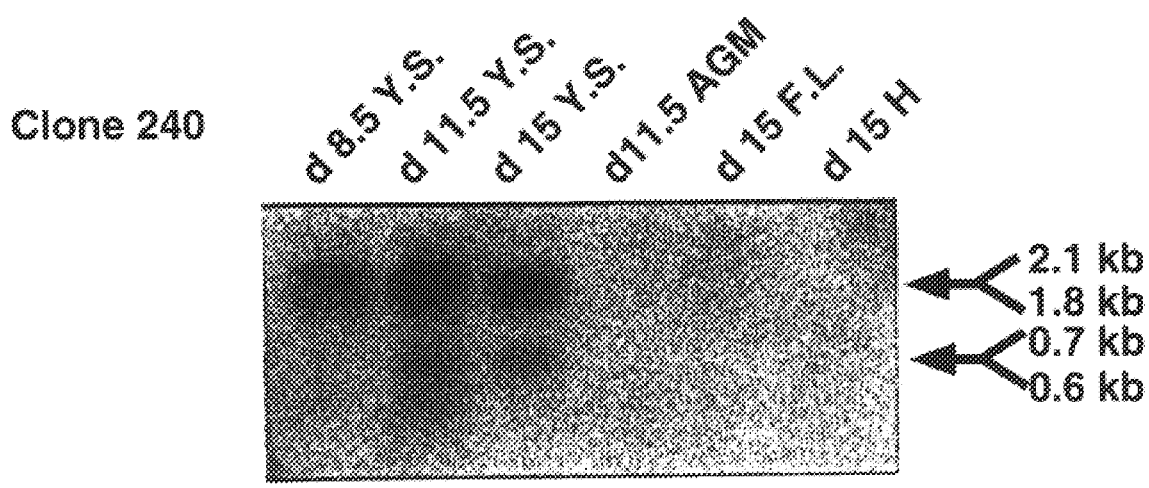
FIG. 1 shows Northern Blot Analysis of the expression of Yspl1 (clone 240) in the yolk sac and early intraembryonic sites of hematopoieis. These genes are differentially expressed during yolk sac development. None is expressed in intraembryonic sites of early hematopoiesis. Four different messages were identified for Clone 240 (sizes shown on the right). YS=yolk sac; AGM=aorta, gonada, mesonephros; FL=fetal liver; H=head primordium.
Figure 3:
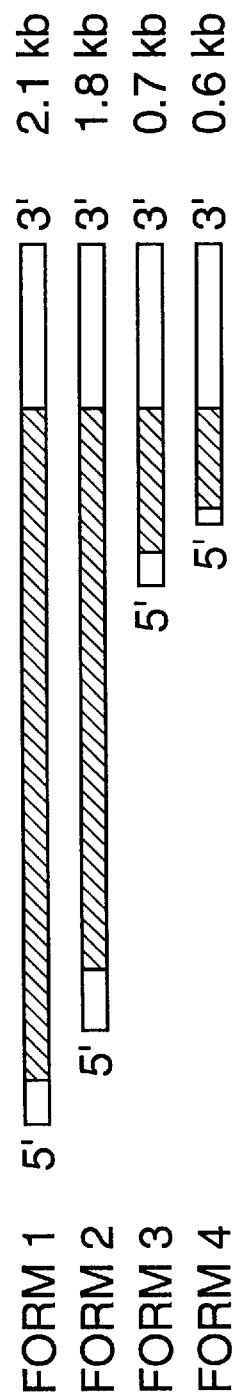
FIG. 3 shows a schematic diagram of forms 1, 2, 3, and 4.
Figure 5:
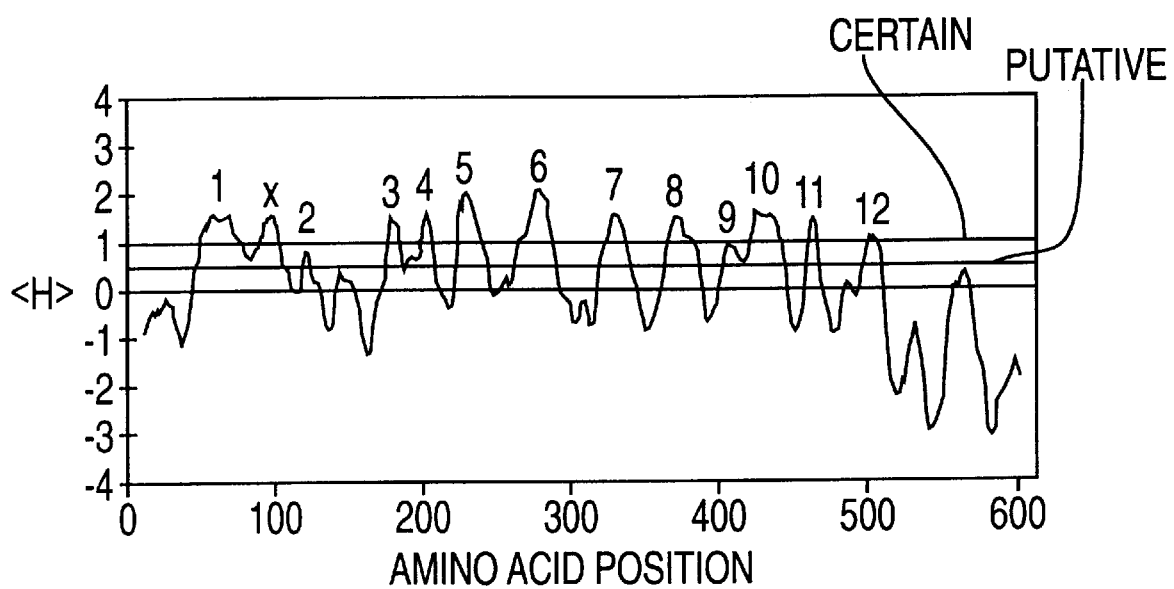
FIG. 5 shows membrane topology of Yspl1 . A TopPredII (Claros and von Heijne (1994) *Comp. Applic. Biosci.* 10:685–686) profile of the Yspl1 sequence showing peaks that reach beyond 'Putative' or 'Certain' baselines. Peaks representing the consensus twelve TM segments are labeled above, as is the hydrophobic X region outlined in FIG. 2A.
Figure 6:
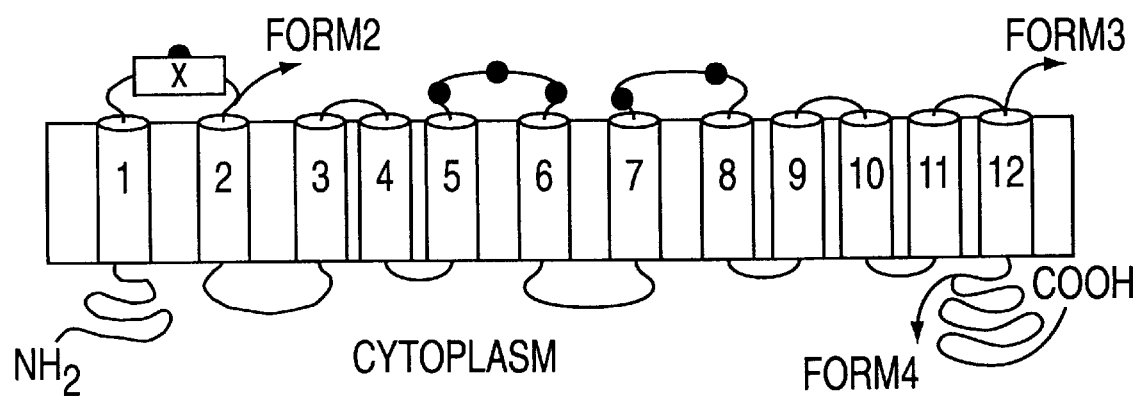
FIG. 6 shows a schematic arrangement of the TM helices in the membrane. The Yspl1 chain weaves through the membrane in an in-out fashion determined by TM regions and charged residue bias (von Heijne (1994) *Ann. Rev. Biophys. Biomolec. Struc.* 23:167–192). There are no N-glycosylation sites in the exposed, extracellular face of the molecule; however, cysteine residues capable of participating in disulfide links are marked by dark points. Start positions for Forms 2–4 are again indicated by arrows. Notably, Form 3 protein commences with the hydrophobic sequence of TM12 which could serve as a cleavable signal peptide, while a Form 4 molecule would be purely cytoplasmic.

I. General
II. Nucleic Acids
A. natural isolates; methods
B. synthetic genes
C. methods to isolate
III. Purified Nucleobase Permease
A. physical properties
B. biological properties
IV. Making Nucleobase Permease; Mimetics
A. recombinant methods
B. synthetic methods
C. natural purification
V. Physical Variants
A. sequence variants, fragments
B. post-translational variants
1. glycosylation
2 others
VI. Functional Variants
A. analogs; fragments
1. agonists
2. antagonists
B. mimetics
1. protein
2. chemicals
C. species variants
VII. Antibodies
A. polyclonal
B. monoclonal
C. fragments, binding compositions
VIII. Uses
A. diagnostic
B. therapeutic
IX. Kits
A. nucleic acid reagents
B. protein reagents
C. antibody reagents
X. Isolating Nucleobase Permease Specific Binding Partners I. General The present invention provides DNA sequence encoding a mammalian protein which exhibits structural features characteristic of functionally significant proteins, particularly which serve as nucleoside transport proteins. See, e.g., Pajor and Wright (1992) *J. Biol. Chem.* 267:3557–3560. The mouse gene embodiment described herein, isolated as designate Yspl1 or clone 240, provides various alternatively spliced variant messages, and contains an open reading frame encoding a presumptive protein of about 611 amino acids. These proteins correspond to intracellular, transmembrane, and extracellular protein forms, revealing novel aspects of nucleotide metabolism that may be relevant during mammalian development.

These proteins are designated nucleobase permeases based upon their structural homology to distantly related forms from much more primitive organisms, including bacteria and yeast. The nucleic acid distribution and temporal appearance in development are indicative of important roles in early development. See, e.g., Table 1.

Table 1: Distribution of nucleobase transferase through early development.
undetected at day 11.5 aorta, gonada, and mesonephros (AGM) regions
undetected at day 15.5 fetal liver
differential forms expressed in yolk sac over days 8.5 to 15
small transcripts (0.7 and 0.6 kb) detected at much lower levels at 8.5 day yolk sac
larger transcripts (2.1 and 1.8 kb) found at about 3-fold higher amounts than small transcripts (0.7 and 0.6 kb)

The overriding structural feature of the 611 amino acid Yspl1 chain is its patchwork of 20–30 residue hydrophobic segments separated by hydrophilic sequences of varying length, see Kyte and Doolittle (1982) *J. Mol. Biol.* 157:105–132. The weave of the chain through the membrane is dictated by these presumed membrane-spanning, hydrophobic helices, see, e.g., von Heijne (1994) *Ann. Rev. Biophys. Biomolec. Struc.* 23:167–192. An accurate prediction of the membrane topology of Yspl1 then depends on the correct number and sequence location of transmembrane (TM) segments as well as their orientation in the membrane;

protein termini and TM-linking regions may either be surface exposed or cytoplasmic. See Hartmann, et al. (1989) *Proc. Natl. Acad. Sci. USA* 86:5786–5790; Sippos and von Heijne (1993) *Eur. J. Biochem.* 213:1333–1340; Jones, et al. (1994) *Biochem.* 33:3038–3049; von Heijne (1994) *Ann. Rev. Biophys. Biomolec. Struc.* 23:167–192.

The introduction of evolutionary information in the form of sequence homologs simplifies the structural analysis considerably for related molecules which share a common structural framework in spite of considerable sequence divergence, see, e.g., Chothia and Lesk (1986) *EMBO J.* 5:823–826. This concept can be effectively extended to the strong prediction of TM regions across an aligned protein family whereas any single sequence may provide an uncertain topology. See Persson and Argos (1994) *J. Mol. Biol.* 237:182–192; Rost, et al. (1995) *Protein Sci.* 4:521–533). For the nucleobase permease, a number of sequence homologues were first assembled by comparative matching to protein and translated nucleotide databases (Altschul, et al. (1994) *Nature Genet.* 6:119–129; Koonin, et al. (1994) *EMBO J.* 13:493–503). These distant relatives of Yspl1 prominently include bacterial uracil permeases (Andersen, et al. (1995) Genbank Acc. # X73586; Burland, et al. (1993) *Genomics* 16:551–561 and Genbank Acc. # L10328, orf o463; Ghim and Neuhard (1994) *J. Bacteriol.* 176:3698–3707, and Genbank Acc. # X76083; Quinn, et al. (1991) *J. Biol. Chem.* 266:9113–9127 and Genbank Acc. # M59757; Saxild, et al. (1995) Genbank Acc. # X83878; Schneider, et al. (1993) *Molec. Microbiol.* 10:371–384 and Genbank Acc. # X73124) and fungal uric acid-xanthine permeases (Gorfinkiel, et al. (1993) *J. Biol. Chem.* 268:23376–23381 and Genbank Acc. # X71807; Diallinas, et al. (1995) *J. Biol. Chem.* 270:8610–8622 and Genbank Acc. # X79796) (FIG. 4). These varied purine and pyrimidine—generically, nucleobase—permease sequences were subjected to parallel analyses by a suite of computer programs that have greatly improved on the initial Kyte and Doolittle (1982) hydropathic profile as a means of predicting the topology of integral membrane proteins. Four algorithms (ALOM, MTOP, MEMSAT and TopPredII) (Klein, et al. (1985) *Biochim. Biophys. Acta* 815:468–476; Hartmann, et al. (1989)*Proc. Natl. Acad. Sci. USA* 86:5786–5790; Jones, et al. (1994) Biochem. 33:3038–3049; Claros and von Heijne (1994) *Comp. Applic. Biosci.* 10:685–686) were used to individually predict TM extensions and orientations; these predictions were pooled and mapped onto the multiple sequence alignment produced by ClustalW and MACAW (Thompson, et al. (1994) *Nucl. Acids Res.* 22:4673–4680; Schuler, et al. (1991) *Proteins* 9:180–190). Furthermore, these multiply aligned sequence files were used as input to PHD and TMAP (Rost, et al. (1995) *Protein Sci.* 4:521–533; Persson and Argos (1994) *J. Mol. Biol.* 237:18214 192) for a familial prediction of shared TM regions. Structural features that persisted in this two-step analysis are likely to be shared topological traits present in all members of this permease family from bacteria to vertebrates.

Figure 2A:
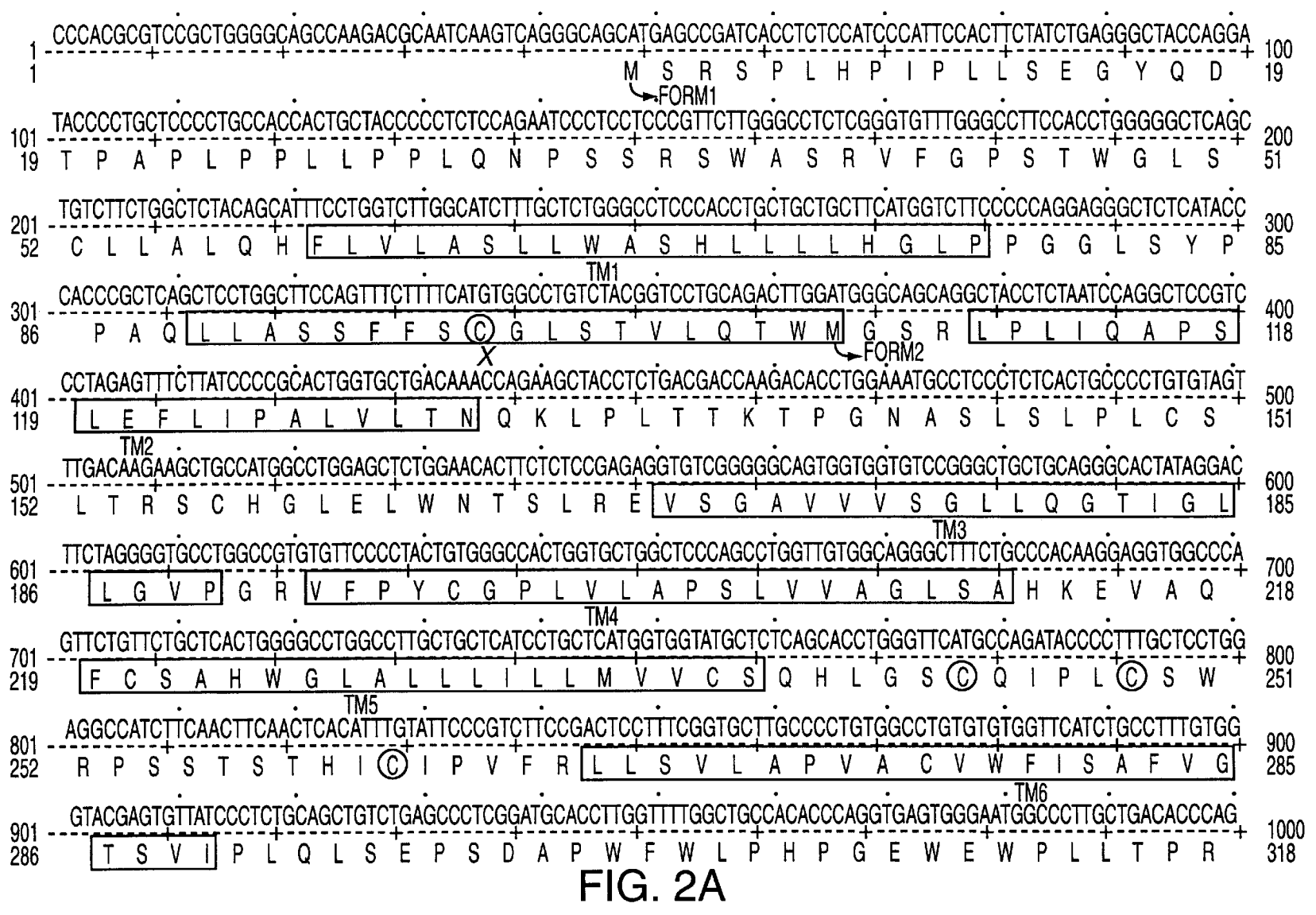
Figure 2B:
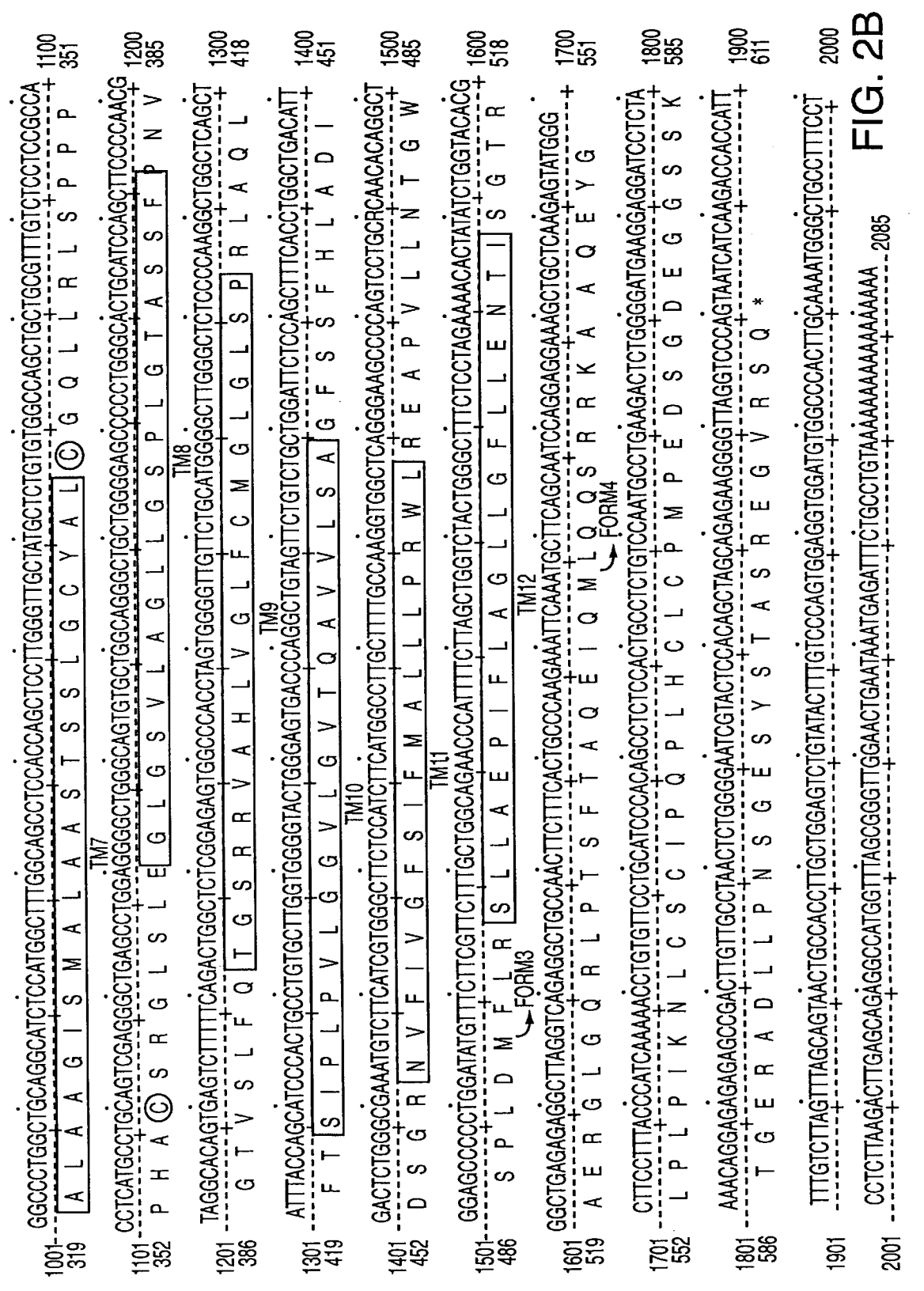

The TM analysis for Yspl1 and homologues suggested the presence of twelve consensus helical TM segments (FIG. 2). This result likely places this nucleobase permease family into a larger superfamily of 12-TM helix transporters (Nikaido and Saier (1992) *Science* 258:936–942; Uhl and Hartig (1992) *Trends Pharm. Sci.* 13:421–425; Griffith, et al. (1992) *Curr. Opin. Cell Biol.* 4:684–695; Marger and Saier (1993) *Trends Biochem. Sci.* 18:13–20; Henderson (1993) *Curr. Opin. Cell Biol.* 5:708–721; Maloney (1994) *Curr. Opin. Cell Biol.* 6:571–582) that act as discriminating protein channels for a wide variety of solutes (Kramer (1994) *Biochim. Biophys. Acta* 1185:1–34; Hediger (1994) *J. Exp. Biol.* 196:15–49). There are few amino acid motifs that survive between branches of this vast superfamily of 12-TM molecules (Griffith, et al. (1992) *Curr. Opin. Cell Biol.* 4:684–695; Henderson (1993) *Curr. Opin. Cell Biol.* 5:708–721; Marger and Saier (1993) *Trends Biochem. Sci.* 18:13–20; Goswitz and Brooker (1995) *Prot. Sci.* 4:534–537). The prominent sequence patterns that describe the Yspl1-like family (FIG. 4) cover TM4, TM9, and TM10; these motifs are distinct from other topologically analogous 12-TM patterns (Griffith, et al. (1992) *Curr. Opin. Cell Biol.* 4:684–695). Permease specificity within a universal TM framework may be modulated by these different structural motifs (see, e.g., Bloch, et al. (1992) *Molec. Microb.* 6:2989–2997). Nevertheless, profile methods (Gribskov, et al. (1987) *Proc. Natl. Acad. Sci. USA* 84:4355–4358; Thompson, et al. (1994) *Comp. Applic. Biosci.* 10:19–29) do reveal a faint but significant global similarity to a functionally similar family of 12-TM molecules formed by the allantoin and uracil permeases of yeast (Jund, et al. (1988) *Eur. J. Biochem.* 15:417–424 and Genbank Acc. # X06830; Rai, et al. (1988) *J. Bact.* 170:266–271 and Genbank Acc. # M24098; Yoo, et al. (1992) Yeast 8:997–1006 and Genbank Acc. # Z15121) and the cytosine permeases of *E. coli* and yeast (Danielsen, et al. (1992) *Molec. Microbiol.* 6:1335–1344 and Genbank Acc. # X63656; Weber, et al. (1990) *Mole. Microbiol.* 4:585–596 and Genbank Acc. # X51751). Yspl1 remains the sole vertebrate member of a now expanded nucleobase permease family.

Figure 7:
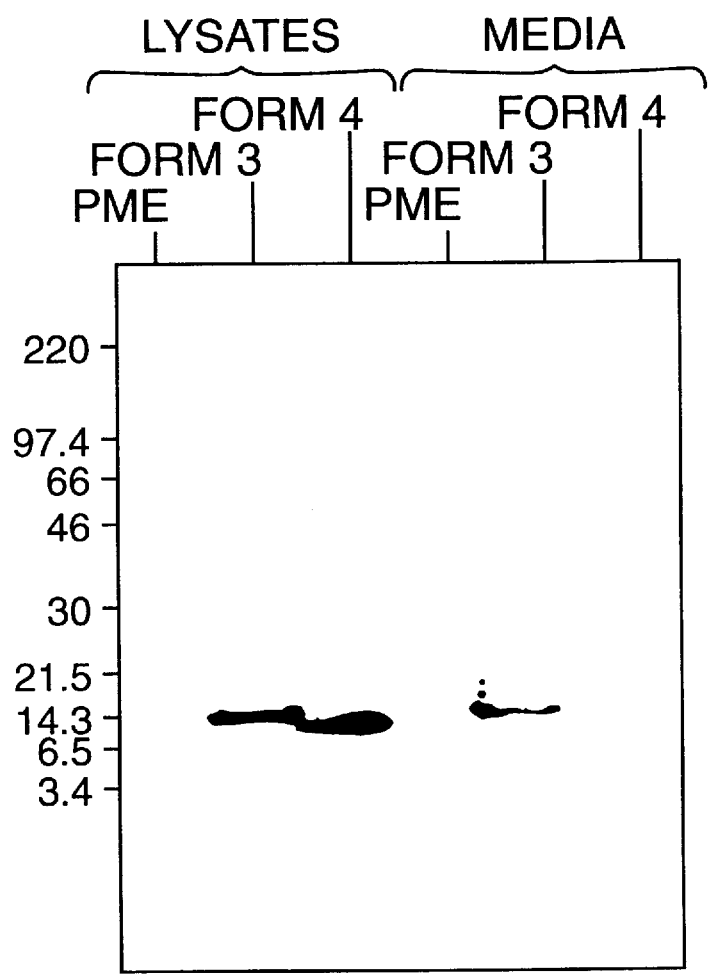
FIG. 7 shows protein expression of Form 3 and Form 4 cDNAs of Yspl1. Western blot obtained using the M2 antibody directed to the FLAG sequence introduced at the C-terminus of the Yspl1 protein constructs. Protein Form 3 of Yspl1 can be observed both intracellularly (lysates) and extracellularly (medium). Protein Form 4 of Yspl1 is intracellular. PME-pME18X plasmid without insert was transfected into COS-7 cells and used as negative control for the expression of Yspl1.
Figure 8A:
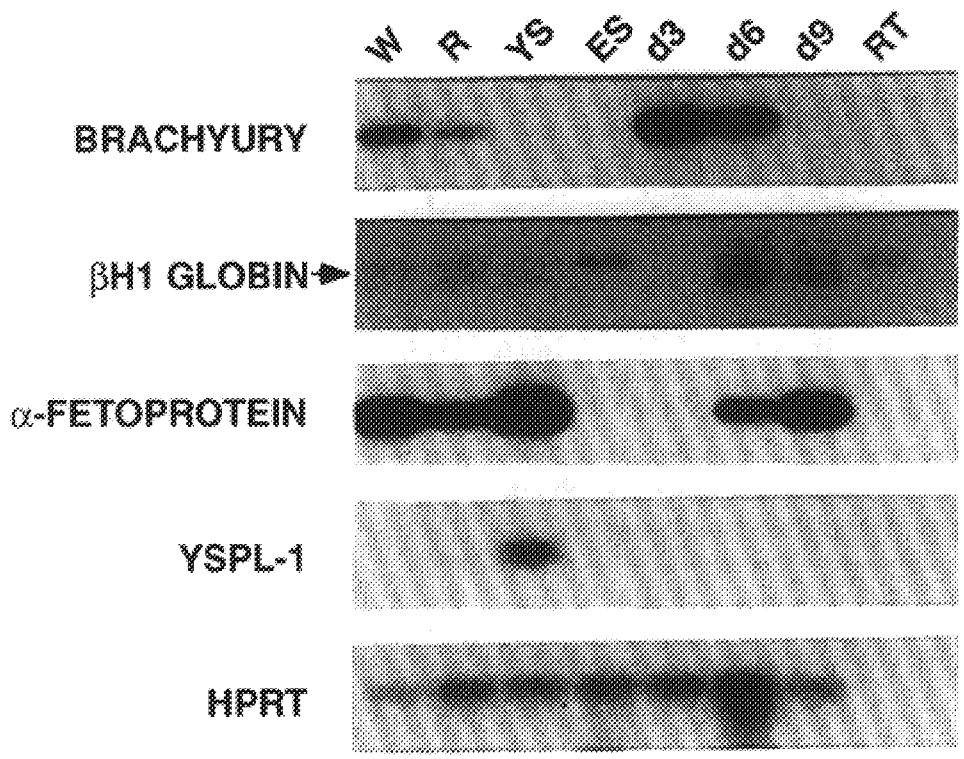
FIGS. 8A, 8B, and 8C show PCR analysis of the expression of Yspl1. The location of the primers in the Yspl1 DNA sequence were selected so that all four forms of the gene shown in FIG. 3 were amplified.
Figure 8B:
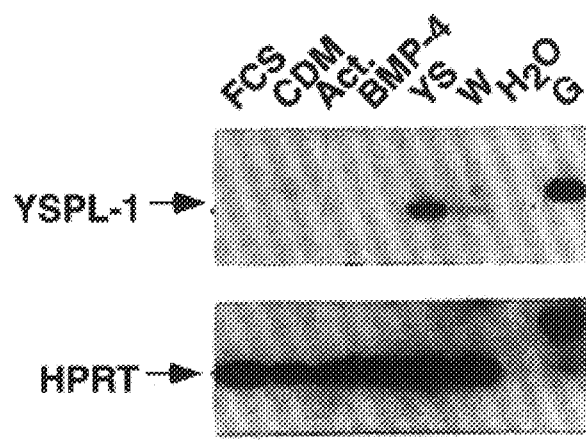
Figure 8C:

The different forms of Yspl1 represent molecules with staggered N-termini and common C-termini (FIGS. 2A and 2B) of which the longest (611 residue) chain, as discussed previously, forms a prototypical 12-TM transporter. Form 2 which lacks TM1 and the hydrophobic "X" stretch (FIGS. 2A, 2B) would still encode a truncated permease with eleven TM helices. Form 3 cDNA encodes a protein of 130 residues (Mr $14 \times 10^3$) with one hydrophobic TM12 stretch that could then resemble an N-terminal secretion peptide for a domain formed by the C-terminal, predicted cytoplasmic segment of Yspl1. Finally, an 82 amino acid Form 4 (Mr $9 \times 10^3$) would be formed by a shortened version of this cytoplasmic domain, lacking any hydrophobic segments. To determine if Form 3 Yspl1 would be secreted or intracellular, and to confirm the cytoplasmic localization of Form 4 protein, constructs of Yspl1 in which a FLAG epitope tag was introduced at the C-termini of both Form 3 and 4 proteins were made. Western Blot analysis using the M2 antibody directed to this tag sequence shows that Form 3 Yspl1 can be detected both inside and outside cells whereas Form 4 is purely intracellular (FIG. 7).

To determine if Yspl1 is expressed in embryoid bodies (EBs) at levels undetectable by Northern hybridization, 30 cycle PCR analysis was conducted comparing the expression of Yspl1 with that of a mesoderm marker (Brachyury), a hematopoietic marker ($\beta$H1-globin) and a commonly used marker of yolk sac differentiation ($\alpha$-fetoprotein). In contrast to Brachyury (detectable at day 3 and day 6), $\beta$H1-globin (detectable from day 6) and $\alpha$-fetoprotein (detectable from day 9 of EB development), Yspl1 was not found to be expressed in EBs developed up to day 9 under standard conditions or day 5.0 EBs developed in CDM (Chemically Defined Media) alone (Johansson and Wiles (1995) *Mol Cell Biol.* 15:141–151), or in the presence of Activin-A or BMP-4 (mediators of the expression of mesoderm and hematopoietic markers, respectively. See Johansson and Wiles (1995) *Mol Cell Biol.* 15:141–151).

Functionally, the permease should serve to transport a nucleobase or analog thereof into a cell. It will typically function against a gradient of the nucleobase, and may well involve active transport. The energy source is likely to be ATP, but may alternatively depend upon other phosphorylated molecules used by biological systems, well recognized and described in standard textbooks of biochemistry. The nucleobase will typically be utilized in aspects of nucleic acid metabolism, both synthesis and degradation. See. e.g., textbooks by L. Stryer or A. Kornberg. The permease may be a cotransporter, which functions, e.g., by an ion gradient. The ion gradient may be Na+, K+, Ca++, or other common biologically relevant ions. The permease may serve to either actively pump the nucleobase into the appropriate compartments, or may serve to increase the rate of transfer in a more passive transport.

II. Nucleic Acids

Table 2 discloses the nucleotide and amino acid sequences of one member of the nucleobase permease family. The embodiment described represents the first described member of the family derived from a vertebrate, and this particular embodiment is from a mammal. The disclosed nucleotide sequence and the related reagents are useful in constructing a DNA clone useful for expressing various forms of the nucleobase permease, or, e.g., isolating a homologous gene from another natural source, including other members of the family. The sequences will be useful in isolating other genes, e.g., allelic or polymorphic variants or alternatively spliced isoforms from other vertebrates, particularly from mammals, including primates, such as a human.

The coding sequence runs from nucleotide positions 48 to 1883 (end of termination codon). Various alternative splicing forms have also been identified in cells. An encoded form 1 appears to extend from amino acid 1 (met) to 611 (gln); form 2 corresponds to sequence from amino acid 107 (met) to 611; form 3 corresponds to sequence from amino acid 490 (met) to 611; form 4 corresponds to sequence from amino acid 538 (met) to 611; and a form 5 corresponds to sequence encoded by the end in a different reading frame. The messages appear to result from natural splicing variations. See Table 2.

TABLE 2

Nucleotide sequence encoding a mouse nucleobase permease, and the predicted amino acid sequence of the resulting product. Designated SEQ ID NO: 1 and 2.

| CCCACGCGTC | CGCTGGGGCA | GCCAAGACGC | AATCAAGTCA | GGGCAGC | ATG Met 1 | AGC Ser | CGA Arg | 56 |
|---|---|---|---|---|---|---|---|---|

| TCA Ser | CCT Pro 5 | CTC Leu | CAT His | CCC Pro | ATT Ile | CCA Pro 10 | CTT Leu | CTA Leu | TCT Ser | GAG Glu | GGC Gly 15 | TAC Tyr | CAG Gln | GAT Asp | ACC Thr | 104 |
|---|---|---|---|---|---|---|---|---|---|---|---|---|---|---|---|---|
| CCT Pro 20 | GCT Ala | CCC Pro | CTG Leu | CCA Pro | CCA Pro 25 | CTG Leu | CTA Leu | CCC Pro | CCT Pro | CTC Leu 30 | CAG Gln | AAT Asn | CCC Pro | TCC Ser | TCC Ser 35 | 152 |
| CGT Arg | TCT Ser | TGG Trp | GCC Ala | TCT Ser 40 | CGG Arg | GTG Val | TTT Phe | GGG Gly | CCT Pro 45 | TCC Ser | ACC Thr | TGG Trp | GGG Gly | CTC Leu 50 | AGC Ser | 200 |
| TGT Cys | CTT Leu | CTG Leu | GCT Ala 55 | CTA Leu | CAG Gln | CAT His | TTC Phe | CTG Leu 60 | GTC Val | TTG Leu | GCA Ala | TCT Ser | TTG Leu 65 | CTC Leu | TGG Trp | 248 |
| GCC Ala | TCC Ser | CAC His 70 | CTG Leu | CTG Leu | CTG Leu | CTT Leu | CAT His 75 | GGT Gly | CTT Leu | CCC Pro | CCA Pro | GGA Gly 80 | GGG Gly | CTC Leu | TCA Ser | 296 |
| TAC Tyr | CCA Pro 85 | CCC Pro | GCT Ala | CAG Gln | CTC Leu | CTG Leu 90 | GCT Ala | TCC Ser | AGT Ser | TTC Phe | TTT Phe 95 | TCA Ser | TGT Cys | GGC Gly | CTG Leu | 344 |
| TCT Ser 100 | ACG Thr | GTC Val | CTG Leu | CAG Gln | ACT Thr 105 | TGG Trp | ATG Met | GGC Gly | AGC Ser | AGG Arg 110 | CTA Leu | CCT Pro | CTA Leu | ATC Ile | CAG Gln 115 | 392 |
| GCT Ala | CCG Pro | TCC Ser | CTA Leu | GAG Glu 120 | TTT Phe | CTT Leu | ATC Ile | CCC Pro | GCA Ala 125 | CTG Leu | GTG Val | CTG Leu | ACA Thr | AAC Asn 130 | CAG Gln | 440 |
| AAG Lys | CTA Leu | CCT Pro | CTG Leu 135 | ACG Thr | ACC Thr | AAG Lys | ACA Thr | CCT Pro 140 | GGA Gly | AAT Asn | GCC Ala | TCC Ser | CTC Leu 145 | TCA Ser | CTG Leu | 488 |
| CCC Pro | CTG Leu | TGT Cys 150 | AGT Ser | TTG Leu | ACA Thr | AGA Arg | AGC Ser 155 | TGC Cys | CAT His | GGC Gly | CTG Leu | GAG Glu 160 | CTC Leu | TGG Trp | AAC Asn | 536 |
| ACT Thr | TCT Ser 165 | CTC Leu | CGA Arg | GAG Glu | GTG Val | TCG Ser 170 | GGG Gly | GCA Ala | GTG Val | GTG Val | GTG Val 175 | TCC Ser | GGG Gly | CTG Leu | CTG Leu | 584 |
| CAG Gln 180 | GGC Gly | ACT Thr | ATA Ile | GGA Gly | CTT Leu 185 | CTA Leu | GGG Gly | GTG Val | CCT Pro | GGC Gly 190 | CGT Arg | GTG Val | TTC Phe | CCC Pro | TAC Tyr 195 | 632 |

TABLE 2-continued

Nucleotide sequence encoding a mouse nucleobase permease, and the predicted amino acid sequence of the resulting product. Designated SEQ ID NO: 1 and 2.

| | | | | | | | | | | | | | | | | |
|---|---|---|---|---|---|---|---|---|---|---|---|---|---|---|---|---|
| TGT | GGG | CCA | CTG | GTG | CTG | GCT | CCC | AGC | CTG | GTT | GTG | GCA | GGG | CTT | TCT | 680 |
| Cys | Gly | Pro | Leu<br>200 | Val | Leu | Ala | Pro | Ser | Leu<br>205 | Val | Val | Ala | Gly | Leu<br>210 | Ser | |
| GCC | CAC | AAG | GAG | GTG | GCC | CAG | TTC | TGT | TCT | GCT | CAC | TGG | GGC | CTG | GCC | 728 |
| Ala | His | Lys | Glu<br>215 | Val | Ala | Gln | Phe | Cys<br>220 | Ser | Ala | His | Trp | Gly<br>225 | Leu | Ala | |
| TTG | CTG | CTC | ATC | CTG | CTC | ATG | GTG | GTA | TGC | TCT | CAG | CAC | CTG | GGT | TCA | 776 |
| Leu | Leu | Leu<br>230 | Ile | Leu | Leu | Met | Val<br>235 | Val | Cys | Ser | Gln | His<br>240 | Leu | Gly | Ser | |
| TGC | CAG | ATA | CCC | CTT | TGC | TCC | TGG | AGG | CCA | TCT | TCA | ACT | TCA | ACT | CAC | 824 |
| Cys | Gln<br>245 | Ile | Pro | Leu | Cys | Ser<br>250 | Trp | Arg | Pro | Ser | Ser<br>255 | Thr | Ser | Thr | His | |
| ATT | TGT | ATT | CCC | GTC | TTC | CGA | CTC | CTT | TCG | GTG | CTT | GCC | CCT | GTG | GCC | 872 |
| Ile<br>260 | Cys | Ile | Pro | Val | Phe<br>265 | Arg | Leu | Leu | Ser | Val<br>270 | Leu | Ala | Pro | Val | Ala<br>275 | |
| TGT | GTG | TGG | TTC | ATC | TCT | GCC | TTT | GTG | GGT | ACG | AGT | GTT | ATC | CCT | CTG | 920 |
| Cys | Val | Trp | Phe | Ile<br>280 | Ser | Ala | Phe | Val | Gly<br>285 | Thr | Ser | Val | Ile | Pro<br>290 | Leu | |
| CAG | CTG | TCT | GAG | CCC | TCG | GAT | GCA | CCT | TGG | TTT | TGG | CTG | CCA | CAC | CCA | 968 |
| Gln | Leu | Ser | Glu<br>295 | Pro | Ser | Asp | Ala | Pro<br>300 | Trp | Phe | Trp | Leu | Pro<br>305 | His | Pro | |
| GGT | GAG | TGG | GAA | TGG | CCC | TTG | CTG | ACA | CCC | AGG | GCC | CTG | GCT | GCA | GGC | 1016 |
| Gly | Glu | Trp<br>310 | Glu | Trp | Pro | Leu | Leu<br>315 | Thr | Pro | Arg | Ala | Leu<br>320 | Ala | Ala | Gly | |
| ATC | TCC | ATG | GCT | TTG | GCA | GCC | TCC | ACC | AGC | TCC | TTG | GGT | TGC | TAT | GCT | 1064 |
| Ile | Ser<br>325 | Met | Ala | Leu | Ala | Ala<br>330 | Ser | Thr | Ser | Ser | Leu<br>335 | Gly | Cys | Tyr | Ala | |
| CTG | TGT | GGC | CAG | CTG | CTG | CGT | TTG | TCT | CCT | CCG | CCA | CCT | CAT | GCC | TGC | 1112 |
| Leu<br>340 | Cys | Gly | Gln | Leu | Leu<br>345 | Arg | Leu | Ser | Pro | Pro<br>350 | Pro | Pro | His | Ala | Cys<br>355 | |
| AGT | CGA | GGG | CTG | AGC | CTG | GAG | GGG | CTG | GGC | AGT | GTG | CTG | GCA | GGG | CTG | 1160 |
| Ser | Arg | Gly | Leu | Ser<br>360 | Leu | Glu | Gly | Leu | Gly<br>365 | Ser | Val | Leu | Ala | Gly<br>370 | Leu | |
| CTG | GGG | AGC | CCC | CTG | GGC | ACT | GCA | TCC | AGC | TTC | CCC | AAC | GTA | GGC | ACA | 1208 |
| Leu | Gly | Ser | Pro<br>375 | Leu | Gly | Thr | Ala | Ser<br>380 | Ser | Phe | Pro | Asn | Val<br>385 | Gly | Thr | |
| GTG | AGT | CTT | TTT | CAG | ACT | GGC | TCT | CGG | AGA | GTG | GCC | CAC | CTA | GTG | GGG | 1256 |
| Val | Ser | Leu<br>390 | Phe | Gln | Thr | Gly | Ser<br>395 | Arg | Arg | Val | Ala | His<br>400 | Leu | Val | Gly | |
| TTG | TTC | TGC | ATG | GGG | CTT | GGG | CTC | TCC | CCA | AGG | CTG | GCT | CAG | CTA | TTT | 1304 |
| Leu | Phe<br>405 | Cys | Met | Gly | Leu | Gly<br>410 | Leu | Ser | Pro | Arg | Leu<br>415 | Ala | Gln | Leu | Phe | |
| ACC | AGC | ATC | CCA | CTG | CCT | GTG | CTT | GGT | GGG | GTA | CTG | GGA | GTG | ACC | CAG | 1352 |
| Thr<br>420 | Ser | Ile | Pro | Leu | Pro<br>425 | Val | Leu | Gly | Gly | Val<br>430 | Leu | Gly | Val | Thr | Gln<br>435 | |
| GCT | GTA | GTT | CTG | TCT | GCT | GGA | TTC | TCC | AGC | TTT | CAC | CTG | GCT | GAC | ATT | 1400 |
| Ala | Val | Val | Leu | Ser<br>440 | Ala | Gly | Phe | Ser | Ser<br>445 | Phe | His | Leu | Ala | Asp<br>450 | Ile | |
| GAC | TCT | GGG | CGA | AAT | GTC | TTC | ATC | GTG | GGC | TTC | TCC | ATC | TTC | ATG | GCG | 1448 |
| Asp | Ser | Gly | Arg<br>455 | Asn | Val | Phe | Ile | Val<br>460 | Gly | Phe | Ser | Ile | Phe<br>465 | Met | Ala | |
| TTG | CTT | TTG | CCA | AGG | TGG | CTC | AGG | GAA | GCC | CCA | GTC | CTG | CTC | AAC | ACA | 1496 |
| Leu | Leu | Leu<br>470 | Pro | Arg | Trp | Leu | Arg<br>475 | Glu | Ala | Pro | Val | Leu<br>480 | Leu | Asn | Thr | |
| GGC | TGG | AGC | CCC | CTG | GAT | ATG | TTT | CTT | CGT | TCT | TTG | CTG | GCA | GAA | CCC | 1544 |
| Gly | Trp | Ser<br>485 | Pro | Leu | Asp | Met<br>490 | Phe | Leu | Arg | Ser | Leu<br>495 | Leu | Ala | Glu | Pro | |

TABLE 2-continued

Nucleotide sequence encoding a mouse nucleobase permease, and the predicted amino acid sequence of the resulting product. Designated SEQ ID NO: 1 and 2.

| ATT | TTC | TTA | GCT | GGT | CTA | CTG | GGC | TTT | CTC | CTA | GAA | AAC | ACT | ATA | TCT | 1592 |
|---|---|---|---|---|---|---|---|---|---|---|---|---|---|---|---|---|
| Ile | Phe | Leu | Ala | Gly | Leu | Leu | Gly | Phe | Leu | Leu | Glu | Asn | Thr | Ile | Ser | |
| 500 | | | | | 505 | | | | | 510 | | | | | 515 | |
| GGT | ACA | CGG | GCT | GAG | AGA | GGC | TTA | GGT | CAG | AGG | CTG | CCA | ACT | TCT | TTC | 1640 |
| Gly | Thr | Arg | Ala | Glu | Arg | Gly | Leu | Gly | Gln | Arg | Leu | Pro | Thr | Ser | Phe | |
| | | | | 520 | | | | | 525 | | | | | 530 | | |
| ACT | GCC | CAA | GAA | ATT | CAA | ATG | CTT | CAG | CAA | TCC | AGG | AGG | AAA | GCT | GCT | 1688 |
| Thr | Ala | Gln | Glu | Ile | Gln | Met | Leu | Gln | Gln | Ser | Arg | Arg | Lys | Ala | Ala | |
| | | | 535 | | | | | 540 | | | | | 545 | | | |
| CAA | GAG | TAT | GGG | CTT | CCT | TTA | CCC | ATC | AAA | AAC | CTG | TGT | TCC | TGC | ATC | 1736 |
| Gln | Glu | Tyr | Gly | Leu | Pro | Leu | Pro | Ile | Lys | Asn | Leu | Cys | Ser | Cys | Ile | |
| | | 550 | | | | | 555 | | | | | 560 | | | | |
| CCA | CAG | CCT | CTC | CAC | TGC | CTC | TGT | CCA | ATG | CCT | GAA | GAC | TCT | GGG | GAT | 1784 |
| Pro | Gln | Pro | Leu | His | Cys | Leu | Cys | Pro | Met | Pro | Glu | Asp | Ser | Gly | Asp | |
| | 565 | | | | | 570 | | | | | 575 | | | | | |
| GAA | GGA | GGA | TCC | TCT | AAA | ACA | GGA | GAG | AGA | GCC | GAC | TTG | TTG | CCT | AAC | 1832 |
| Glu | Gly | Gly | Ser | Ser | Lys | Thr | Gly | Glu | Arg | Ala | Asp | Leu | Leu | Pro | Asn | |
| 580 | | | | | 585 | | | | | 590 | | | | | 595 | |
| TCT | GGG | GAA | TCG | TAC | TCC | ACA | GCT | AGC | AGA | GAA | GGG | GTT | AGG | TCC | CAG | 1880 |
| Ser | Gly | Glu | Ser | Tyr | Ser | Thr | Ala | Ser | Arg | Glu | Gly | Val | Arg | Ser | Gln | |
| | | | | 600 | | | | | 605 | | | | | 610 | | |

TAATCATCAA GACCACCATT TTTGTCTTAG TTTAGCAGTA ACTGCCACCT TGCTGGAGTC 1940

TGTATACTTT GTCCCAGTGG AGGTGGATGT GGCCCACTTG CAAAATGGGC TGCCTTTCCT 2000

CCTCTTAAGA CTTGAGCAGA GGCCATGGTT TAGCGGGTTG GAACTGAATA AATGAGATTT 2060

CTGCCTGTAA AAAAAAAAAA AAAAA 2085 form 5

| CC | ACG | CGT | CCG | CCC | ACC | TGC | TGC | TGC | TTC | ATG | GTC | TTC | CCC | CaG | GAG | 47 |
|---|---|---|---|---|---|---|---|---|---|---|---|---|---|---|---|---|
| | Thr | Arg | Pro | Pro | Thr | Cys | Cys | Cys | Phe | Met | Val | Phe | Pro | Gln | Glu | |
| | | | | | | | | | 1 | | | | | 5 | | |
| GGC | TCT | CAT | ACC | CAC | CCG | CTC | AGC | TCC | CAG | | | | | | | 77 |
| Gly | Ser | His | Thr | His | Pro | Leu | Ser | Ser | Gln | | | | | | | |
| | | | 10 | | | | | 15 | | | | | | | | |

TAATCATCAA GACCACCATT TTTGTCTTAG T 108

The mouse sequence provided here contains sequences corresponding to twelve putative transmembrane (TM) segments, based upon a hydropathic analysis. These segments correspond to hydrophobic stretches which run from amino acids 59–78 (TM1); 111–130 (TM2); 169–189 (TM3); 192–212 (TM4); 219–238 (TM5); 267–289 (TM6) 319–340 (TM7); 363–383 (TM8); 393–413 (TM9); 421–441 (TM10); 456–473 (TM11); and 494–514 (TM12). An additional segment designated X corresponds to amino acids 89–107 appears to correspond to an insertion into a canonical motif found in a fold of the protein which is conserved in other nucleobase permeases. It may also be a membrane associated segment.

The purified protein, or proteins comprising a plurality of non-overlapping segments of at least about 8 amino acids therefrom, or defined peptides are useful for generating antibodies by standard methods, as described above. Synthetic peptides or purified protein can be presented to an immune system to generate a specific binding composition, e.g., monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press.

For example, the specific binding composition could be used for screening of an expression library made from a cell line which expresses a clone encoding a nucleobase permease. The screening can be standard staining of surface expressed protein, or by panning. Screening of intracellular expression can also be performed by various staining or immunofluorescence procedures. The binding compositions could be used to affinity purify or sort out cells expressing the protein. The binding compositions may also be useful in determining qualitative and quantitative expression levels of the proteins in various biological samples, including, e.g., cell types or tissues.

This invention contemplates use of isolated DNA or fragments to encode a structurally related, e.g., antigenically related, or biologically active, e.g., substrate binding or transporting, nucleobase permease or polypeptide fragment thereof. In addition, this invention covers isolated or recombinant DNA which encodes a structurally related or biologically active protein or polypeptide and which is capable of hybridizing under appropriate conditions with the DNA sequences described herein. Said biologically active protein or polypeptide can be an intact antigen, or fragment, and have an amino acid sequence as disclosed in Table 2. Further, this invention covers the use of isolated or recombinant DNA, or fragments thereof, which encode proteins which are homologous to a nucleobase permease or which were isolated using cDNA encoding a nucleobase permease as a probe. Preferably such homologous genes or proteins will be natural forms isolated from other vertebrates, e.g., warm blooded animals, including mammals, such as primates. The isolated DNA can have the respective regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The term embraces a nucleic acid sequence which has been removed from its naturally occurring intracellular environment, and includes recombinant or cloned DNA isolates and chemically synthesized analogs or analogs biologically synthesized by heterologous systems. A substantially pure molecule includes once or currently isolated forms of the molecule. Alternatively, a purified species may be separated from host components from a recombinant expression system.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides. Additional preferred embodiments will include lengths in excess of those numbers, e.g., 63, 72, 87, 96, 105, 117, etc. Said fragments may have termini at any pairs of locations, but especially at boundaries between structural domains, e.g., membrane spanning portions.

A DNA which codes for a nucleobase permease will be particularly useful to identify genes, mRNA, and cDNA species which code for related or homologous proteins, as well as DNAs which code for homologous proteins. There are likely homologues in other primates, and cross-species hybridization to DNAs has been observed in monkey, rat, dog, cow, human, and rabbit. Various additional nucleobase permeases should be homologous to a detectable extent using available technology, e.g., hybridization and/or PCR techniques, and are encompassed herein. However, even proteins that have a more distant evolutionary relationship to the antigen can readily be isolated under appropriate conditions using these sequences if they are sufficiently homologous in selected regions. Primate nucleobase permeases are of particular interest, including allelic or polymorphic variants found naturally.

This invention further covers recombinant DNA molecules and fragments having a DNA sequence identical to or highly homologous to the isolated DNAs set forth herein. In particular, the sequences will often be operably linked to DNA segments which control transcription, translation, and DNA replication. Alternatively, recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology* Academic Press, San Diego, pp. 1502–1504; Travis (1992) *Science* 256:1392–1394; Kuhn et al. (1991) *Science* 254:707–710; Capecchi (1989) *Science* 244:1288; Robertson (1987)(ed.) *Teratocarcinomas and Embryonic Stem Cells: A Practical Approach* IRL Press, Oxford; and Rosenberg (1992) *J. Clinical Oncology* 10:180–199; each of which is incorporated herein by reference.

Homologous nucleic acid sequences, when compared, exhibit significant sequence identity or similarity. The standards for homology in nucleic acids are either measures for homology generally used in the art by sequence comparison or based upon hybridization conditions. The hybridization conditions are described in greater detail below.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial homology exists when the segments will hybridize under selective hybridization conditions, to a strand, or its complement, typically using a sequence derived from Table 2, e.g., SEQ ID NO: 1. Typically, selective hybridization will occur when there is at least about 55% homology over a stretch of at least about 14 nucleotides, preferably at least about 65%, more preferably at least about 75%, and most preferably at least about 90%. See, Kanehisa (1984) *Nuc. Acids Res.* 12:203–213. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides. The endpoints of the segments may be at many different pair combinations.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is much more important than the measure of any single parameter. See, e.g., Wetmur and Davidson (1968) *J. Mol. Biol.* 31:349–370.

III. Purified Nucleobase Permease

The predicted sequence of mouse nucleobase permease amino acid sequence is shown in Table 2. The peptide sequences allow preparation of peptides to generate antibodies to recognize such segments, and various different methods may be used to prepare such peptides. As used herein, nucleobase permease shall encompass, when used in a protein context, a protein having an amino acid sequence shown in Table 2, or a significant fragment of such a protein. It also refers to a vertebrate, e.g., mammal, including human, derived polypeptide which exhibits similar biological function, e.g., antigenic, or interacts with nucleobase permease specific binding components, e.g., specific antibodies. These binding components, e.g., antibodies, typically bind to a nucleobase permease with high affinity, e.g., at least about 100 nM, usually better than about 30 nM, preferably better than about 10 nM, and more preferably at better than about 3 nM. Still higher affinities are possible, e.g., 100 pM, 30 pM, 100 fM, etc.

The term polypeptide, as used herein, includes a significant fragment or segment, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids. The segments may have lengths of at least 37, 45, 53, 61, 70, 80, 90, etc., and often will encompass a plurality of such matching sequences. The specific ends of such a segment will be at any combinations within the protein. Preferably the fragment will encompass structural domains, e.g., 1–58, 59–78, 79–88, 89–107, 11–130, 131–168, 169–189, 192–212, 213–218, 219–238, 239–266, 267–289, 290–318, 319–340, 341–362, 363–383, 384–392, 393–413, 414–420, 421–441, 442–455, 456–473, 474–493, 494–514, 515–537, and/or 538–611. Particular forms which are encoded by specific transcripts are found in cells, e.g., forms 1, 2, 3, 4, and 5.

Substantially pure, in the polypeptide context, typically means that the protein is free from other contaminating proteins, nucleic acids, and other biologicals derived from the original source organism or cell. Purity may be assayed by standard methods, and will ordinarily be at least about 40% pure., more ordinarily at least about 50% pure, generally at least about 60% pure, more generally at least about 70% pure, often at least about 75% pure, more often at least about 80% pure, typically at least about 85% pure, more typically at least about 90% pure, preferably at least about 95% pure, more preferably at least about 98% pure, and in most preferred embodiments, at least 99% pure. The analysis may be weight or molar percentages, evaluated, e.g., by gel staining, spectrophotometry, or terminus labeling.

A binding composition refers to molecules that bind with specificity to a nucleobase permease, e.g., in a substrate-receptor type fashion, an antibody-antigen interaction, or compounds, e.g., proteins which specifically associate with nucleobase permease, e.g., in a natural physiologically relevant protein-protein interaction, either covalent or non-covalent. The molecule may be a polymer, or chemical reagent. The interaction should exhibit some form of nucleobase specificity, e.g., specific affinity. A functional analog may be a protein with structural modifications, or may be a wholly unrelated molecule, e.g., which has a molecular shape which interacts with the appropriate binding determinants. The proteins may serve as agonists or antagonists of a receptor, see, e.g., Goodman et al. (eds.) (1990) *Goodman & Gilman's: The Pharmacological Bases of Therapeutics* (8th ed.), Pergamon Press.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength where advantageous. The actual ions may be modified, e.g., to conform to standard buffers used in physiological or analytical contexts.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS or CHAPS, or a low enough concentration as to avoid significant disruption of structural or physiological properties of the antigen.

Solubility is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W. H. Freeman; and Cantor and Schimmel (1980) *Biophysical Chemistry*, parts 1–3, W. H. Freeman & Co., San Francisco; each of which is hereby incorporated herein by reference. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S.

IV. Making Nucleobase Permease; Mimetics DNA which encodes the nucleobase permease or fragments thereof can be obtained by chemical synthesis, screening cDNA libraries, or by screening genomic libraries prepared from a variety of cell lines or tissue samples.

This DNA can be expressed in a wide variety of host cells for the synthesis of a full-length protein or fragments which can in turn, for example, be used to generate polyclonal or monoclonal antibodies; for binding studies; for construction and expression of modified molecules; and for structure/function studies. Each antigen or its fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, or portions thereof, may be expressed as fusions with other proteins.

Expression vectors are typically self-replicating DNA or RNA constructs containing the desired antigen gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention contain DNA which encodes a nucleobase permease, or a fragment thereof, typically encoding a biologically active polypeptide. The DNA can be under the control of a viral promoter and can encode a selection marker. This invention further contemplates use of such expression vectors which are capable of expressing eukaryotic CDNA coding for a Nucleobase permease in a prokaryotic or eukaryotic host, where the vector is compatible with the host and where the eukaryotic cDNA coding for the antigen is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the antigen or its fragments in various hosts using vectors that do not contain a replication origin that is recognized by the host cell. It is also possible to use vectors that cause integration of a nucleobase permease gene or its fragments into the host DNA by recombination, or to integrate a promoter which controls expression of an endogenous gene.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels et al. (1985 and Supplements) *Cloning Vectors: A Laboratory Manual*, Elsevier, N.Y., and Rodriquez et al. (1988)(eds.) *Vectors: A Survey of Molecular Cloning Vectors and Their Uses*, Buttersworth, Boston, Mass., which are incorporated herein by reference.

Transformed cells include cells, preferably mammalian, that have been transformed or transfected with vectors containing a nucleobase permease gene, typically constructed using recombinant DNA techniques. Transformed host cells usually express the antigen or its fragments, but for purposes of cloning, amplifying, and manipulating its DNA, do not need to express the protein. This invention further contemplates culturing transformed cells in a nutrient medium, thus permitting the protein, or soluble fragments, to accumulate in the culture. Soluble protein can be recovered, either from the culture or from the culture medium, and membrane associated proteins may be prepared from suitable cell subfractions.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and Pichia, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the nucleobase permease or its fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses*, Buttersworth, Boston, Chapter 10, pp. 205–236, which is incorporated herein by reference.

Lower eukaryotes, e.g., yeasts and Dictyostelium, may be transformed with vectors encoding vertebrate nucleobase permeases. For purposes of this invention, the most common lower eukaryotic host is the baker's yeast, *Saccharomyces cerevisiae*. It will be used to generically represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are the preferred host cells for expression of the functionally active nucleobase permease. In principle, any higher eukaryotic tissue culture cell line is workable, e.g., insect baculovirus expression systems, whether from an invertebrate or vertebrate source. However, mammalian cells are preferred, in that the processing, both cotranslationally and posttranslationally is more likely to simulate natural forms. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama et al. (1985)*Mol. Cell Biol.* 5:1136–1142; pMClneo Poly-A, see Thomas et al. (1987) *Cell* 51:503–512; and a baculovirus vector such as pAC 373 or pAC 610.

It will often be desired to express a vertebrate nucleobase permease polypeptide in a system which provides a specific desired or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the nucleobase permease gene may be cotransformed with one or more genes encoding mammalian or other glycosylating enzymes. Using this approach, certain mammalian glycosylation patterns will be achievable or approximated in prokaryote or other cells.

The nucleobase permease, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427–454; Tse et al. (1985) *Science* 230:1003–1008; and Brunner et al. (1991) *J. Cell Biol.* 114:1275–1283. Alternatively, the protein may be prepared in liposomes or other membrane-rich structures.

Now that the nucleobase permease has been characterized, fragments or derivatives thereof can be prepared by conventional processes for synthesizing peptides. These include processes such as are described in Stewart and Young (1984) Solid Phase *Peptide Synthesis*, Pierce Chemical Co., Rockford, Ill.; Bodanszky and Bodanszky (1984) *The Practice of Peptide Synthesis*, Springer-Verlag, New York; and Bodanszky (1984) *The Principles of Peptide Synthesis*, Springer-Verlag, New York. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The nucleobase permease, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction are typically protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tertalkyloxycarbonyl-hydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield et al. (1963) in *J. Am. Chem. Soc.* 85:2149–2156, which is incorporated herein by reference.

The prepared protein and fragments thereof can be isolated and purified from the reaction mixture by means of peptide separation, for example, by extraction, precipitation, electrophoresis and various forms of chromatography, and the like. The nucleobase permeases of this invention can be obtained in varying degrees of purity depending upon its desired use. Purification can be accomplished by use of the protein purification techniques disclosed herein or by the use of the antibodies herein described in immunoabsorbant affinity chromatography. This immunoabsorbant affinity chromatography is carried out by first linking the antibodies to a solid support and then contacting the linked antibodies with solubilized lysates of appropriate source cells, lysates of other cells expressing the protein, or lysates or supernatants of cells producing the nucleobase permease as a result of DNA techniques, see below. Detergents may be necessary to include in the methods to maintain protein solubility.

V. Physical Variants

This invention also encompasses proteins or peptides having substantial amino acid sequence homology with the amino acid sequence of a natural nucleobase permease. The variants include species and polymorphic variants.

Amino acid sequence homology, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are typically intended to include natural allelic and interspecies variations in each respective protein sequence. Typical homologous proteins or peptides will have from 25–100% homology (if gaps can be introduced), to 50–100% homology (if conservative substitutions are included) with the amino acid sequence of the Nucleobase permease. Homology measures will be at least about 35%, generally at least 40%, more generally at least 45%, often at least 50%, more often at least 55%, typically at least 60%, more typically at least 65%, usually at least 70%, more usually at least 75%, preferably at least 80%, and more preferably at least 80%, and in particularly preferred embodiments, at least 85% or more. See also Needleham et al. (1970) *J. Mol. Biol.* 48:443–453; Sankoff et al. (1983) Chapter One in *Time Warps. String Edits, and Macromolecules: The Theory and Practice of Sequence Comparison* Addison-Wesley, Reading, Mass.; and software packages from IntelliGenetics, Mountain View, Calif.; and the University of Wisconsin Genetics Computer Group, Madison, Wis.; each of which is incorporated herein by reference.

The isolated DNA encoding a nucleobase permease can be readily modified by nucleotide substitutions, nucleotide deletions, nucleotide insertions, and inversions of nucleotide stretches. These modifications result in novel DNA sequences which encode these antigens, their derivatives, or proteins having similar physiological, immunogenic, or antigenic activity. These modified sequences can be used to produce mutant antigens or to enhance expression. Enhanced expression may involve gene amplification, increased transcription, increased translation, and other mechanisms. Such mutant nucleobase permease derivatives include predetermined or site-specific mutations of the respective protein or its fragments. "Mutant nucleobase permease" encompasses a polypeptide otherwise falling within the homology definition of the mouse nucleobase permease as set forth above, but having an amino acid sequence which differs from that of nucleobase permease as found in nature, whether by way of deletion, substitution, or insertion. In particular, "site specific mutant nucleobase permease" generally includes proteins having significant homology with a protein having sequences of Table 2, and as sharing various biological activities, e.g., antigenic, immunogenic, nucleobase binding, or permease, with those sequences, and in preferred embodiments contain most of the disclosed sequences. Similar concepts apply to different nucleobase permeases, particularly those found in various mammals, e.g., primates, including human. As stated before, it is emphasized that descriptions are generally meant to encompass many different vertebrate nucleobase permeases, not limited to the specific embodiment disclosed in SEQ ID NO: 2.

Although site specific mutation sites are predetermined, mutants need not be site specific. Nucleobase permease mutagenesis can be conducted by making amino acid insertions or deletions. Substitutions, deletions, insertions, or any combinations may be generated to arrive at a final construct. Insertions include amino- or carboxy- terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also Sambrook et al. (1989) and Ausubel et al. (1987 and Supplements).

The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with a nucleobase permease polypeptide is a continuous protein molecule having sequences fused in a typical peptide linkage, typically made as a single translation product and exhibiting properties derived from-each source peptide. A similar concept applies to heterologous nucleic acid sequences.

In addition, new constructs may be made from combining similar functional domains from other proteins. For example, antigen-binding or other segments may be "swapped" between different new fusion polypeptides or fragments. See, e.g., Cunningham et al. (1989) *Science* 243:1330–1336; and O'Dowd et al. (1988) *J. Biol. Chem.* 263:15985–15992, each of which is incorporated herein by reference. Thus, new chimeric polypeptides exhibiting new combinations of specificities will result from the functional linkage of biologically relevant domains and other functional domains.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

VI. Functional Variants

In particular, variants with modified biological activities are desired. Variants which exhibit modified substrate binding affinity would be useful, e.g., with higher nucleobase binding affinity, or faster rate of permease or transport of the nucleobase. Variants with modified, preferably increased, rate of transfer of chemotherapeutic nucleobase analogs into a cell are potential gene therapy reagents to be administered in combination with the analog to specifically affect transformed cells, e.g., with respect to its nucleic acid metabolism.

The blocking of the biological function provided by nucleobase permeases could cause alterations in growth which require the nucleobase in metabolic processes. The permease may be useful in increasing the transport of desired nucleobase or nucleoside analogs into a cell, e.g., AZT into an HIV infected cell. Alternatively, blockers may prevent uptake of necessary metabolites for rapidly growing cells, e.g., in acute leukemia. Antisense nucleic acids may also be useful in blocking expression and function, e.g., in appropriate cell types. In vitro assays of the present invention will often use isolated protein, membranes from cells expressing a recombinant membrane associated nucleobase permease, soluble fragments comprising binding segments, or fragments attached to solid phase substrates. These assays will also allow for the diagnostic determination of the effects of either nucleobase binding segment mutations and modifications, or protein mutations and modifications, e.g., analogues.

This invention also contemplates the use of competitive drug screening assays, e.g., where neutralizing antibodies to the protein can compete with a test compound for binding to the protein. In this manner, the antibodies can be used to occupy binding sites on the protein that might otherwise interact with a nucleobase substrate.

Additionally, neutralizing antibodies against the nucleobase permease may function to block the metabolic processes dependent upon the permease, e.g., growth or metabolite availability. This may be important in growth of various tissue types, either normal or abnormal. Its tissue localization suggests that the permease may have a role in transporting nucleobases from the yolk substance across the endothelial layers of the embryo to the mesoderm layers which produce, e.g., hematopoietic cells and related proteins. Alternatively, soluble fragments of the permease, e.g., the 16 amino acid form 5 version, may exhibit hormone-like effects on various cell types.

"Derivatives" of the nucleobase permease include amino acid sequence mutants, glycosylation variants, and covalent or aggregate conjugates with other chemical moieties. Covalent derivatives can be prepared by linkage of functionalities to groups which are found in the nucleobase permease amino acid side chains or at the N- or C- termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the nucleobase permease or fragments thereof with other proteins or polypeptides, e.g., other membrane proteins. These derivatives can be synthesized in recombinant culture such as N- or C-terminal fusions or by the use of agents known in the art for their usefulness in cross-linking proteins through reactive side groups. Preferred antigen derivatization sites with cross-linking agents are at free amino groups, carbohydrate moieties, and cysteine residues.

Fusion polypeptides between the nucleobase permeases and other homologous or heterologous proteins are also provided. Homologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of aa antigen, e.g., a receptor-binding segment, so that the presence or location of the fused antigen may be easily determined. See, e.g., Dull et al., U.S. Pat. No. 4,859,609, which is hereby incorporated herein by reference. Other gene fusion partners include bacterial β-galactosidase, trpE, Protein A, β-lactamase, alpha amylase, alcohol dehydrogenase, and yeast alpha mating factor. See, e.g., Godowski et al. (1988) *Science* 241:812–816.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, for example, in Sambrook et al. (1989) *Molecular Cloning: A Laboratory Manual* (2d ed.), Vols. 1–3, Cold Spring Harbor Laboratory, which are incorporated herein by reference. Techniques for synthesis of polypeptides are described, for example, in Merrifield (1963) *J. Amer. Chem. Soc.* 85:2149–2156; Merrifield (1986) *Science* 232: 341–347; and Atherton et al. (1989) *Solid Phase Peptide Synthesis: A Practical Approach*, IRL Press, Oxford.

This invention also contemplates the use of derivatives of the nucleobase permeases other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, e.g., with cell membranes. Such covalent or aggregative derivatives are useful as immunogens, as reagents in immunoassays, or in purification methods such as for affinity purification of antigens or other binding proteins. For example, a nucleobase permease can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-nucleobase permease antibodies or its receptor or other binding partner. The permease can also be labeled with a detectable group, for example radioiodinated by the chloramine T procedure, covalently bound to rare earth chelates, or conjugated to another fluorescent moiety for use in diagnostic assays. Purification of nucleobase permease may be effected by immobilized antibodies or binding partners.

A solubilized nucleobase permease or fragment, including fragment concatemers, of this invention can be used as an immunogen for the production of antisera or antibodies specific for the protein or fragments thereof. The purified antigen can be used to screen monoclonal antibodies or binding fragments prepared by immunization with various forms of impure preparations containing the protein. In particular, the term "antibodies" also encompasses antigen binding fragments of natural antibodies. The purified nucleobase permeases can also be used as a reagent to detect any antibodies generated in response to the presence of elevated levels of the protein or cell fragments containing the antigen, both of which may be diagnostic of an abnormal or specific physiological or disease condition. Additionally, permease fragments may also serve as immunogens to produce the antibodies of the present invention, as described immediately below. For example, this invention contemplates antibodies raised against amino acid sequences encoded by nucleotide sequences shown in Table 2, or fragments of proteins containing them. In particular, this invention contemplates antibodies having binding affinity to or being raised against specific fragments which are predicted to lie outside of the lipid bilayer.

The invention also provides means to isolate a group of related permeases, e.g., vertebrate, displaying both distinctness and similarities in structure, expression, and function. Elucidation of many of the physiological effects of the antigens will be greatly accelerated by the isolation and characterization of distinct species variants. In particular, the present invention provides useful probes for identifying additional homologous genetic entities in different species. The results described above indicate that sufficiently homologous genes exist in other species that cross-species hybridization is likely to allow successful cloning.

The isolated genes will allow transformation of cells lacking expression of a corresponding nucleobase permease, e.g., either species types or cells which lack corresponding proteins and should exhibit negative background activity. Expression of transformed genes will allow isolation of antigenically pure cell lines, with defined or single specie variants. This approach will allow for more sensitive detection and discrimination of the physiological effects of nucleobase permeases. Subcellular fragments, e.g., cytoplasts or membrane fragments, can be isolated and used.

The genes may also be useful to increase transport of desired nucleobases into transformed cells. Thus, the permease may be transformed to cells for targeting of incorporation of desired substrates or analogs. For instance, it may be useful to incorporate specific modified nucleobases into those cells, which may become more susceptible to other treatments, or directly affected.

Dissection of the critical structural elements which effect the various physiological or differentiation functions provided by the proteins is possible using standard techniques of modern molecular biology, particularly in comparing members of the related class. See, e.g., the homolog-scanning mutagenesis technique described in Cunningham et al. (1989) Science 243:1339–1336; and approaches used in O'Dowd et al. (1988) J. Biol. Chem. 263:15985–15992; and Lechleiter et al. (1990) EMBO J. 9:4381–4390.

In particular, functional domains or segments can be substituted between species variants or related proteins to determine what structural features are important in both nucleobase binding affinity and specificity, as well as permease activity. An array of different variants will be used to screen for molecules exhibiting combined properties of interaction with different species variants.

Antigen internalization may occur under certain circumstances, and interaction between intracellular components and "extracellular" segments of proteins involved in interactions may occur. The specific segments of interaction of nucleobase permease with other intracellular components may be identified by mutagenesis or direct biochemical means, e.g., cross-linking or affinity methods. Structural analysis by crystallographic or other physical methods will also be applicable. Further investigation of the mechanism of biological function will include study of associated components which may be isolatable by affinity methods or by genetic means, e.g., complementation analysis of mutants.

Further study of the expression and control of nucleobase permease will be pursued. The controlling elements associated with the antigens may exhibit differential developmental, tissue specific, or other expression patterns. Upstream or downstream genetic regions, e.g., control elements, are of interest. For example, the permease tissue distribution seems to have highest mRNA levels in kidney, placenta, liver, bone marrow, thymus, spleen, lung, and some in testis. This distribution corresponds to organs with especially important ion exchange features, e.g., Na, K, or Ca, or in hematopoietic organs. Generally, the expression is higher in fibroblast and hematopoietic cells compared to neuronal cells.

Structural studies of the permease will lead to design of new variants, particularly analogues exhibiting modified binding affinity, or perhaps, altered rate of permease activity. This can be combined with previously described screening methods to isolate variants exhibiting desired spectra of activities. Alternatively, many different nucleobases and analogs thereof may be screened for either permease binding affinity or permease transfer. The permease may require a direct energy source, e.g., ATP or other nucleotide triphosphate, or may depend upon an ion gradient, as described above.

Expression in other cell types will often result in glycosylation differences in a particular antigen. Various species variants may exhibit distinct functions based upon structural differences other than amino acid sequence. Differential modifications may be responsible for differential function, and elucidation of the effects are now made possible.

Thus, the present invention provides important reagents related to nucleobase metabolism. Although the foregoing description has focused primarily upon the mouse nucleobase permease described in Table 2, those of skill in the art will immediately recognize that the invention encompasses other closely related antigens, e.g., other primate species or allelic variants, as well as variants and other members of the family.

VII. Antibodies

Antibodies can be raised to the various nucleobase permeases, including species or allelic variants, and fragments thereof, both in their naturally occurring forms and in their recombinant forms. Additionally, antibodies can be raised to nucleobase permeases in either their active forms or in their inactive forms. Anti-idiotypic antibodies are also contemplated.

Antibodies, including binding fragments and single chain versions, against predetermined fragments of the antigens can be raised by immunization of animals with conjugates of the fragments with immunogenic proteins. Monoclonal antibodies are prepared from cells secreting the desired antibody. These antibodies can be screened for binding to normal or defective nucleobase permeases, or screened for agonistic or antagonistic activity, e.g., blocking of binding of nucleobase, or alternatively, blocking other necessary aspects of transfer, e.g., blocking an energy requirement or ion pump function. These monoclonal antibodies will usually bind with at least a $K_D$ of about 1 mM, more usually at least about 300 $\mu$M, typically at least about 100 $\mu$M, more typically at least about 30 $\mu$M, preferably at least about 10 $\mu$M, and more preferably at least about 3 $\mu$M or better. More preferred embodiments may have even higher affinities, e.g., at least 300 nM, 30 nM, 3 nM, or perhaps even picomolar affinity.

The antibodies, including antigen binding fragments, of this invention can have significant diagnostic or therapeutic value. They can be potent blockers of nucleobase binding or transport, or may block the ability of the permease to effect a biological or biochemical response. They also can be useful as non-neutralizing antibodies and can be coupled to toxins or radionuclides so that when the antibody binds to the permease, a cell expressing it, e.g., on its surface, is killed. Further, these antibodies can be conjugated to drugs or other therapeutic agents, either directly or indirectly by means of a linker, and may effect drug targeting.

The antibodies of this invention can also be useful in diagnostic applications. As capture or non-neutralizing antibodies, they can be screened for ability to bind to the permeases without inhibiting binding by a partner antibody. As neutralizing antibodies, they can be useful in competitive binding assays. They will also be useful in detecting or quantifying nucleobase permease.

Permease fragments may be joined to other materials, particularly polypeptides, as fused or covalently joined polypeptides to be used as immunogens. An antigen and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York, and Williams et al. (1967) *Methods in Immunology and Immunochemistry*, Vol. 1, Academic Press, New York, each of which are incorporated herein by reference, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.) Academic Press, New York; and particularly in Kohler and Milstein (1975) in *Nature* 256: 495–497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse et al. (1989) "Generation of a Large Combinatorial Library of the Immunoglobulin Repertoire in Phage Lambda," *Science* 246:1275–1281; and Ward et al. (1989) *Nature* 341:544–546, each of which is hereby incorporated herein by reference. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567. These patents are incorporated herein by reference.

The antibodies of this invention can also be used for affinity chromatography in isolating the protein. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified nucleobase permease will be released.

The antibodies may also be used to screen expression libraries for particular expression products. Usually the antibodies used in such a procedure will be labeled with a moiety allowing easy detection of presence of antigen by antibody binding.

Antibodies raised against a nucleobase permease will also be useful to raise anti-idiotypic antibodies. These will be useful in detecting or diagnosing various conditions related to expression of the permease, and to metabolic disorders due to altered permease function.

VIII. Uses

The present invention provides reagents which will find use in diagnostic applications as described elsewhere herein, e.g., in the general description for physiological or developmental abnormalities, or below in the description of kits for diagnosis.

This invention also provides reagents with significant therapeutic value. A nucleobase permease (naturally occurring or recombinant), fragments thereof, and antibodies thereto, should be useful in the treatment of conditions associated with abnormal physiology or development, including abnormal proliferation, e.g., cancerous conditions, or degenerative conditions. Abnormal proliferation, regeneration, degeneration, and atrophy may be modulated by appropriate therapeutic treatment using the compositions provided herein. For example, a disease or disorder associated with abnormal function of a nucleobase permease should be a likely target for a substrate or blocking substrate. Alternatively, the permease may be a useful means for supplying important metabolites or metabolite blockers to the respective cells.

For example, transformation with the permease may increase availability of the substrate to the cell. In certain situations, a nucleobase analog might be advantageously supplied to the cell. The nucleobase analog might confer high susceptibility to further treatment, e.g., radiation sensitivity or otherwise, or may directly affect normal metabolism, e.g., nucleic acid related enzymes. Alternatively, the permease may be useful to screen for antagonists or inhibitors, which might be effective in blocking the normal availability to the cell of the natural substrate. Screening methods for such nucleobase analogs are provided.

Other abnormal developmental conditions are known in the cell types shown to possess nucleobase permease mRNA by Northern blot analysis, e.g., kidney, placenta, liver, bone marrow, thymus, spleen, lung, and testis. See Berkow (ed.) *The Merck Manual of Diagnosis and Therapy*, Merck & Co., Rahway, N.J.; and Thorn et al. *Harrison's Principles of Internal Medicine*, McGraw-Hill, N.Y. Many genetic diseases relevant to nucleic acid metabolism exhibit symptoms of immune system dysfunction, and immune function arises from hematopoietic cell development. These problems may be susceptible to prevention or treatment using compositions provided herein, or susceptible to regulation by modulating or controlling the nuclobase being supplied by the permease.

Recombinant antibodies which bind to a nucleobase permease can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Screening using nucleobase permease for binding metabolites or compounds having binding affinity to the permease can be performed, including isolation of associated components. Subsequent biological assays can then be utilized to determine if the compound has intrinsic biological activity and is therefore an agonist or antagonist in that it blocks an activity of the permease. In particular, nucleobase analogs may be useful in blocking binding of the natural target or otherwise blocking permease activity. Alternatively, various other analogs may be useful in blocking an ion transporter, or nucleotide triphosphate energy source. This invention further contemplates the therapeutic use of antibodies to nucleobase permease as antagonists. This approach should be particularly useful with other nucleobase permease species variants and other members of the family.

Antagonists of the permease activity, e.g., antibodies which block the transport, may be useful in various medical conditions. These would include intestinal, placenta, or kidney abnormalities, all of which are important organs where electrolyte balance and transfer of small molecules take place. Certain congenital diseases of nucleic acid metabolism will be susceptible to such a therapeutic approach. Many treatments also cause increased levels of uric acid in the body fluids, and means to prevent uptake of the molecule into cells will be valuable.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; each of which is hereby incorporated herein by reference. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

Nucleobase permease, fragments thereof, and antibodies to it or its fragments, antagonists, and nucleobase targets, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman et al. (eds.) (1990) *Goodman and Gilman's: The Pharmacological Bases of Therapeutics*, 8th Ed., Pergamon Press; and Remington's Pharmaceutical Sciences, 17th ed. (1990), Mack Publishing Co., Easton, Pa. The therapy of this invention may be combined with or used in association with other agents, e.g., chemotherapeutic or chemopreventive agents when used for such indications.

Both the naturally occurring and the recombinant form of nucleobase permeases of this invention are particularly useful in kits and assay methods which are capable of screening compounds for binding activity to the proteins. Several methods of automating assays have been developed in recent years so as to permit screening of tens of thousands of compounds in a short period. See, e.g., Fodor et al. (1991) *Science* 251:767–773, which is incorporated herein by reference and which describes means for testing of binding affinity by a plurality of defined polymers synthesized on a solid substrate. The development of suitable assays can be greatly facilitated by the availability of large amounts of purified, soluble nucleobase permease as provided by this invention.

This invention is particularly useful for screening compounds by using recombinant permease in any of a variety of drug screening techniques. The advantages of using a recombinant protein in screening for specific ligands or metabolite substrates include: (a) improved renewable source of the permease from a specific source; (b) potentially greater number of permease molecules per cell giving better signal to noise ratio in assays; and (c) species variant specificity (theoretically giving greater biological and disease specificity). The purified protein may be tested in numerous assays, typically in vitro assays, which evaluate biologically relevant responses. See, e.g., Coligan *Current Protocols in Immunology*; Hood et al. *Immunology* Benjamin/Cummings; Paul (ed.) *Fundamental Immunology*; and *Methods in Enzymology* Academic Press. This will also be useful in screening for nucleobases which bind a nucleobase permease, e.g., from an expressing cell.

One method of drug screening utilizes eukaryotic or prokaryotic host cells which are stably transformed with recombinant DNA molecules expressing the nucleobase permease. Cells may be isolated which express an antigen in isolation from other functionally equivalent antigens. Such cells, either in viable or fixed form, can be used for standard protein-protein binding assays. See also, Parce et al. (1989) *Science* 246:243–247; and Owicki et al. (1990) *Proc. Nat'l Acad. Sci. USA* 87:4007–4011, which are incorporated herein by reference and describe sensitive methods to detect cellular responses. Competitive assays are particularly useful, where the cells (source of nucleobase permease) are contacted and incubated with a labeled binding partner or antibody having known binding affinity to the permease, such as $^{125}$I-antibody, and a test sample whose binding affinity to the binding composition is being measured. The bound and free labeled binding compositions are then separated to assess the degree of antigen binding. The amount of test compound bound is inversely proportional to the amount of labeled receptor binding to the known source. Numerous techniques can be used to separate bound from free antigen to assess the degree of binding. This separation step could typically involve a procedure such as adhesion to filters followed by washing, adhesion to plastic followed by washing, or centrifugation of the cell membranes. Viable cells could also be used to screen for the effects of drugs on nucleobase permease mediated functions, e.g., ion exchange and/or nucleobase fluxes. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

Another method utilizes membranes from transformed eukaryotic or prokaryotic host cells as the source of the nucleobase permease. These cells are stably transformed with DNA vectors directing the expression of a membrane associated nucleobase permease, e.g., an engineered membrane bound form. Essentially, the membranes would be prepared from the cells and used in any permease/nucleobase substrate type binding assay such as a competitive assay set forth above.

Still another approach is to use solubilized, unpurified or solubilized, purified nucleobase permease from transformed eukaryotic or prokaryotic host cells. This allows for a "molecular" binding assay with the advantages of increased specificity, the ability to automate, and high drug test throughput. Various detergents may be necessary to maintain biological activities of the presumptive membrane protein.

Another technique for drug screening involves an approach which provides high throughput screening for compounds having suitable binding affinity to nucleobase permease and is described in detail in Geysen, European Patent Application 84/03564, published on Sep. 13, 1984, which is incorporated herein by reference. First, large numbers of different small peptide test compounds are synthesized on a solid substrate, e.g., plastic pins or some other appropriate surface, see Fodor et al. (1991). Then all the pins are reacted with solubilized, unpurified or solubilized, purified nucleobase permease binding composition, and washed. The next step involves detecting bound binding composition.

Rational drug design may also be based upon structural studies of the molecular shapes of the nucleobase permease and other effectors or analogues. Effectors may be other proteins which mediate other functions, e.g., regulatory proteins, or may be targets of permease binding or transport. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York.

Purified nucleobase permease can be coated directly onto plates for use in the aforementioned drug screening techniques, though membrane integration may be a strong consideration in the assay design. However, non-neutralizing antibodies to the permease can be used as capture antibodies to immobilize the protein on the solid phase.

The form 5 transcript suggests that a short peptide may be a physiological product. Means to test the 16mer for biological activity are available with the given sequence. Synthetic peptide would be made and its activity tested on various biological assays, e.g., on cells expected to have great need for nucleobases, including quickly dividing cell types in development, e.g., hematopoietic cells, see Coligan, gut cells, or neoplastic cells.

IX. Kits

This invention also contemplates use of nucleobase permeases, fragments thereof, peptides, and their fusion products in a variety of diagnostic kits and methods for detecting the presence of a binding composition. Typically the kit will have a compartment containing either a defined nucleobase permease peptide or gene segment or a reagent which recognizes one or the other, e.g., antigen fragments or antibodies.

A kit for determining the binding affinity of a test compound to a nucleobase permease would typically comprise a test compound; a labeled compound, e.g., an antibody having known binding affinity for the permease, or a nucleobase target substrate; a source of nucleobase permease (naturally occurring or recombinant); and a means for separating bound from free labeled compound, such as a solid phase for immobilizing the antigen. Once compounds are screened, those having suitable binding affinity to the permease can be evaluated in suitable biological assays, as are well known in the art, to determine whether they exhibit similar kinetics or specificity of activities to the normal compound. The availability of recombinant nucleobase permease polypeptides also provide well defined standards for calibrating such assays.

A preferred kit for determining the concentration of, for example, a nucleobase permease in a sample would typically comprise a labeled compound, e.g., antibody, having known binding affinity for the antigen, a source of antigen (naturally occurring or recombinant) and a means for separating the bound from free labeled compound, for example, a solid phase for immobilizing the nucleobase permease. Compartments containing reagents, and instructions, will normally be provided.

One method for determining the concentration of nucleobase permease in a sample would typically comprise the steps of: (1) preparing membranes from a sample comprised of a membrane bound nucleobase permease source; (2) washing the membranes and suspending them in a buffer; (3) solubilizing the permease by incubating the membranes in a culture medium to which a suitable detergent has been added; (4) adjusting the detergent concentration of the solubilized antigen; (5) contacting and incubating said dilution with radiolabeled antibody to form complexes; (6) recovering the complexes such as by filtration through polyethyleneimine treated filters; and (7) measuring the radioactivity of the recovered complexes.

Antibodies, including antigen binding fragments, specific for the nucleobase permease or fragments are useful in diagnostic applications to detect the presence of elevated levels of nucleobase permease and/or its fragments. Such diagnostic assays can employ lysates, live cells, fixed cells, immunofluorescence, cell cultures, body fluids, and further can involve the detection of antigens related to the protein in serum, or the like. Diagnostic assays may be homogeneous (without a separation step between free reagent and protein-protein complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to a Nucleobase permease or to a particular fragment thereof. Similar assays have also been extensively discussed in the literature. See, e.g., Harlow and Lane (1988) *Antibodies: A Laboratory Manual*, CSH.

Anti-idiotypic antibodies may have similar use to diagnose presence of antibodies against a Nucleobase permease, as such may be diagnostic of various abnormal states. For example, overproduction of nucleobase permease may reflect various medical conditions, which may be diagnostic of abnormal physiological states, particularly in proliferative cell conditions such as cancer or abnormal differentiation. For example, leukemias and lymphomas may exhibit altered permease expression, which may reflect their altered physiology and may provide means to selectively target.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled Nucleobase permease is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Any of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the antigen, test compound, nucleobase permease, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Both of the patents are incorporated herein by reference. Possibilities for indirect labeling include biotinylation of one constituent followed by binding to avidin coupled to one of the above label groups.

There are also numerous methods of separating the bound from the free permease, or alternatively the bound from the free test compound. The nucleobase permease can be immobilized on various matrixes followed by washing. Suitable matrixes include plastic such as an ELISA plate, filters, and beads. Methods of immobilizing the nucleobase permease to a matrix include, without limitation, direct adhesion to plastic, use of a capture antibody, chemical coupling, and biotin-avidin. The last step in this approach involves the precipitation of protein-protein complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle et al. (1984) *Clin. Chem.* 30:1457–1461, and the double antibody magnetic particle separation as described in U.S. Pat. No. 4,659,678.

The methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a nucleobase permease. These sequences can be used as probes for detecting levels of message in samples from patients suspected of having an abnormal condition, e.g., cancer or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$p. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR). Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet et al. (1989) *Progress in Growth Factor Res.* 1:89–97.

X. Methods for Isolating Nucleobase Permease Specific Binding Partners

The nucleobase permease should interact with a nucleobase substrate based, e.g., upon its similarity in structure and function to other permeases as described. Methods to identify a natural nucleobase substrate are made available by the ability to make purified membranes expressing a nucleobase permease for screening programs. Soluble or other constructs using the nucleobase permease sequences provided herein will allow for screening or isolation of various nucleobase or analog substrates.

The broad scope of this invention is best understood with reference to the following examples, which are not intended to limit the invention to specific embodiments.

EXAMPLES

I. General Methods

Some of the standard methods are described or referenced, e.g., in Maniatis et al. (1982) *Molecular Cloning, A Laboratory Manual*, Cold Spring Harbor Laboratory, Cold Spring Harbor Press; Sambrook et al. (1989) *Molecular Cloning: A Laboratory Manual*, (2d ed.), vols. 1–3, CSH Press, N.Y.; Ausubel et al., Biolocy, Greene Publishing Associates, Brooklyn, NY; or Ausubel et al. (1987 and Supplements) *Current Protocols in Molecular Biology*, Greene/Wiley, New York; Innis et al. (eds.)(1990) *PCR Protocols: A Guide to Methods and Applications* Academic Press, N.Y.; all of which are each incorporated herein by reference. Methods for protein purification include such methods as ammonium sulfate precipitation, column chromatography, electrophoresis, centrifugation, crystallization, and others. See, e.g., Ausubel et al. (1987 and periodic supplements); Deutscher (1990) "Guide to Protein Purification" in *Methods in Enzymology*, vol. 182, and other volumes in this series; and manufacturer's literature on use of protein purification products, e.g., Pharmacia, Piscataway, N.J., or Bio-Rad, Richmond, CA; which are incorporated herein by reference. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) Genetic Engineering Principle and Methods 12:87–98, Plenum Press, N.Y.; and Crowe et al. (1992) *OIAexpress: The High Level Expression & Protein Purification System* QUIAGEN, Inc., Chatsworth, Calif.: which are incorporated herein by reference.

FACS analyses are described in Melamed et al. (1990) *Flow Cytometry and Sorting* Wiley-Liss, Inc., New York, N.Y.; Shapiro (1988) *Practical Flow Cytometry* Liss, New York, N.Y.; and Robinson et al. (1993) *Handbook of Flow Cytometry Methods* Wiley-Liss, New York, N.Y.

The FASTA (Pearson and Lipman, 1988) and BLAST (Altschul, et al. (1990) *J. Mol. Biol.* 215:403–410) programs were used to comb nonredundant protein and nucleotide databases (Benson, et al. (1994) *Nucl. Acids Res.* 22:3441–3444; Bairoch and Boeckmann (1994) *Nucl. Acids Res.* 22:3578–3580) with the resultant CDNA and encoded protein sequences. The sensitive search strategies of Altschul, et al. (1994) *Nature Genet.* 6:119–129; and Koonin, et al. (1994) *EMBO J.* 13:493–503; served as examples of how to locate distant structural homologues of protein chains. Multiple alignments of collected homologues were carried out with ClustalW (Thompson, et al. (1994) *Comp. Applic. Biosci.* 10:19–29) and MACAW (Schuler, et al. (1991) *Proteins* 9:180–190).

The membrane topologies of Yspl1 and a cohort of putative homologues were analyzed by a variety of methods that sought to determine the consensus number of hydrophobic membrane-spanning helices and the likely cytoplasmic or extracellular exposure of the hydrophilic connecting loops. For single sequence analysis, the ALOM and MTOP (Klein, et al. (1985) *Biochim. Biophys. Acta* 815:468–476; and Hartmann, et al. (1989) *Proc. Natl. Acad. Sci. USA* 86:5786–5790) programs were accessed from the PSORT World-Wide Web site (Nakai and Kanehisa (1991) *Proteins* 11:95–110; and Nakai and Kanehisa (1992) *Genomics* 14:897–911); in turn, the TopPredII program (Claros and von Heijne (1994) *Comp. Applic. Biosci.* 10:685–686; MacIntosh PPC version) was used to parse chains into probable hydrophobic transmembrane and loop regions, and further predict the localization of these latter regions by prevalence of charged residue types (von Heijne (1992) *J. Mol. Biol.* 225:487–494; and Sippos and von Heijne (1993) *Eur. J. Biochem.* 213:1333–1340). MEMSAT (Jones, et al. (1994) *Biochem.* 33:3038–3049; MS-DOS PC version) was likewise used to fit individual sequences into statistically-based topology models that render judgment on membrane spanning and loop chain segments. Two Web-accessible programs that are able to make use of evolutionary data by analyzing multiply aligned sequences are PHD (Rost, et al. (1994) *Comp. Applic. Biosci.* 10:53–60; and Rost, et al. (1995) *Protein Sci.* 4:521–533) and TMAP (Persson and Argos (1994) *J. Mol. Biol.* 237:182–192); the former utilizes a neural network system to accurately predict the shared location of helical transmembrane segments in a protein family.

II. Preparation of Antibodies Specific for Nucleobase Permease

Balb/c mice are immunized with cells transformed with the gene, either endogenous or exogenous cells, or with isolated membranes enriched for expression of the permease. Splenocytes are fused with an appropriate fusion partner and hybridomas are selected in growth medium by standard procedures. Hybridoma supernatants are screened for the presence of antibodies which bind to the nucleobase permease, e.g., by ELISA or other assay.

In another method, synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. For shorter peptides, fusion of repeats will increase protein size. In appropriate situations, the binding reagent is either labeled as described above, e.g., fluorescence or otherwise, or immobilized to a substrate for panning methods. Nucleic acids may also be introduced into cells in an animal to produce the antigen, which serves to elicit an immune response. See, e.g., Wang, et al. (1993) *Proc. Natl. Acad. Sci.* 90:4156–4160; Barry, et al. (1994)

*BioTechniques* 16:616–619; and Xiang, et al. (1995) *Immunity* 2:129–135. A plasmid encoding the permease was introduced into an animal for the initial exposure. A protein boost was provided, and monoclonal antibodies prepared. These hybridoma products were tested and characterized for usefulness in immunoprecipitation, Western blot detection, and ELISA.

III. Distribution of Nucleobase Permease

The screening of a 8.5 day yolk sac cDNA library by hybridization with clone 240 led to the isolation of four different cDNAs: 240–7 (2.1 Kb), 240–205 (1.8 Kb), 240–4 (0.7 Kb) and 240–10B (0.6 Kb). The size of these cDNAs is in agreement with the Northern Blot Analysis results shown in FIG. 1 and correspond, respectively, to the proteins encoded by Forms 1, 2, 3 and 4 of Clone 240 shown in FIGS. 2A and 2B. The frequency of Clone 240 positive clones, all 4 cDNA forms together, was approximately $1/63,000$. Forms 3 and 4 cDNAs of Clone 240, undetectable in day 8.5 yolk sac by Northern analysis, were represented in the day 8.5 yolk sac-derived cDNA library with a frequency three times lower than that of Forms 1 and 2 cDNAs. The deduced protein sequence of the longer cDNA sequence of Clone 240–7 immediately revealed in the jagged contours of its hydropathic profile (Kyte and Doolittle (1982) *J. Mol. Biol.* 157:105–132) that it likely was an integral membrane protein with 10–13 transmembrane (TM) helices. Databank searching accordingly disclosed a faint but significant chain similarity to a family of nucleobase permeases described in bacteria and yeast (Diallinas, et al. (1995) *J. Biol. Chem.* 270:8610–8622 and Genbank Acc. # X79796) (FIG. 4). Due to its preferential expression in the yolk sac, we designated this novel gene product as Yolk sac permease-like molecule 1 (Yspl1), and its structure indicates that the label nucleobase permease is appropriate.

A. Direct protein detection by antibodies

Various cells, tissues, and developmental stages are stained with labeled antibodies. The detection may be immunohistochemical for solid tissue, by FACS in disperse cells, and by other appropriate methods for other sample types. Antibodies specific for the various forms may be used to distinguish between membrane associated and soluble fragments. Various amplification means may be coupled to increase sensitivity.

Specific immunohistochemistry was performed, and suggested protein expression on yolk sac, placenta, and fetal brain samples.

B. Detection of nucleic acids RNA was isolated from cells, embryonic tissues, and adult organs using RNAzol solution (Tel-test, Inc, Friendswood, Tex.) according to manufacturer's instructions. Heart and testis total RNAs were purchased from Clontech, Palo Alto, Calif.

Large amounts of plasmid DNA containing differential display PCR products were prepared using the QIAGEN Plasmid Maxi Kit (QIAGEN) following the manufacturer's instructions. Plasmid DNA was cut with EcoRI (Boehringer Mannheim) or BstXI (NE Biolabs, Mass.), gel extracted with the QIAEX gel extraction kit (QIAGEN) and random primed with [$^{32}$P]dCTP (Amersham) using the Prime-It II kit (Stratagene, La Jolla, Calif.), all in accordance with manufacturer's instructions.

10 to 20 $\mu$g of total RNA were run in formaldehyde gels and transferred to Nytran membranes (Schleicher & Schuell, Keene, NH) by standard methods, and blots were hybridized and washed at 65° C.

Various primers may be used to quantitate expression of message. Means to block DNA hybridization signal, or RNA isolation, will be applicable to quantitate roughly the amount of expression of appropriate RNAs.

C. Functional detection

Specific neutralizing antibodies should provide means to specifically block the biological activity of the nucleobase permease. Activities related to nucleobase binding, or to nucleobase transport may be measured by sensitive means based upon knowledge of the normal biological function of the various forms.

Further testing of populations of cells, e.g., hematopoietic progenitors, or of other cell or tissue types will be useful to further determine distribution and likely function. Other tissue types, at defined developmental stages, and pathology samples may be screened to determine whether pathological states or stages may be advantageously correlated with the biological activity of the permease.

IV Biochemical Characterization of the Nucleobase Permease

Constructs for the expression of Forms 3 and 4 of Yspl1 were made in which a tag (FLAG) sequence (Hopp, et al. (1988) Biotechnology (NY) 6:1205–1210) was introduced in the protein. The open reading frame of cDNAs 240–4 and 240–210B, corresponding to Forms 3 and 4 of Yspl1 was amplified by PCR to introduce the FLAG peptide sequence (IBI, New Haven, Conn.) at the C-terminus of both protein Forms 3 and 4. Appropriate primers were used for for Form 3 and Form 4. PFU enzyme (Stratagene) was used with 12 cycles PCR: 94° C. 30 sec; 55° C. 1 min; 72° C. 4 min. These constructs were cloned into a PME18X vector (DNAX) using XhoI and XbaI sites incorporated into the 5' and 3' primers, respectively.

COS-7 cells were maintained in DMEM, 10% FCS, 4 mM L-glutamine (JRH Biosciences, Lenexa, Kans.), 100 U/ml penicillin, and 100 $\mu$g/ml streptomycin. Plasmid DNA was transfected by electroporation (BIORAD, Hercules, Calif.) (20 $\mu$g/1×10$^7$ cells) and plated into tissue culture dishes. The medium was replaced after 24 hours and cell lysates and media were collected three days after transfection. Lysis buffer (25 mM Hepes pH 7.5, 2 mM EDTA, 1.0% NP-40, 150 mM NaCl, 0.01% Aprotinin (Sigma, St. Louis, Mo.), 0.01% Leupeptin (Sigma)) was added to the plates. Plates were kept on ice for 45 minutes. Lysates were centrifuged for 15 minutes to eliminate cell debris. Supernatants of centrifuged cell lysates and sterile-filtered media from cultured cells were incubated with anti-FLAG M2 Affinity Gel (IBI) at 4° C. overnight and washed four times with PBS. Immunoprecipitates were eluted in a Econocolumn (BIORAD) with 2.5M Glycine, pH 2.5. Eluates were neutralized with Hepes, pH 7.4 (JRH Biosciences) and concentrated by precipitation with 24% TCA and 2% deoxycholic sodium salt (Sigma). Pellets were eluted in 2×Sample Buffer (NOVEX, San Diego, Calif.), electrophoresed on 4–20% tris-glycine gels (Novex) and transferred to PVDF membranes (Immobilon-P, Millipore Corporation, Bedford, Mass.). Membranes were exposed to 3% non-fat milk for 1 h at 37° C. Anti-FLAG M2 antibody was used as recommended (IBI). Anti-mouse Ig horseradish peroxidase conjugate (Amersham) was used at 1:2,000 dilution and the peroxidase detection was performed with ECL detection reagents (Amersham).

Other fusion proteins can be produced, e.g., a recombinant nucleobase permease construct is prepared, e.g., as a fusion product with a useful affinity reagent, e.g., FLAG peptide. This peptide segment may be useful for purifying the expression product of the construct. See, e.g., Crowe, et al. (1992) *OIAexDress: The High Level Expression & Pro-* tein *Purification System* QUIAGEN, Inc. Chatsworth, Calif.; and Hopp, et al. (1988) *Bio/Technology* 6:1204–1210. Membranes comprising the permease are assayed to determine the natural nucleobase substrate. Most likely the nucleobase will be a uracil related nucleobase, but may also include, at various levels of efficiency of binding or transport, pyrimidine or purine analogs. See, e.g., Goodman and Gilman, *The Pharmacological Basis of Therapeutics*; Lukovics and Zablocka *Nucleoside Synthesis: Organosilicon Methods* Ellis Horwood, N.Y.; Townsend, *Chemistry of Nucleosides and Nucleotides*, vols 1–3, Plenum Press, N.Y.; Munch-Pertson (1983) Metabolism of Nucleotides, Nucleosides, and Nucleobases in *Microorcanisms* Academic Press, NY; Gehrke (1990) *Chromatography & Modification of Nucleosides* vols A, B, and C, Elsevier; Bloch (1975) *Chemistry, Biology, & Clinical Uses of Nucleoside Analogs* Annals NY Acad. Sci.; and Ulbricht (1964) *Purines, Pyrimidines, & Nucleotides* Franklin Co.

V. Purification of Nucleobase Permease

The nucleobase permease is isolated by a combination of affinity chromatography using the nucleobase permease specific binding compositions, e.g., antibody, as a specific binding reagent in combination with protein purification techniques allowing separation from other proteins and contaminants. Various detergent combinations may be tested to determine what combinations will retain biological activity while solubilising contaminants. The purification may follow biological activity, e.g., nucleobase binding or transport into membranes, or by ELISA or other structural binding reagents.

VI. Isolation of a CDNA Clone Encoding Nucleobase Permease

A. Antibodies and Flow-Cytometric Sorting

Expression cloning of cells transformed with an appropriate cDNA library may be sorted by FACS using antibody reagents described above. The sorted cells are isolated and expanded, and subjected to multiple selection cycles, leading to a high proportion of cells expressing the desired DNA.

B. Antibodies and Staining

The antibodies to nucleobase permease are used for screening of a library made from a cell line which expresses a nucleobase permease. Standard staining techniques are used to detect or sort intracellular or surface expressed ligand, or surface expressing transformed cells are screened by panning. Screening of intracellular expression is performed by various staining or immunofluorescence procedures. See also McMahan et al. (1991) *EMBO J.* 10:2821–2832.

For example, on day 0, precoat 2-chamber permanox slides with 1 ml per chamber of fibronectin, 10 ng/ml in PBS, for 30 min at room temperature. Rinse once with PBS. Then plate COS cells at $2-3 \times 10^5$ cells per chamber in 1.5 ml of growth media. Incubate overnight at 37° C.

On day 1 for each sample, prepare 0.5 ml of a solution of 66 $\mu$g/ml DEAE-dextran, 66 $\mu$M chloroquine, and 4 $\mu$g DNA in serum free DME. For each set, a positive control is prepared, e.g., of huIL-10-FLAG cDNA at 1 and 1/200 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3×with HBSS. The slides may be stored at −80° C. after all liquid is removed. For each chamber, 0.5 ml incubations are performed as follows. Add HBSS/saponin (0.1%) with 32 $\mu$/ml of 1M NaN$_3$ for 20 min. Cells are then washed with HBSS/saponin 1×. Soluble antibody is added to cells and incubate for 30 min. Wash cells twice with HBSS/saponin. Add second antibody, e.g., Vector anti-mouse antibody, at 1/200 dilution, and incubate for 30 min. Prepare ELISA solution, e.g., Vector Elite ABC horseradish peroxidase solution, and pre-incubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of H$_2$O$_2$ per 5 ml of glass distilled water. Carefully remove chamber and rinse slide in water. Air dry for a few minutes, then add 1 drop of Crystal Mount and a cover slip. Bake for 5 min at 85°–90° C.

Alternatively, the antibodies to nucleobase permeases are used to affinity purify or sort out cells expressing the antigen. See, e.g., Sambrook et al. or Ausubel et al, which are incorporated herein by reference. The antigen is typically expressed on the cell surface.

Hybridization approaches may also be utilized to find closely related variants of the antigen based upon nucleic acid hybridization.

VII. Measuring Binding of Nucleobases to the Permease

Recombinant permease is prepared in either cells lacking other permeases, or purified membranes. Binding of a substrate may be measured, e.g., as described in Zurawski and Zurawski (1992) *EMBO J.* 11:3905–3910, or on a BIAcore™ apparatus by techniques described in the manufacturer's manual, Pharmacia Biosensor. Screening for the natural substrate can be performed by methods as described, e.g., in Pajor and Wright (1992) *J. Biol. Chem.* 267:3557–3560. Screening for antagonists of various substrates can also be performed by standard procedures. Transport can also be measured across membranes, or into cells. Other necessary cofactors or energy sources may also be determined, e.g., ion gradient requirements, or energy requirements, e.g., ATP or other phosphorylated molecules.

All references cited herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

TABLE 3

Different cDNA forms of Yspl1; see SEQ ID NO: 1

Form 1 (240-7)

| | | | | | |
|---|---|---|---|---|---|
| CCCACGCGTC | CGCTGGGGCA | GCCAAGACGC | AATCAAGTCA | GGGCAGCATG | AGCCGATCAC |
| CTCTCCATCC | CATTCCACTT | CTATCTGAGG | GCTACCAGGA | TACCCCTGCT | CCCCTGCCAC |
| CACTGCTACC | CCCTCTCCAG | AATCCCTCCT | CCCGTTCTTG | GGCCTCTCGG | GTGTTTGGGC |
| CTTCCACCTG | GGGGCTCAGC | TGTCTTCTGG | CTCTACAGCA | TTTCCTGGTC | TTGGCATCTT |
| TGCTCTGGGC | CTCCCACCTG | CTGCTGCTTC | ATGGTCTTCC | CCCaGGAGGG | CTCTCATACC |
| CACCCGCTCA | GCTCCTGGCT | TCCAGTTTCT | TTTCATGTGG | CCTGTCTACG | GTCCTGCAGA |
| CTTGGATGGG | CAGCAGGCTA | CCTCTAATCC | AGGCTCCGTC | CCTAGAGTTT | CTTATCCCCG |
| CACTGGTGCT | GACAAACCAG | AAGCTACCTC | TGACGACCAA | GACACCTGGA | AATGCCTCCC |
| TCTCACTGCC | CCTGTGTAGT | TTGACAAGAA | GCTGCCATGG | CCTGGAGCTC | TGGAACACTT |
| CTCTCCGAGA | GGTGTCGGGG | GCAGTGGTGG | TGTCCGGGCT | GCTGCAGGGC | ACTATAGGAC |
| TTCTAGGGGT | GCCTGGCCGT | GTGTTCCCCT | CACTGGTGCTG | ACTGGTGCTG | GCTCCCAGCC |
| TGGTTGTGGC | AGGGCTTTCT | GCCCACAAGG | AGGTGGCCCA | GTTCTGTTCT | GCTcACTGGG |
| GCCTGGCCTT | GCTGCTCATC | CTGCTCATGG | TGGTATGCTC | TCAGCACCTG | GGTTCATGCC |
| AGATACCCCT | TTgCTCCTGG | AGGCCATCTT | CAACTTCAAC | TCACATTTGT | ATtCCCGTCT |
| TCCGACTCCT | TTCGGTGCTT | GCCCCTGTGG | CCTGTGTGTG | GTTCATCTCT | GCCTTTGTGG |
| GTACGAGTGT | TATCCCTCTG | CAGCTGTCTG | AGCCCTCGGA | TGCACCTTGG | TTTTGGCTGC |
| CACACCCAGG | TGAGTGGGAA | TGGCCCTTGC | TGACACCCAG | GGCCCTGGCT | GCAGGCATCT |
| CCATGGCTTT | GGCAGCCTCC | ACCAGCTCCT | TGGGTTGCTA | TGCTCTGTGT | GGCCAGCTGC |
| TGCGTTTGTC | TCCTCCGCCA | CCTCATGCCT | GCAGTCGAGG | GCTGAGCCTG | GAGGGGCTGG |
| GCAGTGTGCT | GGCAGGGCTG | CTGGGGAGCC | CCCTGGGCAC | TGCATCCAGC | TTCCCCAACG |
| TAGGCACAGT | GAGTCTTTTT | CAGACTGGCT | CTCGGAGAGT | GGCCCACCTA | GTGGGGTTGT |
| TCTGCATGGG | GCTTGGGCTC | TCCCCAAGGC | TGGCTCAGCT | ATtTACCAGC | ATCCCACTGC |
| CTGTGCTTGG | TGGGGTACTG | GGAGTGACCC | AGGCTGTAGT | TCTGTCTGCT | GGATTCTCCA |
| GCTTTCACCT | GGCTGACATT | GACTCTGGGC | GAAATGTCTT | CATCGTGGGC | TTCTCCATCT |
| TCATgGCCTT | GCTTTTGCCA | AGGTGGCTCA | GGGAAGCCCC | AGTCCTGCTC | AACACAGGCT |
| GGAGCCCCCT | GGATATGTTT | CTTCGTTCTT | TGCTGGCAGA | ACCCATTTTC | TTAGCTGGTC |
| TACTGGGCTT | TCTCCTAGAA | AACACTATAT | CTGGTACACG | GGCTGAGAGA | GGCTTAGGTC |
| AGAGGCTGCC | AACTTCTTTC | ACTGCCCAAG | AAATTCAAAT | GCTTCAGCAA | TCCAGGAGGA |
| AAGCTGCTCA | AGAGTATGGG | CTTCCTTTAC | CCATCAAAAA | CCTGTGTTCC | TGCATCCCAC |
| AGCCTCTCCA | CTGCCTCTGT | CCAATGCCTG | AAGACTCTGG | GGATGAAGGA | GGATCCTCTA |
| AAACAGGAGA | GAGAGCCGAC | TTGTTGCCTA | ACTCTGGGGA | ATCGTACTCC | ACAGCTAGCA |
| GAGAAGGGGT | TAGGTCCCAG | TAATCATCAA | GACCACCATT | TTTGTCTTAG | TTTAGCAGTA |
| ACTGCCACCT | TGCTGGAGTC | TGtATACTTT | GTCCCAGTGG | AGGTGGATGT | GGCCCACTTG |
| CAAAATGGGC | TGCCTTTCCT | CCTCTTAAGA | CTTGAGCAGA | GGCCATGGTT | TAGCGGGTTG |
| GAACTGAATA | AATGAGATTT | CTGCCTGTAA | AAAAAAAAAA | AAAAA1 | |

Form 2 (240-205-1)

| | | | | | |
|---|---|---|---|---|---|
| GCTGCTGCTT | CATGGTCTTC | CCCCAGGAGG | GCTCTCATAC | CCACCCGCTC | AGCTCCTGGC |
| TTCCAGTTTC | TTTTCATGTG | GCCTGTCTAC | GGTCCTGCAG | ACTTGGATGG | GCAGCAGGCT |
| ACCTCTAATC | CAGGCTCCGT | CCCTAGAGTT | TCTTATCCCC | GCACTGGTGC | TGACAAACCA |
| GAAGCTACCT | CTGACGACCA | AGACACCTGG | AAATGCCTCC | CTCTCACTGC | CCCTGTGTAG |
| TTTGACAAGA | AGCTGCCATG | GCCTGGAGCT | CTGGAACACT | TCTCTCCGAG | AGGTGTCGGG |
| GGCAGTGGTG | GTGTCCGGGC | TGCTGCAGGG | CACTATAGGA | CTTCTAGGGG | TGCCTGGCCG |
| TGTGTTCCCC | TACTGTGGGC | CACTGGTGCT | GGCTCCCAGC | CTGGTTGTGG | CAGGGCTTTC |
| TGCCCACAAG | GAGGTGGCCC | AGTTCTGTTC | TGCTcACTGG | GGCCTGGCTT | TGCTGCTCAT |
| CCTGCTCATG | GTGGTATGCT | CTCAGCACCT | GGGTTCATGC | CAGATACCCC | TTTgCTCCTG |
| GAGGCCATCT | TCAACTTCAA | CTCACATTTG | TATtCCCGTC | TTCCGACTCC | TTTCGGTGCT |
| TGCCCCTGTG | GCCTGTGTGT | GGTTCATCTC | TGCCTTTGTG | GGTACGAGTG | TTATCCCTCT |
| GCAGCTGTCT | GAGCCCTCGG | ATGCACCTTG | GTTTTGGCTG | CCACACCCAG | GTGAGTGGGA |
| ATGGCCCTTG | CTGACACCCA | GGGCCCTGGC | TGCAGGCATC | TCCATGGCTT | TGGCAGCCTC |
| CACCAGCTCC | TTGGGTTGCT | ATGCTCTGTG | TGGCCAGCTG | CTGCGTTTGT | CTCCTCCGCC |
| ACCTCATGCC | TGCAGTCGAG | GGCTGAGCCT | GGAGGGGCTG | GGCAGTGTGC | TGGCAGGGCT |
| GCTGGGGAGC | CCCCTGGGCA | CTGCATCCAG | CTTCCCCAAC | GTAGGCACAG | TGAGTCTTTT |
| TCAGACTGGC | TCTCGGAGAG | TGGCCCACCT | AGTGGGGTTG | TTCTGCATGG | GGCTTGGGCT |
| CTCCCCAAGG | CTGGCTCAGC | TATtTACCAG | CATCCCACTG | CCTGTGCTTG | GTGGGGTACT |
| GGGAGTGACC | CAGGCTGTAG | TTCTGTCTGC | TGGATTCTCC | AGCTTTCACC | TGGCTGACAT |
| TGACTCTGGG | CGAAATGTCT | TCATCGTGGG | CTTCTCCATC | TTCATgGCCT | TGCTTTTGCC |
| AAGGTGGCTC | AGGGAAGCCC | CAGTCCTGCT | CAACACAGGC | TGGAGCCCCC | TGGATATGTT |
| TCTTCGTTCT | TTGCTGGCAG | AACCCATTTT | CTTAGCTGGT | CTACTGGGCT | TTCTCCTAGA |
| AAACACTATA | TCTGGTACAC | GGGCTGAGAG | AGGCTTAGGT | CAGAGGCTGC | CAACTTCTTT |
| CACTGCCCAA | GAAATTCAAA | TGCTTCAGCA | ATCCAGGAGG | AAGCTGCTC | AAGAGTATGG |
| GCTTCCTTTA | CCCATCAAAA | ACCTGTGTTC | CTGCATCCCA | CAGCCTCTCC | ACTGCCTCTG |
| TCCAATGCCT | GAAGACTCTG | GGGATGAAGG | AGGATCCTCT | AAAACAGGAG | AGAGAGCCGA |
| CTTGTTGCCT | AACTCTGGGG | AATCGTACTC | CACAGCTAGC | AGAGAAGGGG | TTAGGTCCCA |
| GTAATCATCA | AGACCACCAT | TTTTGTCTTA | GTTTAGCAGT | AACTGCCACC | TTGCTGGAGT |
| CTGtATACTT | TGTCCCAGTG | GAGGTGGATG | TGGCCCACTT | GCAAAATGGG | CTGCCTTTCC |
| TCCTCTTAAG | ACTTGAGCAG | AGGCCATGGT | TTAGCGGGTT | GGAACTGAAT | AAATGAGATT |
| TCTGCCTGTA | AAAAAAAAAA | AAAAAA1 | | | |

Form 3 (240-4)

| | | | | | |
|---|---|---|---|---|---|
| atcttcatgg | ccttgctttt | gccaaggtgg | ctcagggaag | ccccagtcct | gctcaacaca |
| ggctggagcc | ccctggatat | gtttcttcgt | tctttgctgg | cagaacccat | tttcttagct |
| ggtctactgg | gctttctcct | agaaaacact | atatctggta | cacgggctga | gagaggctta |
| ggtcagaggc | tgccaacttc | tttcactgcc | caagaaattc | aaatgcttca | gcaatccagg |
| aggaaagctg | ctcaagagta | tgggcttcct | tacccatca | aaaacctgtg | ttcctgcatc |

TABLE 3-continued

Different cDNA forms of Yspl1; see SEQ ID NO: 1

| | | | | | |
|---|---|---|---|---|---|
| ccacagcctc | tccactgcct | ctgtccaatg | cctgaagact | ctggggatga | aggaggatcc |
| tctaaaacag | gagagagagc | cgacttgttg | cctaactctg | gggaatcgta | ctccacagct |
| agcagagaag | gggttaggtc | ccagtaatca | tcaagaccac | cattttttgtc | ttagtttagc |
| agtaactgcc | accttgctgg | agtctgtata | ctttgtccca | gtggaggtgg | atgtggccca |
| cttgcaaaat | gggctgcctt | tcctcctctt | aagacttgag | cagaggccat | ggtttagcgg |
| gttggaactg | aataaatgag | atttctgcct | gtaaaaaaa | aaaaaaaaa | aaaaaaaaaa |
| aaaaaaaaa1 | | | | | |

Form 4 (240-210B-1)

| | | | | | |
|---|---|---|---|---|---|
| GTTTCTTCGT | TCTTTGCTGG | CAGAACCCAT | TTTCTTAGCT | GGTCTACTGG | GCTTTCTCCT |
| AGAAAACACT | ATATCTGGTA | CACGGGCTGA | GAGAGGCTTA | GGTCAGAGGC | TGCcaacttc |
| tttcactgcc | caagaaattc | aaatgcttca | gcaatccagg | aggaaagctg | ctcaagagta |
| tgggcttcct | ttacccatca | aaaacctgtg | ttcctgcatc | ccacagcctc | tccactgcct |
| ctgtccaatg | cctgaagact | ctggggatga | aggaggatcc | tctaaaacag | gagagagagc |
| cgacttgttg | cctaactctg | gggaatcgta | ctccacagct | agcagagaag | gggttaggtc |
| ccagtaatca | tcaagaccac | cattttttgtc | ttagtttagc | agtaactgcc | accttgctgg |
| agtctgtata | ctttgtccca | gtggaggtgg | atgtggccca | cttgcaaaat | gggctgcctt |
| tcctcctctt | aagacttgag | cagaggccat | ggtttagcgg | gttggaactg | aataaatgag |
| atttctgcct | gtaaaaaaa | aaaaaaaaa | aaaaaaaaa | aaaaaaaa1 | |

What is claimed is:

1. A substantially pure or recombinant nucleic acid encoding a polypeptide comprising a plurality of non-overlapping segments of at least 8 amino acids from SEQ ID NO: 2.

2. The nucleic acid of claim 1, wherein said nucleic acid encodes at least three transmembrane segments of SEQ ID NO: 2.

3. A nucleic acid comprising a segment exhibiting identity to the portion of said nucleic acid of claim 1 which encodes said polypeptide comprising a plurality of non-overlapping segments of at least 8 amino acids.

4. The nucleic acid of claim 1, wherein said segments are from SEQ ID NO: 2.

5. The nucleic acid of claim 4, wherein said plurality is at least three, and said fragments include at least two with a length of at least 10 amino acids.

6. The recombinant nucleic acid of claim 1, wherein said plurality is at least three, said fragments include at least two with a length of at least 10 amino acids, and said seaments are from SEQ ID NO: 2.

7. The nucleic acid of claim 1, wherein said polypeptide comprises a sequence selected from the group consisting of:
   a) Met1 to Gln611, inclusive;
   b) Met107 to Gln611, inclusive;
   c) Met490 to Gln611, inclusive; and
   d) Met538 to Gln611, inclusive.

8. The nucleic acid of claim 1, wherein said polypeptide has the natural sequence of forms 1, 2, 3, or 4 of SEQ ID NO: 2.

9. The nucleic acid of claim 8, wherein said polypeptide exhibits an activity selected from the group consisting of:
   a) a nucleobase binding affinity; and
   b) a nucleobase permease activity.

10. A recombinant or isolated nucleic acid comprising a sequence exhibiting identity to a fragment of at least 30 nucleotides from nucleotidss 48–1880 of SEQ ID NO: 1.

11. A method of making a polypeptide comprising expressing a nucleic acid of claim 10.

12. A kit comprising instructions for use and:
   a) a nucleic acid encoding a polypeptide comprising a plurality of non-overlapping segments of at least 8 amino acids from SEQ ID NO: 2; or
   b) said nucleic acid of claim 10.

13. The nucleic acid of claim 10, wherein said nucleic acid is:
   a) a PCR product;
   b) a hybridization probe;
   c) a mutagenesis primer; or
   d) a PCR primer.

14. The nucleic acid of claim 13, which is a detectably labeled hybridization probe.

15. The nucleic acid of claim 10, wherein said nucleic acid is an expression vector.

16. The nucleic acid of claim 15, wherein said expression vector is suitable for transfection.

17. The nucleic acid of claim 15, wherein said expression vector is transfected into a suitable host cell.

18. The nucleic acid of claim 17, wherein said host cell is selected from the group consisting of;
   a) a bacterial cell;
   b) a yeast cell;
   c) an insect cell: and
   d) a mammalian cell.

19. The nucleic acid of claim 11, wherein said sequence exhibits identity to a fragment of at least 50 nucleotides of nucleotides 48–1880 of SEQ ID NO: 1.

20. A substantially pure or recombinant nucleic acid comprising a strand which hybridizes to nucleotides 48–1880 of SEQ ID NO: 1 at a temperature of at least 55° C. and a salt concentration of less than 330 mM.

21. The nucleic acid of claim 20, wherein said temperature is at least 65° C., and said salt concentration is less than 300 mM.

22. The nucleic acid of claim 20, which encodes at least 16 amino acids of SEQ ID NO: 2.

23. A method of making a polypeptide encoded by a nucleic acid of claim 21 comprising expressing said nucleic acid, wherein said expressing produces said polypeptide.

24. A method of making a duplex nucleic acid comprising contacting a single strand nucleic acid of claim 21 to a second single strand nucleic acid, wherein said contacting forms a duplex which is stable at 55° C. and a salt concentration of less than 300 mM.

25. The nucleic acid of claim 21 in an expression vector.

* * * * *